United States Patent
Weinberg et al.

(10) Patent No.: US 11,572,541 B2
(45) Date of Patent: Feb. 7, 2023

(54) UTILIZATION OF CD39 AND CD103 FOR IDENTIFICATION OF HUMAN TUMOR REACTIVE T CELLS FOR TREATMENT OF CANCER

(71) Applicants: Providence Health & Services—Oregon, Portland, OR (US); AgonOx, Inc., Portland, OR (US)

(72) Inventors: Andrew D. Weinberg, Portland, OR (US); Ryan Montier, Camas, WA (US); Thomas Duhen, Portland, OR (US); Rebekka Duhen, Portland, OR (US)

(73) Assignees: Providence Health & Services—Oregon, Portland, OR (US); AgonOx, Inc., Portland, OR (US)

( * ) Notice: Subject to any disclaimer, the term of this patent is extended or adjusted under 35 U.S.C. 154(b) by 443 days.

(21) Appl. No.: 16/616,932

(22) PCT Filed: May 4, 2018

(86) PCT No.: PCT/US2018/031197
§ 371 (c)(1),
(2) Date: Nov. 25, 2019

(87) PCT Pub. No.: WO2018/226336
PCT Pub. Date: Dec. 13, 2018

(65) Prior Publication Data
US 2020/0149008 A1 May 14, 2020

Related U.S. Application Data

(60) Provisional application No. 62/517,612, filed on Jun. 9, 2017.

(51) Int. Cl.
| | | |
|---|---|---|
| *C12N 5/0783* | (2010.01) | |
| *A61K 35/17* | (2015.01) | |
| *C07K 14/725* | (2006.01) | |
| *A61K 48/00* | (2006.01) | |
| *C12N 15/10* | (2006.01) | |
| *C12N 15/85* | (2006.01) | |

(52) U.S. Cl.
CPC .......... *C12N 5/0636* (2013.01); *A61K 35/17* (2013.01); *C07K 14/7051* (2013.01); *C12N 15/1003* (2013.01); *C12N 15/85* (2013.01); *A61K 48/00* (2013.01); *C12N 2500/32* (2013.01); *C12N 2501/2315* (2013.01); *C12N 2502/00* (2013.01)

(58) Field of Classification Search
None
See application file for complete search history.

(56) References Cited

U.S. PATENT DOCUMENTS

2015/0210769 A1* 7/2015 Freeman .................... A61P 5/14
435/254.2

FOREIGN PATENT DOCUMENTS

| WO | WO-2013006474 A2 * | 1/2013 | ............ A61K 35/17 |
| WO | WO2009/145238 A1 | 7/2017 | |

OTHER PUBLICATIONS

Pallett et al. (J. Exp. Med May 19, 2017, 214 (6): 1567-1580) (Year: 2017).*
Djenidi et al., "CD8+ CD103+ tumor-infiltrating lymphocytes are tumor-specific tissue-resident memory T cells and a prognostic factor for survival in lung cancer patients," *The Journal of Immunology*, 194(7): 3475-3486 (E-pub Feb. 27, 2015).
Duhen et al., "Identification of a novel subset of tumor-resident human CD8 T cells that co-express CD103 and CD39," poster presented on Oct. 3-5, 2016 at the Immune Profiling in Health and Disease meeting in Seattle, WA.
Duhen et al., "P69 Identification of a novel subset of tumor-resident human CD8+ T cells, marked by dual expression of CD103 and CD39," *31st Annual Meeting and Associated Programs of the Society for Immunotherapy of Cancer (SITC 2016): part one: Journal for Immunotherapy of Cancer*, 4(1): 109 pages, (Nov. 16, 2016)(Abstract on p. 47).
International Search Report and Written Opinion issued for International Application No. PCT/US2018/031197, 11 pages (dated Jul. 25, 2018).
Liu et al., "Tumor-infiltrating lymphocytes (TILs) from patients with glioma," *Oncoimmunology*, 6(2): 9 pages (E-pub Nov. 29, 2016).
Gupta et al., "CD39 expression identifies terminally exhausted CD8+ T cells," *PLOS Pathogens* 11(10): 21 pp (Oct. 20, 2015).
Koch et al., "Alloantigen-induced regulatory CD8+CD103+T cells," *Human Immunology* 69: 737-744 (e-Pub Sep. 24, 2008).
Webb et al., "Tumor-infiltrating lymphocytes expression the tissue resident memory marker CD103 are associated with increased survival in high-grade serious ovarian cancer," *Clinical Cancer Research* 20(2): 434-444 (e-Pub Nov. 4, 2013).

* cited by examiner

*Primary Examiner* — Peter J Reddig
(74) *Attorney, Agent, or Firm* — Klarquist Sparkman, LLP

(57) ABSTRACT

Methods are disclosed for treating a subject with a tumor. These methods include administering to the subject a therapeutically effective amount of CD8+CD39+CD103+ T cells. Methods also are disclosed for isolating a nucleic acid encoding a T cell receptor (TCR) that specifically binds a tumor cell antigen. These methods include isolating CD8+CD39+CD103+ T cells from a sample from a subject with a tumor expressing the tumor cell antigen, and cloning a nucleic acid molecule encoding a TCR from the CD8+CD39+CD103+ T cells. In addition, methods are disclosed for expanding CD8+CD39+CD103+ T cells. In additional embodiments, methods are disclosed for determining if a subject with a tumor will respond to a checkpoint inhibitor. The methods include detecting the presence of CD8+CD39+CD103+ T cells in a biological sample from a subject.

10 Claims, 24 Drawing Sheets
Specification includes a Sequence Listing.

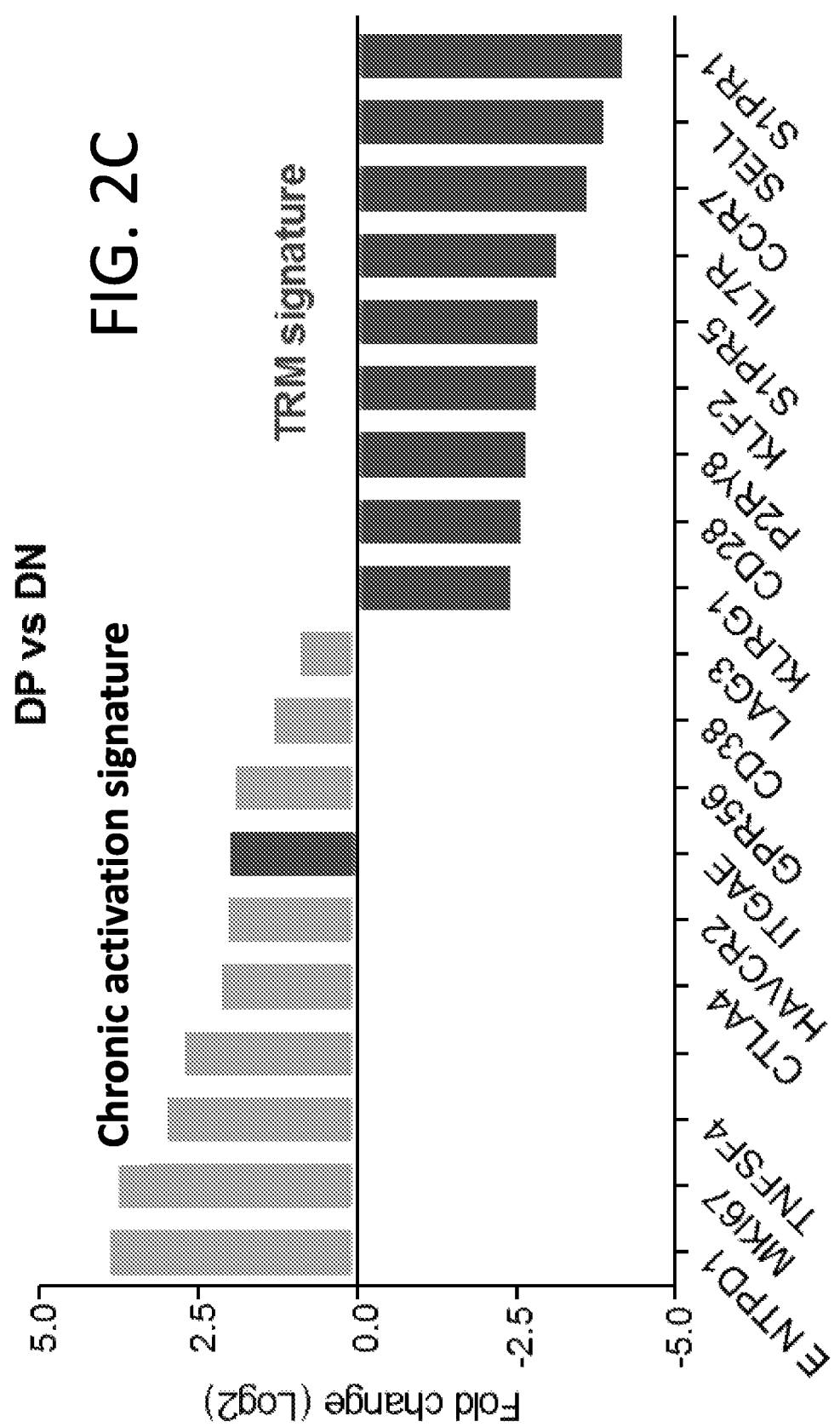

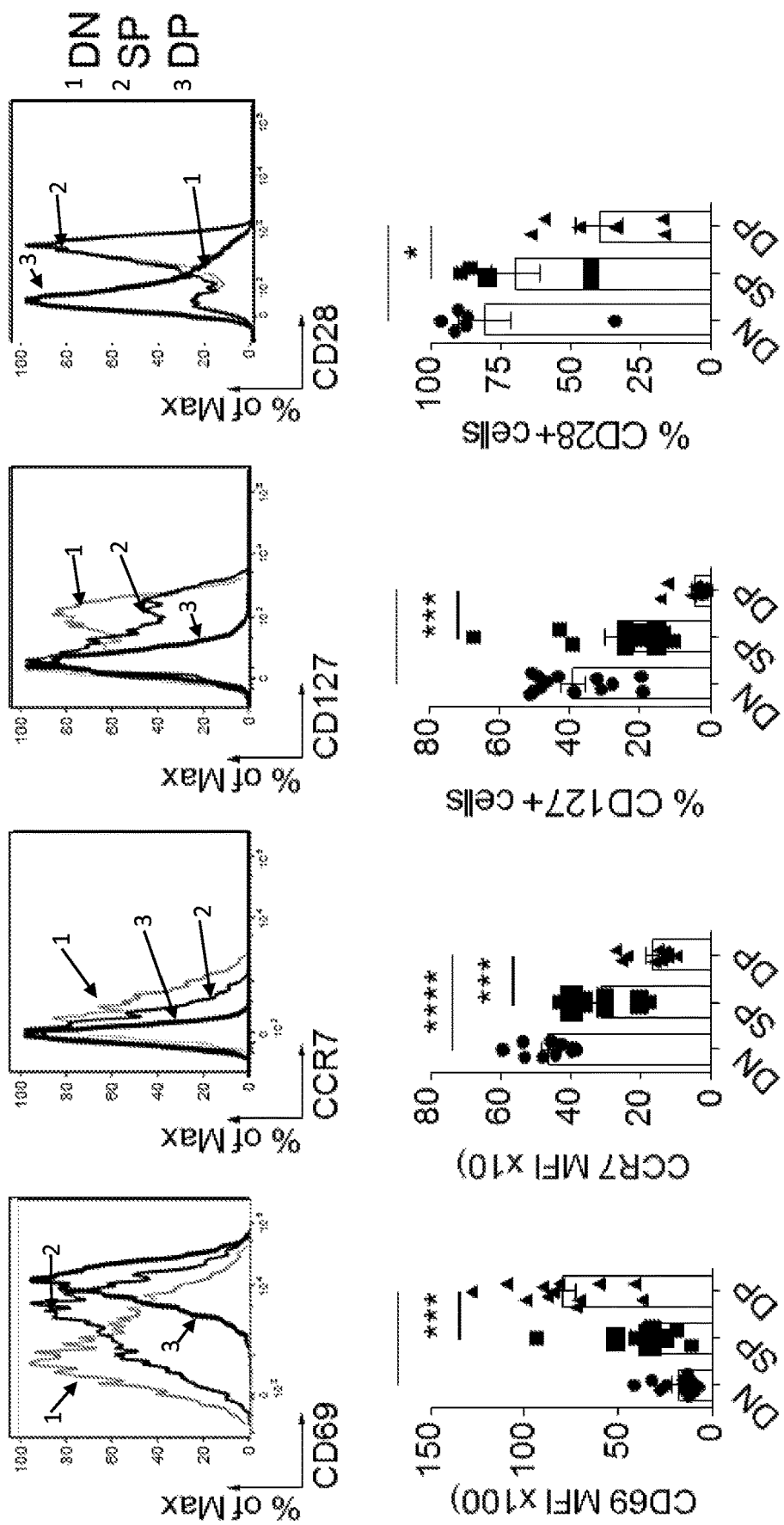

T=0hrs   T=20hrs

FIG. 7A

| Freq. in DP CD8 TIL (% of total clonotypes) | | TCRB CDR3 region (Nucleotide sequence) |
|---|---|---|
| Prior coculture | Tumor-reactive | |
| 4.584 | 6.141 | CCGCTCAGGCTGGAGTTGGCTGCTCCCTCC CAGACATCTGTGTACTTCTGTGCCAGCAGT TGGGGTGGCGAGCAGTACTTCGGGCCG |
| 3.776 | 0.340 | CTGAGCTCTCTGGAGCTGGGGGACTCAGCT TTGTATTTCTGTGCCAGCAGCGGGACAGTT AACACCGGGGAGCTGTTTTTTGGAGAA |
| 3.190 | 0.783 | GAGTCCGCCAGCACCAACCAGACATCTATG TACCTCTGTGCCAGCAGTTTCCGGGACAGG GGGCTTCAGCCCCAGCATTTTGGTGAT |
| 3.111 | 1.463 | ACGATCCAGCGCACACAGCAGGAGGACTC GGCCGTGTATCTCTGTGCCAGCAGCTCGAC AGGGGGCTACGAGCAGTACTTCGGGCCG |
| 2.932 | 4.316 | CTGAGCTCTCTGGAGCTGGGGGACTCAGCT TTGTATTTCTGTGCCAGCAGCTTCGGACAG GGGGCCTACGAGCAGTACTTCGGGCCG |
| 2.697 | 0.095 | CAGCGCACAGAGCAGGGGGACTCGGCCAT GTATCTCTGTGCCAGCAGGCAGGAGACAGC CGGGAACACTGAAGCTTTCTTTGGACAA |
| 2.568 | 11.506 | CTGGAGTCCGCCAGCACCAACCAGACATCT ATGTACCTCTGTGCCAGCAGTTTAGCTAGA AACACCGGGGAGCTGTTTTTTGGAGAA |
| 2.237 | 3.949 | AAGATCCAGCCTGCAAAGCTTGAGGACTCG GCCGTGTATCTCTGTGCCAGCAGCACGACT AGTTCAGATACGCAGTATTTTGGCCCA |
| 2.099 | 0.047 | CAGCGCACAGAGCAGCGGGACTCGGCCAT GTATCGCTGTGCCAGCAGCGAGGAGCCCG GGATCGATGAAAACTGTTTTTTGGCAGT |
| 2.025 | 0.905 | GAGTCGCCCAGCCCCAACCAGACCTCTCTG TACTTCTGTGCCAGCAGTCTCGGGGGATAT AGCAATCAGCCCCAGCATTTTGGTGAT |
| 1.939 | 1.388 | ACTCTGACAGTGACCAGTGCCCATCCTGAA GACAGCAGCTTCTACATCTGCAGCGCTTGG ACAGGCTACGAGCAGTACTTCGGGCCG |
| 1.832 | 0.667 | ATCCAGCGCACACAGCAGGAGGACTCCGC CGTGTATCTCTGTGCCAGCACCCAACTATTA ATGATCAATGAGCAGTTCTTCGGGCCA |
| 1.825 | 4.146 | CGCACAGAGCAGGGGGACTCGGCCATGTA TCTCTGTGCCAGCAGTTATGGCCCCGGGAC AGTTAATGAAAACTGTTTTTTGGCAGT |
| 1.817 | 4.663 | CTGGAGTCGGCTGCTCCCTCCCAGACATCT GTGTACTTCTGTGCCAGCAAGGGCCCCTTT GGGCGGAATGAGCAGTTCTTCGGGCCA |
| 1.651 | 1.280 | ATCCAGCGCACAGAGCAGGGGGACTCGGC CATGTATCTCTGTGCCAGCAGCTCGATTCT CGGGGCGGGGACGCAGTATTTTGGCCCA |

FIG. 7B

| Freq. in DP CD8 TIL (% of total clonotypes) | | TCRB CDR3 region (Nucleotide sequence) |
|---|---|---|
| Prior coculture | Tumor-reactive | |
| 17.728 | 19.727 | CGCACAGAGCAGGGGGACTCGGCCATGTATCTCTGTGCCAGCAGCCGCACTCAGGGGTCGGGTAAGGAGCCCCAGCATTTTGGTGAT |
| 6.919 | 16.125 | TCTAAGAAGCTCCTTCTCAGTGACTCTGGCTTCTATCTCTGTGCCTGGAGTGTGGGACTCCAGAACACTGAAGCTTTCTTTGGACAA |
| 5.381 | 2.651 | CTGAGCTCTCTGGAGCTGGGGGACTCAGCTTTGTATTTCTGTGCCAGCAGCGAAGGGTATCCGTCAGAAAACTGTTTTTGGCAGT |
| 4.772 | 9.584 | AAGATCCGGTCCACAAAGCTGGAGGACTCAGCCATGTACTTCTGTGCCAGAAACAGGGGTAAGGGGAATGAGCAGTTCTTCGGGCCA |
| 4.462 | 7.023 | CCGCTCAGGCTGGAGTTGGCTGCTCCTCCCAGACATCTGTGTACTTCTGTGCCAGCAGTTGGGGTGGCGAGCAGTACTTCGGGCCG |
| 3.537 | 0.050 | ACTGTGACATCGGCCCAAAAGAACCCGACAGCTTTCTATCTCTGTGCCAGCAACCCAGGGTGGTACACTGAAGCTTTCTTTGGACAA |
| 3.518 | 0.021 | ATCCAGCCCTCAGAACCCAGGGACTCAGCTGTGTACTTCTGTGCCAGCAGCCCGCGGGGGTCTTACAATGAGCAGTTCTTCGGGCCA |
| 3.093 | 3.790 | CAGCGCACAGAGCAGGGGGACTCGGCCATGTATCTCTGTGCCAGCAGCTCCCGGGTAGCTCCTACAATGAGCAGTTCTTCGGGCCA |
| 3.010 | 1.553 | ATCAATTCCCTGGAGCTTGGTGACTCTGCTGTGTATTTCTGTGCCAGCAGCTTTGGACAGGGGGCCTACGAGCAGTACTTCGGGCCG |
| 3.007 | 6.393 | AAGAAGCTCCTTCTCAGTGACTCTGGCTTCTATCTCTGTGCCCTTATACTAGTCGGGACAATACGAGAGACCCAGTACTTCGGGCCA |
| 2.991 | 3.602 | GAGTCGCCCAGCCCCAACCAGACCTCTCTGTACTTCTGTGCCAGCAGTCTCGGGGATATAGCAATCAGCCCCAGCATTTTGGTGAT |
| 2.499 | 0.093 | ACTGTGACATCGGCCCAAAAGAACCCGACAGCTTTCTATCTCTGTGCCAGTATTAGTGGGTGGGGCACTGAAGCTTTCTTTGGACAA |
| 2.398 | 0.058 | CGCACAGAGCAGGGGGACTCGGCCATGTATCTCTGTGCCAGCAGTTATGGCCCCGGGACAGTTAATGAAAACTGTTTTTGGCAGT |
| 2.368 | 0.114 | GCCCAAAAGAACCCGACAGCTTTCTATCTCTGTGCCAGTAGTCCCCCCGACAGGGGTCGCGGCAAGAGACCCAGTACTTCGGGCCA |
| 2.208 | 7.404 | CTAAACCTGAGCTCTCTGGAGCTGGGGGACTCAGCTTTGTATTTCTGTGCCAGCAGCGGACAGGGGGCGAAGCAGTACTTCGGGCCG |

UTILIZATION OF CD39 AND CD103 FOR IDENTIFICATION OF HUMAN TUMOR REACTIVE T CELLS FOR TREATMENT OF CANCER

CROSS REFERENCE TO RELATED APPLICATIONS

This is the U.S. National Stage of International Application No. PCT/US2018/031197, filed May 4, 2018, which claims the benefit of U.S. Provisional Application No. 62/517,612, filed Jun. 9, 2017, which is incorporated herein by reference.

FIELD

This relates to the field of cancer, specifically to the use of adoptive transfer of cells, such as $CD8^+CD39^+CD103^+$ T cells, and the use of T cell receptors (TCRs), such as from $CD8^+CD39^+CD103^+$ T cells, for the treatment of tumors, and related to methods for assessing treatment, such as by measuring $CD8^+CD39^+CD103^+$ T cells.

BACKGROUND

The immune system plays a major role in recognizing and killing tumor cells and new therapeutic approaches have focused on boosting and/or restoring its function in cancer patients. An effective immune response involves the concerted action of several different cell types among which CD8 T cells are key players that can specifically recognize and kill cancer cells via the release of cytotoxic molecules and cytokines (Klebanoff C A et al., 211:214-24, Immunol. Rev., 2006). Tumor-infiltrating CD8 T cells recognize tumor-associated antigens (TAA's), which can comprise self-antigens that are overexpressed in neoplastic lesions, as well as tumor-specific antigens (TSA's) or neoantigens, which arise as a consequence of tumor-specific mutations (Finn O J, Cancer Immunol Res, 2017). According to the current paradigm, tumor-specific CD8 T cells are primed in tumor-draining lymph nodes and then migrate via the blood to the tumor to exert their effector function. Previous work has shown that tumor-infiltrating CD8 T cells represent a heterogeneous population of cells comprised of tumor-specific T cells as well as bystander T cells with no tumor specificity. The latter are recruited to the tumor site by the inflammation associated with tumor progression (proliferation, angiogenesis and metastasis). However, a need remains for immunotherapeutic methods, wherein the efficacy/efficiency of adoptive transfer is increased.

SUMMARY

The phenotype and function of tumor-reactive CD8 T cells was evaluated, and it was determined that co-expression of CD103 and CD39 identified a population of tumor-infiltrating CD8 T cells specifically induced in the tumor microenvironment. These cells, which are chronically stimulated within the tumor, were highly enriched for tumor reactivity and had the ability to kill autologous tumor cells. A higher frequency of $CD8^+CD39^+CD103^+$ T cells in human tumors correlated with a greater overall survival. It was determined that the presence of $CD8^+CD39^+CD103^+$ T cells can indicate that a therapeutic method is effective for treating a tumor. In addition, $CD8^+CD39^+CD103^+$ T cells can be adoptively transferred into a subject to treat a tumor.

Methods are disclosed for treating a subject with a tumor, including administering to the subject a therapeutically effective amount of $CD8^+CD39^+CD103^+$ T cells, thereby treating the subject with the tumor. In some embodiments, the method includes administering a therapeutically effective amount of a Programmed Death (PD)-1 antagonist, a Programmed Death Ligand (PD-L)1 antagonist, a Cytotoxic T-lymphocyte-Associated Protein 4 (CTLA-4) antagonist, a B- and T-lymphocyte Attenuator (BTLA) antagonist, T-cell Immunoglobulin and Mucin-domain containing-3 (TIM-3) antagonist, a Lymphocyte-Activation Gene 3 (LAG3) antagonist, or a 4-1BB agonist to the subject.

In some embodiments, methods are disclosed for isolating a nucleic acid sequence encoding a T cell receptor (TCR) that specifically binds a tumor cell antigen. These methods include isolating $CD8^+CD39^+CD103^+$ T cells from a subject with a tumor expressing the tumor cell antigen, and cloning the nucleic acid sequence encoding a TCR molecule from the $CD8^+CD39^+CD103^+$ T cells, thereby isolating a nucleic acid sequence encoding the TCR specific for the tumor.

In additional embodiments, methods are disclosed for expanding $CD8^+CD39^+CD103^+$ T cells. These methods include culturing $CD8^+CD39^+CD103^+$ T cells in a tissue culture medium comprising glutamine, serum, and antibiotics; stimulating the isolated T cells with an effective amount of allogenic irradiated feeder cells and a cytokine; and culturing the stimulated T cells in a tissue culture medium and an effective amount of the cytokine.

In yet other embodiments, methods are disclosed for determining if a subject with a tumor will respond to a cancer therapeutic, such as checkpoint inhibitor, biological response modifier (for example, cytokines and chemokines), a cancer vaccine, chemotherapy and/or radiation. Methods are also disclosed for determining if a subject will respond to a surgical procedure. The methods include detecting the presence of $CD8^+CD39^+CD103^+$ T cells in a biological sample from a subject, wherein the presence of the $CD8^+CD39^+CD103^+$ T cells in the biological sample indicates that the cancer therapeutic or the surgical procedure will be effective for treating the tumor in the subject. In some non-limiting examples, the methods can also include administering the cancer therapeutic to the subject, or preforming the surgical procedure.

In further embodiments, methods are disclosed for determining if a subject with a tumor will respond to a cancer therapeutic. The methods include administering to the subject a first dose of the cancer therapeutic, and determining the number of $CD8^+CD39^+CD103^+$ T cells in a biological sample from the subject. An increase in the number of $CD8^+CD39^+CD103^+$ T cells in the biological sample as compared to a control indicates that the first dose of the cancer therapeutic is effective for treating the tumor in the subject.

In more embodiments, methods are disclosed for treating a subject with a tumor. The methods include administering to a subject a first dose of the cancer therapeutic, and determining the number of $CD8^+CD39^+CD103^+$ T cells in a biological sample from the subject. An increase in the amount of $CD8^+CD39^+CD103^+$ T cells in the biological sample as compared to a control indicates that the first dose of the cancer therapeutic is effective for treating the tumor in the subject. A second dose of the cancer therapeutic is administered to the subject, wherein the first dose is the same as the second dose, or wherein the second dose is lower than the first dose.

In other embodiments, methods are disclosed for treating a subject with a tumor. The methods include administering to the subject a first dose of a cancer therapeutic, and determining the number of CD8⁺CD39⁺CD103⁺ T cells in a biological sample from the subject. A decrease or no change in the amount of CD8⁺CD39⁺CD103⁺ T cells in the biological sample as compared to a control indicates that the first dose of the cancer therapeutic is not effective for treating the tumor in the subject. A second dose of the cancer therapeutic is administered to the subject wherein the second dose is higher than the first dose, or wherein the second dose is the same as the first dose.

The foregoing and other objects, features, and advantages of the invention will become more apparent from the following detailed description, which proceeds with reference to the accompanying figures.

BRIEF DESCRIPTION OF THE DRAWINGS

FIGS. 2A-2D. Gene expression profiling of CD8+ CD39+ CD103+ TIL reveals a profile reminiscent of $T_{RM}$ cells. (A) Principal component analysis (PCA) of gene expression of sorted DN, SP and DP CD8 TIL isolated from 3 HNSCC and 2 ovarian cancer patients. The analysis was performed on genes differentially expressed between double positive (DP) and double negative (DN) CD8 TIL (n=372). (B) Unsupervised clustering of samples using the 372 differentially expressed genes between DP and DN CD8 TIL. Dark grey color indicates downregulated genes, light grey indicates upregulated genes. (C) Waterfall plot representing the fold change (log 2) of the most upregulated and downregulated genes in DP vs DN subsets. Light grey identifies genes with a chronic activation signature; dark grey indicates genes associated with the TRM phenotype. (D) Expression of the top differentially expressed genes in each of the 5 patients analyzed. The top row shows genes associated with the $T_{RM}$ phenotype, bottom row indicates chronic activation signature genes. Each symbol represents a patient, which are connected with lines.

FIGS. 3A-3E. Phenotypic and functional properties of DP, SP and DN CD8 TIL. (A) Ex vivo phenotypic analysis of the expression of surface proteins CD69, CCR7, CD127 and CD28, delineating a $T_{RM}$ phenotype, on CD8 TIL (top). Summary of the frequency of above mentioned markers among several cancer patients (n=6-13, bottom). *p<0.05; *p<0.001; p<0.0001 (ANOVA). (B) Ex vivo phenotypic analysis of the expression of surface and intracellular proteins PD-1, CTLA-4, TIM-3, 4-1BB and Ki-67, delineating an activated/chronically stimulated phenotype, on CD8 TIL (top). Summary of the frequency of above mentioned markers among several cancer patients (n=5-17, bottom). *p<0.001; ****p<0.0001 (ANOVA). (C) Representative flow cytometric analysis of IFN-γ, and TNF-α production by CD8 TIL subsets stimulated for 4 hrs with PMA/Ionomycin. Numbers in each quadrant indicate percent cells positive for IFN-γ and/or TNF-α on CD3+CD8+ T cells. (D) Frequency of IFN-γ, TNF-α, IFN-γ/TNF-α double positive cells by CD8 TIL subsets. Data are from 6 HNSCC patients. (E) Representative flow cytometric analysis of granzyme B production by CD8 TIL (left) and summary of 6 different HNSCC patients (right). *p<0.05; **p<0.01 (ANOVA).

FIGS. 7A-7C. DP CD8 TIL are enriched in tumor reactive cells and the primary tumor TCR repertoire overlaps with the metastatic LN TCR repertoire within the same Individual. (A) and (B) DP CD8 TIL were sorted and expanded in vitro. After expansion, DP CD8 TIL were cocultured with autologous tumor cells for 24 hrs. At the end of the culture, cells were sorted based on their expression of 4-1BB and CD25. The TCR repertoire of DP CD8 TIL prior to coculture was compared to the TCR repertoire of 4-1BB+CD25+ DP CD8 TIL (tumor-reactive). The top 15 clonotypes in the DP CD8 TIL prior to co-culture are present with their respective frequencies before and after coculture with tumor cells. The results from two cancer patients are indicated. (C) The 500 most frequent DP CD8 TIL clonotypes are plotted based on their frequency in the primary tumor and the metastatic LN. The results from two HNSCC patients are indicated. SEQ ID NOs: 1-15 are shown in FIG. 7A, in order from top (SEQ ID NO:1) to bottom (SEQ ID NO: 15). SEQ ID NOs: 16-30 are shown in FIG. 7B, in order from top (SEQ ID NO: 16) to bottom (SEQ ID NO: 30).

SEQUENCE LISTING

Figure 1A:
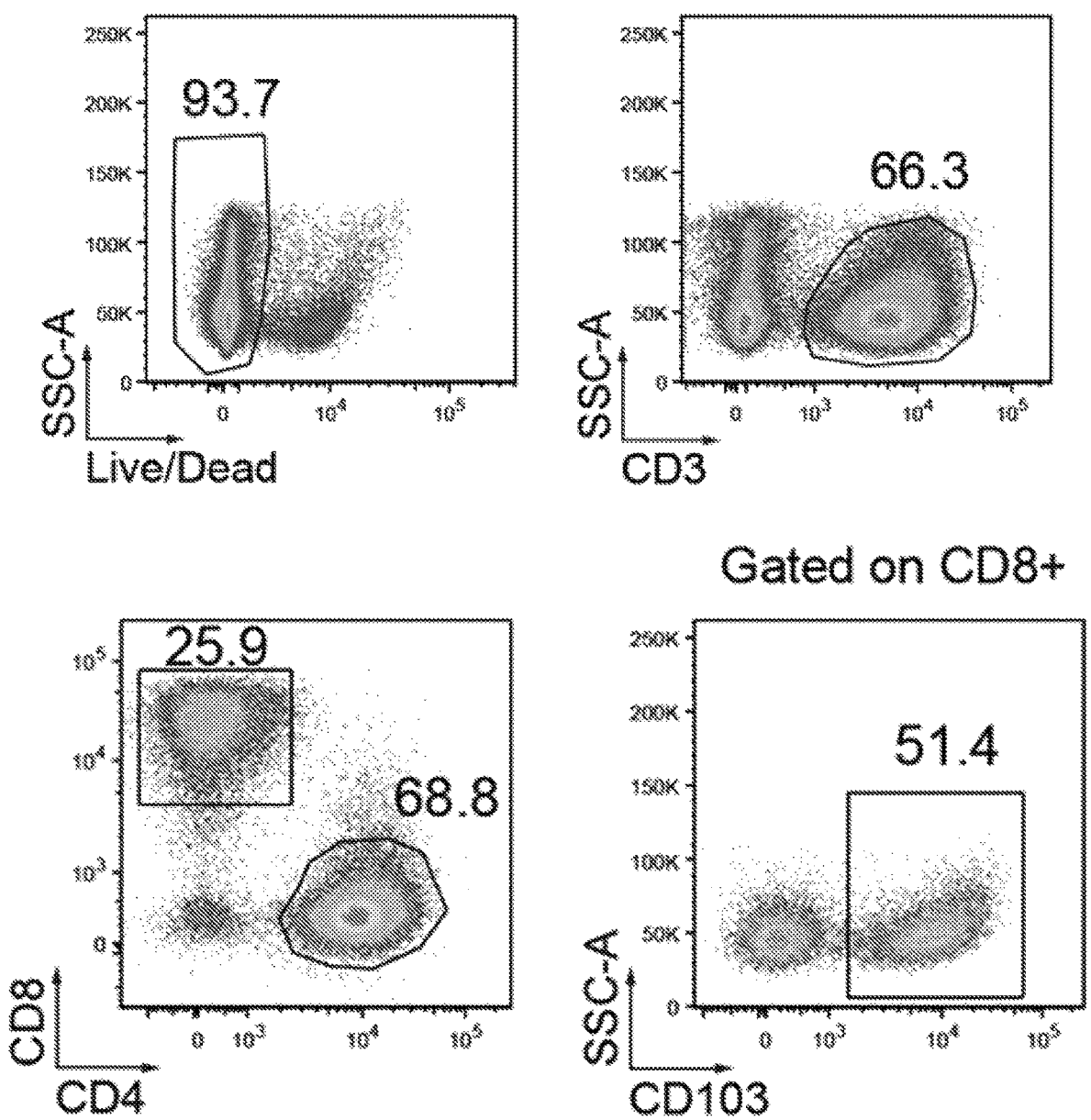
FIGS. 1A-1F. Tumor-infiltrating CD103+ CD8 T cells coexpress the ectonucleotidase CD39. (A) Representative gating strategy for the flow cytometric analysis of T cells infiltrating a head and neck squamous cell carcinoma (HNSCC). Numbers in plots indicate the percent cells in respective gates. (B) viSNE analysis of tumor infiltrating lymphocytes (TIL) gated on CD103+ CD8 T cells as shown in (A). The gate identifies CD103+ CD8 T cells with the highest expression of CD39. The gate is applied to all plots showing expression levels of PD-1, CD69 and CD127. (C) Flow cytometric analysis of CD8 TIL isolated from HNSCC, Melanoma, Ovarian and CRLM cancer patients. Numbers in each quadrant indicate percent cells positive for CD39 and/or CD103 on CD3+CD8+ T cells. (D) Summary of the frequency of CD39⁺CD103+(DP) CD8 TIL among patients with different solid malignancies. Shown are 40 HNSCC patients, 2 lung cancer patients, 6 melanoma patients, 2 ovarian cancer patients, 3 rectal cancer patients, 3 patients with colon cancer and 6 patients with CRLM. The red circle highlights one colon patient with Lynch's syndrome, leading to microsatellite instability (MSI). (E) Flow cytometric analysis of the percentage of DP CD8 T cells in peripheral blood, normal LN, primary tumor and metastatic LN from one HNSCC patient. Numbers in each quadrant indicate percent cells positive for CD39 and/or CD103 on CD3+CD8+ T cells. Data are representative of 40 HNSCC patients analyzed (only 9 patients for normal LN and Met LN). Percentages are summarized in (F).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [6727-98940-10 Sequence_Listing, Nov. 22, 2019, 7.11 KB], which is incorporated by reference herein. In the accompanying sequence listing:

SEQ ID NOs: 1-30 are the nucleotide sequences of exemplary TCRB CDR3 regions.

DETAILED DESCRIPTION

There is a need to improve the efficacy of immunotherapy and adoptive T cell transfer for cancer patients, and a need to characterize CD8 T cells involved in the anti-tumor response, in order to use a particular sub-population for diagnostic methods. CD39$^+$CD8$^+$ T cells include CD39+ CD103+ CD8+ T cells and CD39+ CD103−CD8+ T cells. It is disclosed herein that the phenotype and function of tumor-reactive CD8 T cells was determined, and it was documented that the co-expression of CD103 and CD39 identified a unique population of tumor-infiltrating CD8 T cells specifically induced in the tumor microenvironment. These cells, which are chronically stimulated within a tumor, are highly enriched for tumor reactivity and have the ability to kill autologous tumor cells. A higher frequency of CD103+CD39+CD8 T cells in human tumors correlated with a greater overall survival, indicating that the evaluation of these cells in biological samples provides methods for determining the efficacy of treatment, and for evaluating whether a subject with a tumor will respond to treatment.

Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

4-1BB: A transmembrane protein, also referred to as CD137 and TNFRSF9, that is a protein of the Tumor necrosis factor receptor superfamily (TNFRS). Expression of 4-1BB is generally activation dependent and is present in a broad subset of immune cells including activated NK and NKT cells, regulatory T cells, activated CD4 and CD8 T cells, dendritic cells (DC), stimulated mast cells, differentiating myeloid cells, monocytes, neutrophils, and eosinophils (Wang, 2009, Immunological Reviews 229: 192-215), 4-1BB expression has also been demonstrated on tumor vasculature (Broll, 2001, Amer. J. Clin. Pathol. 115(4):543-549; Seaman, 2007, Cancer Cell 11: 539-554) and at sites of inflamed or atherosclerotic endothelium (Drenkard, 2007 FASEB J. 21: 456-463; Olofsson, 2008, *Circulation* 117: 1292-1301). The ligand that stimulates 4-1BB, i.e., 4-1BB Ligand (4-1BBL), is expressed on activated antigen-presenting cells (APCs), myeloid progenitor cells, and hematopoietic stem cells. Human 4-1BB is a 255 amino acid protein (See GENBANK Accession Nos. NM_001561 and NP-001552, incorporated herein by reference as available on Jun. 1, 2017). Agonist antibodies of 4-1BB are disclosed, for example, in U.S. Pat. No. 8,337,850, incorporated herein by reference.

Altering level: Changing, either by increasing or decreasing, the number of cells of a specific cell type, or the level of production or expression of a nucleic acid sequence or an amino acid sequence (for example a polypeptide, an siRNA, a miRNA, an mRNA, a gene), as compared to a control level.

Antisense, Sense, and Antigene: DNA has two antiparallel strands, a 5'-3' strand, referred to as the plus strand, and a 3'-5' strand, referred to as the minus strand. Because RNA polymerase adds nucleic acids in a 5'-3' direction, the minus strand of the DNA serves as the template for the RNA during transcription. Thus, an RNA transcript will have a sequence complementary to the minus strand, and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target. An antisense RNA (asRNA) is a molecule of RNA complementary to a sense (encoding) nucleic acid molecule.

Antibody: A polypeptide ligand comprising at least a light chain or heavy chain immunoglobulin variable region which recognizes and binds (such as specifically recognizes and specifically binds) an epitope of an antigen, such as a PD-1, PD-L1, CTLA-4, BTLA, TIM-3, LAG3 or 4-1BB polypeptide, or a fragment thereof. Immunoglobulin molecules are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as single-domain antibodies (e.g. VH domain antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, Ill.); Kuby, J., *Immunology,* 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined according to Kabat et al. (see, Kabat et al., *Sequences of Proteins of Immunological Interest*, U.S. Department of Health and Human Services, 1991) and ImMunoGeneTics database (IMGT) (see, Lefranc, *Nucleic Acids Res* 29:207-9, 2001; and imgt.cines.fr/IMGT_vquest/vquest?_livret=0-&Option=humanIg). The Kabat database is maintained online (ncbi.nlm.nih.gov/igblast/). The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 (or H-CDR3) is located in the variable domain of the heavy chain of the antibody in which it is found, whereas a $V_L$ CDR1 (or L-CDR1) is the CDR1 from the variable domain of the light chain of the antibody in which it is found. An antibody that binds PD-1, PD-L, or PD-L2, for example, will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "$V_H$" refer to the variable region of an immunoglobulin heavy chain, including that of an Fv, scFv, dsFv or Fab. References to "$V_L$" or "$V_L$" refer to the variable region of an immunoglobulin light chain, including that of an Fv, scFv, dsFv or Fab.

A "monoclonal antibody" is an antibody produced by a single clone of B-lymphocytes or by a cell into which the light and/or heavy chain genes of a single antibody have been transfected. Monoclonal antibodies are produced by methods known to those of skill in the art, for instance by making hybrid antibody-forming cells from a fusion of myeloma cells with immune spleen cells.

Monoclonal antibodies include humanized monoclonal antibodies.

A "chimeric antibody" has framework residues from one species, such as human, and CDRs (which generally confer antigen binding) from another species, such as a murine antibody that specifically binds a PD-1, PD-L1, CTLA-4, BTLA, TIM-3, LAG3 or 4-1BB polypeptide.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions, which have substantially no effect on antigen binding or other immunoglobulin functions. Humanized immunoglobulins can be constructed by means of genetic engineering (see for example, U.S. Pat. No. 5,585,089).

Andgen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

Andgen-presenting cell (APC): A cell that can present antigen bound to MHC class I or class II molecules to T cells. APCs include, but are not limited to, monocytes, macrophages, dendritic cells, B cells, T cells and Langerhans cells. A T cell that can present antigen to other T cells (including CD4+ and/or CD8+ T cells) is an antigen presenting T cell (T-APC).

B- and T-lymphocyte attenuator (BTLA): A protein also known as CD272. BTLA expression is induced during activation of T cells, and BTLA remains expressed on Th1 cells. BTLA interacts with a B7 homolog, B7H4, and plays a role in T-cell inhibition via interaction with tumor necrosis family receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses. A specific, non-limiting BTLA amino acid sequence, and an mRNA sequence encoding BTLA, is provided in GENBANK® Accession No. NM_001085357, Sep. 1, 2016, incorporated herein by reference. BTLA antagonists include agents that reduce the expression or activity of BTLA or inhibits the T-cell inhibition function of BTLA, for example, by specifically binding to BTLA and inhibiting binding of BTLA to tumor necrosis factor receptors. Exemplary compounds include antibodies (such as an anti-BTLA antibody), RNAi molecules, antisense molecules, and dominant negative proteins.

Binding or stable binding (olgonucleotide): An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional and physical binding assays. For instance, binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and the target disassociate from each other, or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. An antibody that "specifically binds" an antigen (such as a PD-1, PD-L1, CTLA-4, BTLA, TIM-3, LAG3 or 4-1BB polypeptide) is an antibody that binds the antigen with high affinity and does not significantly bind other unrelated antigens.

Cancer therapeutic: Any agent of use for treating cancer in a subject. Cancer therapeutics include a checkpoint inhibitor, biological response modifier (for example, cytokines and chemokines), a cancer vaccine, chemotherapy and/or radiation.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{rd}$ ed., © 2000 Churchill Livingstone, Inc; Baltzer, L., Berkery, R. (eds.): Oncology Pocket Guide to Chemotherapy, 2nd ed. St. Louis, Mosby-Year Book, 1995; Fischer, D. S., Knobf, M. F., Durivage, H J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds PD-1, PD-L1, or CTLA-4 polypeptide used in combination with cells, a radioactive compound, or a chemical compound.

CD39 (ENTPD1): An integral membrane protein with two transmembrane domains and a large extracellular region (Maliszewski et al, 1994). It was first identified as an activation marker on human lymphocytes and as the vascular ecto-ADPase (Kaczmarek E et al. (1996) Biol Chem). The term "CD39" denotes the CD39 protein also named as ectonucleoside triphosphate diphosphohydrolase-1 (ENTPD1). In vivo CD39 is expressed on regulatory T cells (Treg cells), B cells and several innate immune cells. It plays a key role in immune suppression via hydrolysis of adenosine triphosphate (ATP) and adenosine diphosphate (ADP) into adenosine monophosphate (AMP), which is then processed into adenosine by CD73, an ecto-5'-nucleotidase. Adenosine is a potent immunoregulator that, via binding to A2A receptors on T cells, enhances the accumulation of intracellular cAMP, thereby preventing T cell activation (Deaglio S et al., JEM, 2007). Expression of both, CD39 and CD73 is increased in several human solid malignancies (Antonioli Luca et al., Trends Mol Med, 2013). Upregulation of both enzymes is favored within hypoxic environments, and their sequential concerted action may play a role in tumor immunoescape (Eltzschig H K et al., Blood 2009; Ghiringhelli F et al., J Biomed Biotech, 2012). A specific, non-limiting CD39 amino acid sequence, and an mRNA sequence encoding CD39, is provided in GENBANK® Accession No. NM_001776, May 1, 2017, incorporated herein by reference.

CD103: Known as the integrin alpha E (ITGAE), CD103 binds integrin beta 7 (β7-ITGB7) to form the heterodimeric integrin molecule αEβ7. The main ligand for αEβ7 is E-cadherin, an adhesion molecule found on epithelial cells. It is important for T cell homing to the intestinal sites and retention of tissue-resident memory ($T_{RM}$) cells in tissues. In vivo, CD103 is expressed on a subset of dendritic cells in the gut and a population of T cells present on peripheral tissues characterized as tissue-resident memory cells ($T_{RM}$) (Schenkel J M et al., Immunity, 2014; Mueller S N et al., Nat Rev Immunol, 2015). CD103 is also expressed on a subset of CD8 T cells in high-grade serous ovarian cancer, lung cancer, urothelial cell carcinoma of the bladder and endometrial carcinoma (Webb J R et al., Clin Cancer Res, 2014; Webb J R et al., Cancer Immunol Res, 2015; Komdeur F L et al., Oncotarget, 2016; Djenidi F et al., J Immunol, 2015; Wang B et al., J Urol, 2015; Workel H H et al, EJC, 2015). In those malignancies, CD103+ CD8 T cells are preferentially localized within the tumor, therefore favoring a direct interaction with tumor cells. CD103+ CD8 T cells express high levels of PD-1, an activation/exhaustion surface molecule, which upon interaction with its ligand PD-L1 results in inhibition of T cell proliferation, survival and effector functions (Webb J R et al., Cancer Immunol Res, 2015). A specific, non-limiting CD103 amino acid sequence, and an mRNA sequence encoding CD103, is provided in GENBANK® Accession No. NM_002208, May 20, 2017, incorporated herein by reference.

Conservative variants: "Conservative" amino acid substitutions are those substitutions that do not substantially affect or decrease the affinity of a protein, such as an antibody. For example, a human antibody that specifically binds PD-1, PD-L1, BTLA, TIM-3, LAG3 CTLA-4 or 4-1BB, can include at most about 1, at most about 2, at most about 5, and most about 10, or at most about 15 conservative substitutions and specifically bind the PD-1, PD-L1, BTLA, TIM-3, LAG3, CTLA-4 or 4-1BB polypeptide. The term conservative variation also includes the use of a substituted amino acid in place of an unsubstituted parent amino acid, provided that antibody specifically binds the PD-1, PD-L1, BTLA, TIM-3, LAG3, CTLA-4 or 4-1BB polypeptide. Non-conservative substitutions are those that reduce an activity or binding to a PD-1, PD-L1, BTLA, TIM-3, LAG3, CTLA-4, or 4-1BB polypeptide.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form.

Control level (immune parameter): A baseline level of an immune parameter. In some embodiments, and control level is the level of a component of the immune system, such as a specific type of cells, in the absence of a therapeutic agent. A control level can be measured in a sample from a subject that has not been treated with an agent of interest, or a sample from a subject that has been treated with a control agent. The control level can also be a standard value, such as a value determined from an average of a large number of samples over time. The control level can also be measured in a sample from a subject treated with the specific dose of a therapeutic agent, wherein that dose is not administered to the subject at the time the subject is currently under evaluation. The control can be from the subject under evaluation, or can be from a different subject.

Cytotoxic T-lymphocyte-Associated Protein 4 (CTLA-4): A protein also known as CD152. CTLA-4 is a member of the immunoglobulin superfamily. CTLA-4 is a protein receptor that functions as an immune checkpoint, and thus downregulates immune responses. CTLA-4 is constitutively expressed in regulatory T cells (Tregs) and is upregulated in conventional T cells after activation. CLTA4 binds CD80 or CD86 on the surface of antigen-presenting cells, and is an inhibitor of T cells. Specific non-limiting examples of a CTLA-4 protein and an mRNA encoding CTLA-4 are disclosed, for example, in GENBANK® Accession No. NM_001037631, Oct. 7, 2016, incorporated herein by reference. CTLA-4 antagonists include agents that reduce the expression or activity of CTLA-4 or inhibits the T-cell inhibition function of CTLA-4, for example, by specifically binding to CTLA-4 and inhibiting binding of CTLA-4 to CD80 or CD86 on the surface of antigen-presenting cells. Exemplary compounds include antibodies (such as an anti-CTLA-4 antibody), RNAi molecules, antisense molecules, and dominant negative proteins.

Detecting or detection (cell or biomolecule): Refers to quantitatively or qualitatively determining the presence of a biomolecule or specific cell type, such as a $CD8^+CD39^+CD103^+$ T cell, under investigation. For example, quantitatively or qualitatively determining the presence of $CD8^+CD39^+CD103^+$ T cells in a sample from a subject. Generally, detection of a biological molecule, such as a protein, nucleic acid, or detecting a specific cell type or cell proliferation, requires performing a biological assay and not simple observation. For example, assays that utilize antibodies or nucleic acid probes (which can both be labeled), or can be used to detect proteins or cells, respectively. Diagnosing or diagnosis of the efficacy of treatment, such as with a checkpoint inhibitor, involves detecting a significant change in a cell or biomolecule, such as $CD8^+CD39^+CD103^+$ T cells.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule.

Diagnostic: Identifying the presence or nature of a pathologic condition, such as, but not limited to, a tumor. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as a tumor or metastasis.

Encode: A polynucleotide is said to encode a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Feeder Cells: A layer of cells such as on the bottom of a culture dish. The feeder cells can release nutrients, growth factors and/or cytokines into the culture medium and provide a substrate to which other cells, such as T cells, can interact. The cells can be irradiated. In one embodiment, feeder cells are irradiated allogeneic peripheral blood mononuclear cells.

Immune Checkpoint Inhibitor: A type of agent that blocks biological pathways in specific types of immune system cells, such as, but no limited to, T cells, and some cancer cells. These inhibitors inhibit T cells from killing cancer cells. When a checkpoint inhibitor is blocked, an "inhibition" on the immune system is reduced and T cells become activated against cancer cells. Examples of checkpoint proteins found on T cells or cancer cells include PD-1, PD-L1, CTLA-4, BTLA, TIM-3.

Immune Response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

"Unresponsiveness" with regard to immune cells includes refractivity of immune cells to stimulation, such as stimulation via an activating receptor or a cytokine. Unresponsiveness can occur, for example, because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production (such as IL-2). T cell anergy occurs when T cells are exposed to antigen and receive a first signal (a T cell receptor or CD3 mediated signal) in the absence of a second signal (a costimulatory signal). Under these conditions, re-exposure of the cells to the same antigen (even if exposure occurs in the presence of a costimulatory molecule) results in failure to produce cytokines and, thus, failure to proliferate. Anergic T cells can, however, mount responses to unrelated antigens and can proliferate if cultured with cytokines (such as IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the API sequence that can be found within the enhancer (Kang et al. Science 257:1134, 1992). Anergic antigen specific T cells may have a reduction of at least 10%, 20%, 30%, 40%, 50%, 60%, 70%, 80%, 90%, 95%, or even 100% in cytotoxic activity relative a corresponding control antigen specific T cell.

Inhibiting or treating a disease: Inhibiting a disease, such as tumor growth, refers to inhibiting the full development of a disease or lessening the physiological effects of the disease process. In several examples, inhibiting or treating a disease refers to lessening symptoms of a tumor or an infection with a pathogen. For example, cancer treatment can prevent the development of paraneoplastic syndrome in a person who is known to have a cancer, or lessening a sign or symptom of the tumor. In another embodiment, treatment of an infection can refer to inhibiting development or lessening a symptom of the infection. "Treatment" refers to a therapeutic intervention that ameliorates a sign or symptom of a disease or pathological condition related to the disease. Therapeutic vaccination refers to administration of an agent to a subject already infected with a pathogen. The subject can be asymptomatic, so that the treatment prevents the development of a symptom.

Isolated: An "isolated" biological component, such as a nucleic acid, protein (including antibodies) or cell, has been substantially separated or purified away from other biological components in the environment (such as other cells) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Lymphocyte: A type of white blood cell that is involved in the immune defenses of the body. There are two main types of lymphocytes: B cells and T cells.

Lymphocyte-activation gene 3 (LAG3): A protein which in humans is encoded by the LAG3 gene, also called CD223. LAG-3 is a cell surface molecule with diverse biologic effects on T cell function, and is an immune checkpoint receptor. LAG3 negatively regulates cellular proliferation, activation, and homeostasis of T cells, and has been reported to play a role in Treg suppressive function. An exemplary amino acid and mRNA encoding human LAG3 is provided in GENBANK® Accession No. NM_002286.5, Apr. 9, 2017, incorporated herein by reference.

Mammal: This term includes both human and non-human mammals. Similarly, the term "subject" includes both human and veterinary subjects.

Mean Fluorescence Intensity (flow cytometry): Flow cytometry is concerned with the measurement of the light intensity of a cell or particle, whether it be scattered laser light or fluorescence emitted by a fluorochrome. Light is detected by a photomultiplier tube (PMT), which converts it via an amplifier to a voltage that is proportional to the original fluorescence intensity and the voltage on the PMT. These voltages, which are a continuous distribution, are converted to a discrete distribution by an Analog to Digital converter (ADC), which places each signal into a specific channel depending on the level of fluorescence. The greater the resolution of the ADC, the closer this reflects the continuous distribution.

Flow cytometric data can be displayed using either a linear or a logarithmic scale. The use of a logarithmic scale is indicated in most biological situations where distributions are skewed to the right. In this case the effect is to normalize the distribution—it is said to be Log Normal and the data has been log-transformed. Linear signals come through a linear amplifier but the logarithmic transformation may be achieved either by a logarithmic amplifier or by the use of Look Up Tables (LUT). Most ADCs in analytical cytometers are 10-bit, i.e., they divide data into 2e10 or 1024 channels, although there is a growing trend to use 12- or 14-bit ADCs to give greater resolution of data.

Data from a single data channel (scatter or fluorescence) is displayed as a histogram in which the x axis is divided into 1024 channels (for a 10-bit ADC). If the data is in a linear scale, the channel number and the linear value for that channel will be easily obtained. On a logarithmic scale, the x axis is still divided into 1024 channels but is displayed as a 5-log decade scale (in general 5 log decades are used).

To quantify flow cytometric data the measures of the distribution of a population are utilized. Generally, the measures of central tendency are the mean and the median. The mean is the 'average' and can be either arithmetic or geometric. The arithmetic mean is calculated as Sigma(x)/n, and the geometric mean as n root(a1×a2×a3 . . . an). In general, with log-amplified data the geometric mean is used as it takes into account the weighting of the data distribution, and the arithmetic mean is used for linear data or data displayed on a linear scale. The median is the central value, i.e., the 50th percentile, where half the values are above and half below. A cell with "high" expression and "low" expression can be determined relatively depending on the fluorescence of the entire population; these parameters are readily visualized on plots of flow cytometric data.

Medium (tissue culture or cell culture): A synthetic set of culture conditions with the nutrients necessary to support the growth (cell proliferation/expansion) of a specific population of cells. Media generally include a carbon source, a nitrogen source and a buffer to maintain pH. In one embodiment, growth medium contains a minimal essential media, such as RPMI, supplemented with various nutrients to enhance cell growth. Additionally, the minimal essential media may be supplemented with additives such as human, calf or fetal bovine serum.

Neoplasia, malignancy, cancer or tumor: A neoplasm is an abnormal growth of tissue or cells that results from excessive cell division. Neoplastic growth can produce a tumor. A "cancer" or "tumor" is a neoplasm that has undergone characteristic anaplasia with loss of differentiation, increase rate of growth, invasion of surrounding tissue, and is capable of metastasis. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Metastatic cancer is a cancer at one or more sites in the body other than the site of origin of the original (primary) cancer from which the metastatic cancer is derived.

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In several examples, a tumor is a head and neck squamous cell carcinoma, lung cancer, melanoma, ovarian cancer renal cell carcinoma, bladder cancer, cervical cancer, liver cancer, prostate cancer, breast cancer, glioblastoma or rectal cancer.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, intraarticularly, or subcutaneously, and various surface applications including intranasal, intradermal, and topical application, for instance.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (e.g., glycosylation or phosphorylation). A polypeptide can be between 3 and 30 amino acids in length. In one embodiment, a polypeptide is from about 7 to about 25 amino acids in length. In yet another embodiment, a polypeptide is from about 8 to about 10 amino acids in length. In yet another embodiment, a peptide is about 9 amino acids in length. With regard to polypeptides, "comprises" indicates that additional amino acid sequence or other molecules can be included in the molecule, "consists essentially of" indicates that additional amino acid sequences are not included in the molecule, but that other agents (such as labels or chemical compounds) can be included, and "consists of" indicates that additional amino acid sequences and additional agents are not included in the molecule.

Preventing, treating or ameliorating a disease: "Preventing" a disease refers to inhibiting the full development of a disease, such as a tumor. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Programmed cell Death protein (PD)-1: PD-1 molecules are members of the immunoglobulin gene superfamily. The human PD-1 has an extracellular region containing an immunoglobulin superfamily domain, a transmembrane domain, and an intracellular region including an immunoreceptor tyrosine-based inhibitory motif (ITIM) ((Ishida et al., EMBO J. 11:3887, 1992; Shinohara et al., *Genomics* 23:704, 1994; U.S. Pat. No. 5,698,520, incorporated herein by reference). These features also define a larger family of molecules, called the immunoinhibitory receptors, which also includes gp49B, PIR-B, and the killer inhibitory receptors (KIRs) (Vivier and Daeron (1997) Immunol. Today 18:286). Without being bound by theory, it is believed that the tyrosyl phosphorylated ITIM motif of these receptors interacts with the S112-domain containing phosphatase, which leads to inhibitory signals. A subset of these immunoinhibitory receptors bind to major histocompatibility complex (MHC) molecules, such as the KIRs, and cytotoxic T-lymphocyte associated protein 4 (CTLA-4) binds to B7-1 and B7-2. In humans, PD-1 is a 50-55 kDa type I transmembrane receptor that was originally identified in a T cell line undergoing activation-induced apoptosis. PD-1 is expressed on T cells, B cells, and macrophages. The ligands for PD-1 are the B7 family members PD-ligand 1 (PD-L1, also known as B7-H1) and PD-L2 (also known as B7-DC).

In vivo, PD-1 is expressed on activated T cells, B cells, and monocytes. Experimental data implicates the interactions of PD-1 with its ligands in down regulation of central and peripheral immune responses. In particular, proliferation in wild-type T cells but not in PD-1-deficient T cells is inhibited in the presence of PD-L1. Additionally, PD-1-deficient mice exhibit an autoimmune phenotype. An exemplary amino acid sequence of human PD-1 is set forth in Ishida et al., EMBO J. 11:3887, 1992; Shinohara et al. Genomics 23:704, 1994; U.S. Pat. No. 5,698,520):

Engagement of PD-1 (for example by crosslinking or by aggregation), leads to the transmission of an inhibitory signal in an immune cell, resulting in a reduction of immune responses concomitant with an increase in immune cell anergy. PD-1 binds two ligands, PD-L1 and PD-L2, both of which are human PD-1 ligand polypeptides, that are members of the B7 family of polypeptides.

PD-1 antagonists include agents that reduce the expression or activity of a PD ligand 1 (PD-L1) or a PD ligand 2 (PD-L2) or reduces the interactions between PD-1 and PD-L1, or PD-L2. Exemplary compounds include antibodies (such as an anti-PD-1 antibody, an anti-PD-L1 antibody, and an anti-PD-L2 antibody), RNAi molecules (such as anti-PD-1 RNAi molecules, anti-PD-L1 RNAi, and an anti-PD-L2 RNAi), antisense molecules (such as an anti-PD-1 antisense RNA, an anti-PD-L1 antisense RNA, and an anti-PD-L2 antisense RNA), dominant negative proteins (such as a dominant negative PD-1 protein, a dominant negative PD-L1 protein, and a dominant negative PD-L2 protein), see, for example, PCT Publication No. 2008/083174, incorporated herein by reference.

Proliferation: The division of a cell to produce progeny, which can be measured in a number of ways known in the art. This includes, but is not limited to, assays that count the total number of cells, assays that count the number of cells of a specific cell type, Ki-67 assays, thymidine incorporation, and bromodeoxyuridine assays.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Sample (Biological sample): Includes biological samples containing fluids, tissues, cells, and subcomponents thereof, such as DNA, RNA, and proteins. For example, common samples include tumor biopsy, bone marrow, spleen, lymph node, blood, e.g., peripheral blood (but can also include any other source from which $CD8^+CD39^+CD103^+$ T cells can be isolated, including: tissue biopsy, surgical specimens, fine needle aspirates, autopsy material, and the like).

Specific binding agent: An agent that binds substantially only to a defined target. In one embodiment, the specific binding agent is a monoclonal or polyclonal antibody that specifically binds a PD-1, PD-L1, CTLA-4, BTLA, TIM-3, LAG3 or 4-1BB polypeptide The term "specifically binds" refers, with respect to an antigen such as PD-1, PD-L1, CTLA-4, BTLA, TIM-3, LAG3 or 4-1BB polypeptide to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. Specific binding results in a much stronger association between the antibody (or other ligand) and cells bearing the antigen than between the antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Subject: Living multi-cellular vertebrate organisms, a category that includes both human and veterinary subjects, including human and non-human mammals.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8+ T cell is a cytotoxic T lymphocyte. In another embodiment, a CD8+ cell is a suppressor T cell. A T cell is "activated" when it can respond to a specific antigen of interest presented on an antigen presenting cells.

T-cell immunoglobulin and mucin-domain containing-3 (TIM-3): A protein that in humans is encoded by the HAVCR2 gene. TIM3 is an immune checkpoint that is a Th1-specific cell surface protein that regulates macrophage activation and enhances the severity of experimental autoimmune encephalomyelitis in mice. The Tim-3 pathway can interact with the PD-1 pathway in the exhausted CD8+ T cells in cancer. An exemplary mRNA and protein sequence for human TIM-3 is provided in GENBANK® Accession No. NM_032782.4, Apr. 30, 2017, incorporated herein by reference.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A, and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below.

All publications, patent applications, patents, and other references mentioned herein are incorporated by reference in their entirety. All GENBANK® Accession numbers are herein incorporated by reference as they appear in the database on Jun. 1, 2017. In case of conflict, the present specification, including explanations of terms, will control. In addition, the materials, methods, and examples are illustrative only and not intended to be limiting.

Methods of Treatment: Adoptive Immunotherapy

Methods are disclosed herein for the treatment of a subject of interest, such as a subject with a tumor. The methods include the administration of a therapeutically effective amount of $CD8^+CD39^+CD103^+$ T cells. Methods are disclosed herein for increasing the immune response, such as enhancing the immune system in a subject. Administration of the purified $CD8^+CD39^+CD103^+$ T cells, as disclosed herein, will increase the ability of a subject to elicit an immune response, such as to a tumor. Therefore, by purifying and generating a purified population of selected $CD8^+CD39^+CD103+$ T cells from a subject ex vivo and introducing a therapeutic amount of these cells, the immune response of the recipient subject is enhanced. Additional agents can also be administered to the subject, as discussed below. The subject can be a human or a veterinary subject.

In one example, the method includes isolating from the donor a population of donor cells including $CD8^+CD39^+CD103^+$ T cells (such as peripheral blood mononuclear cells or T cells from a tumor biopsy), and optionally expanding the cells. A therapeutically effective amount of $CD8^+CD39^+CD103^+$ T cells is administered to the recipient, thereby producing an immune response to the tumor in the recipient. Such $CD8^+CD39^+CD103^+$ T cells can kill cells containing the tumor-associated antigen or assist other immune cells. In some embodiments, additional cancer therapeutics, such as chemotherapeutic agents, can be administered.

In several embodiments the method also includes administering a therapeutically effective amount of a PD-1 antagonist, PD-L1 antagonist, CTLA-4 antagonist, BTLA antagonist, TIM-3 antagonist, LAG3 antagonist and/or a 4-1BB agonist to the subject. The administration of a PD-1 antagonist, PD-L1 antagonist, CTLA-4 antagonist, BTLA antagonist, TIM-3 antagonist, LAG3 antagonist and/or a 4-1BB agonist is described in detail below. Administration of a therapeutic amount of $CD8^+CD39^+CD103^+$ T cells and a therapeutically effective amount of a PD-1 antagonist, PD-L1 antagonist, CTLA-4 antagonist, BTLA antagonist, TIM-3 antagonist, LAG3 antagonist and/or a 4-1BB agonist can be used prophylactically to prevent recurrence of the tumor in the recipient, or to treat a relapse of the tumor.

Generally, the $CD8^+CD39^+CD103^+$ T cells are autologous. However, the $CD8^+CD39^+CD103^+$ T cells can also react to matched MHCs from allogeneic donors. Generally, the T cells are positive for expression of CD3, CD8, CD39, and CD103. For example, fluorescence activated cell sorting (FACS) can be used to identify (and sort if desired) populations of cells that are positive for CD3, CD8, CD39 and CD103 by using differently colored anti-CD3, anti-CD8, anti-CD39 and anti-CD103 antibodies. Briefly, a population of cells, such as peripheral blood mononuclear cells or T cells from a tumor biopsy are incubated in the presence of anti-CD103, anti-CD8, anti-CD39 and optionally anti-CD3 antibodies (each having a different fluorophore attached), for a time sufficient for the antibody to bind to the cells. After removing unbound antibody, cells are analyzed by FACS using routine methods. In specific examples, the resulting population of $CD8^+CD39^+CD103^+$ T cells is at least 30% pure relative to the total population of CD8+ positive cells, such as at least about 50% pure, at least about 60% pure, at least about 70% pure, at least about 80% pure, at least about 90% pure, at least about 95% pure, or at least about 96%, about 97%, about 98% or about 99% pure relative to the total population of CD8 positive cells. Thus, only a limited number of heterologous cells is administered. The cells can be processed for more than one round of cell sorting. Populations of T cells can be tested for *mycoplasma*, sterility, endotoxin and quality controlled for function and purity prior cryopreservation or prior to infusion into the recipient.

In one embodiment, labeled antibodies specifically directed to one or more cell surface markers are used to identify, quantify, and/or isolate $CD8^+CD39^+CD103^+$ T cells and populations of these cells that express additional markers. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P., *Handbook of Fluorescent Probes and Research Products*, published by Molecular Probes, 9$^{th}$ Edition (2002). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazolone, and nitrophenol. The radioactive compounds that can be conjugated or incorporated into the antibodies are known to the art, and include, but are not limited to, technetium 99 ($^{99}$Tc), $^{125}$I, and amino acids comprising any radionuclides, including, but not limited to, $^{14}$C, $^{3}$H and $^{35}$S.

In some examples, $CD8^+CD39^+CD103^+$ T cells are isolated by contacting the cells from a biological sample, such as a peripheral blood sample or a tumor sample, with an appropriately labeled antibody. However, other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

The data generated by flow-cytometers can be plotted in a single dimension, to produce a histogram, or in two-dimensional dot plots or even in three dimensions. The regions on these plots can be sequentially separated, based on fluorescence intensity, by creating a series of subset extractions, termed "gates." Specific gating protocols are known in the art. The plots are generally made on logarithmic scales. Because different fluorescent dyes' emission spectra overlap, signals at the detectors are compensated electronically and computationally. Data accumulated using the flow cytometer can be analyzed using software such as FLOWJO® or BD FACSDiva®. The analysis is most often done on a separate computer. The principles of gating, which allow the identification of cells that express high or low levels of a protein of interest, are well known in the art. Tutorials for learning to establish gates are provided, for example, and the FLOWJO® website. Generally, one of skill in the art can readily use any FACS machine and computer programs for data analysis to establish gates to separate cells that express a particular marker. As an example, one of skill in the art can readily identify cells wherein expression of CD8 is absent (CD8-), expression of CD8 is present (CD8+).

Additional separation procedures may include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic Petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system. The selection of appropriate conditions, however, is well known in the art.

Unbound cells then can be eluted or washed away with physiologic buffer after sufficient time has been allowed for the cells expressing a marker of interest (such as, but not limited to, CD8, CD39, CD103, and optionally CD3, to bind to the solid-phase linked antibodies. The bound cells are then separated from the solid phase by any appropriate method, depending mainly upon the nature of the solid phase and the antibody employed, and quantified using methods well known in the art. In one specific, non-limiting example, bound cells separated from the solid phase are quantified by FACS (see above).

Antibodies may be conjugated to biotin, which then can be removed with avidin or streptavidin bound to a support, or fluorochromes, which can be used with FACS to enable cell separation and quantitation, as known in the art.

In another embodiment, an apheresis procedure employing an automated apheresis instrument (such as the CS-3000 blood cell separator, Baxter Health Care, Deerfield, Ill., or equivalent machine) can be used to collect cells from a subject. In a specific, non-limiting example, labeled antibodies specifically directed to one or more cell surface markers are used to identify and quantify the $CD8^+CD39^+CD103^+$ T cells such as the cells disclosed herein.

In some embodiments, the $CD8^+CD39^+CD103^+$ T cells are expanded in vitro prior to administration to the subject. Expansion methods are disclosed below.

The present disclosure also provides therapeutic compositions that include the enriched (such as purified) $CD8^+CD39^+CD103^+$ T cells and optionally a PD-1 antagonist, PD-L1 antagonist, CTLA-4 antagonist, BTLA antagonist, TIM-3 antagonist, LAG3 antagonist and/or a 4-1BB agonist. The compositions are of use in the methods disclosed herein, such as, but not limited to, treatment of a subject with a tumor. In particular examples, a population of $CD8^+CD39^+CD103^+$ T cells are placed in a therapeutic dose form for administration to a subject in need of them. The PD-1 antagonist, PD-L1 antagonist, CTLA-4 antagonist, BTLA antagonist, TIM-3 antagonist, LAG3 antagonist and/or a 4-1BB agonist is also present in a therapeutic dose form for administration to a subject in need of treatment.

A therapeutically effective amount of $CD8^+CD39^+CD103^+$ T cells is administered to the subject. Specific, non-limiting examples of a therapeutically effective amount of $CD8^+CD39^+CD103^+$ T cells include purified $CD8^+CD39^+CD103^+$ T cells administered at a dose of about $1\times10^5$ cells per kilogram of subject to about $1\times10^9$ cells per kilogram of subject, such as from about $1\times10^6$ cells per kilogram to about $1\times10^8$ cells per kilogram, such as from about $5\times10^6$ cells per kilogram to about $75\times10^6$ cells per kilogram, such as at about $25\times10^6$ cells per kilogram, or at about $50\times10^6$ cells per kilogram.

Purified $CD8^+CD39^+CD103^+$ T cells can be administered in single or multiple doses as determined by a clinician. For example, the cells can be administered at intervals of approximately one day, two days, three days, four days, five days, six days, one week, two weeks or monthly depending on the response desired and the response obtained. In some examples, once the desired response is obtained, no further CD8$^+$CD39$^+$CD103$^+$ T cells are administered. However, if the recipient displays one or more symptoms associated with the tumor, a therapeutically effective amount of CD8$^+$CD39$^+$CD103$^+$ T cells can be administered at that time.

The administration can be local or systemic. In some embodiments, the cells are administered intravenously after the subject is treated in chemotherapy. In other embodiments the subject is also administered cytokines, such as IL-2 and/or IL-15, to support proliferation of the administered cells.

The purified CD8$^+$CD39$^+$CD103$^+$ T cells disclosed herein can be administered with a pharmaceutically acceptable carrier, such as saline. The PD-1 antagonist, PD-L1 antagonist, CTLA-4 antagonist, BTLA antagonist, TIM-3 antagonist, LAG3 antagonist and/or a 4-1BB agonist can also be formulated in a pharmaceutically acceptable carrier, as described below. These can be formulated in a single composition, or in two separate compositions. In some examples, other therapeutic agents are administered with the T cells. Other therapeutic agents can be administered before, during, or after administration of the CD8$^+$CD39$^+$CD103$^+$ T cells, depending on the desired effect. Exemplary therapeutic agents include, but are not limited to, anti-microbial agents, immune stimulants such as interferon-alpha, chemotherapeutic agents or peptide vaccines used to stimulate T cells in vitro. In a particular example, compositions containing CD8$^+$CD39$^+$CD103$^+$ T cells also include the one or more therapeutic agents. The use of CD8$^+$CD39$^+$CD103$^+$ T cells can reduce tumor volume, tumor metastasis, tumor reoccurrence, Generally, the methods include selecting a subject having a tumor, such as a benign or malignant tumor, and administering to the subject a therapeutically effective amount of (1) CD8$^+$CD39$^+$CD103$^+$ T cells and (2) optionally a checkpoint inhibitor antagonist, such as a PD-1 antagonist, a PD-L1 antagonist, a BTLA antagonist, a TIM-3 antagonist, a LAG3 antagonist, or a CTLA-4 antagonist, or a 4-1BB agonist. The PD-1 antagonist, PD-L1 antagonist, BTLA antagonist, TIM-3 antagonist, LAG3 antagonist or CTLA-4 antagonist, or the 4-1BB agonist, can, in some non-limiting examples, be an antibody (or antigen binding fragment thereof) that specifically binds PD-1, PD-L1, PD-L1, PD-L2, TIM-3, LAG3, BTLA, CTLA-4, or 4-1BB, respectively. The CD8$^+$CD39$^+$CD103$^+$ T cells are of use for treating the tumor, such as for reducing tumor volume, reducing or preventing metastasis, preventing the conversion of a benign to a malignant tumor and/or preventing or inhibiting reoccurrence of the tumor. The administration can be local or systemic. Suitable administration methods are known to a clinician.

In some embodiments, an advantage of the methods provided herein is that the combination of CD8$^+$CD39$^+$CD103$^+$ T cells with checkpoint inhibitors such as a PD-1 antagonist, PD-L1 antagonist, BTLA antagonist, TIM-3 antagonist, LAG3 antagonist and/or a CTLA-4 antagonist, or a 4-1BB agonist, allows for reduced dosage of active agents for cancer therapy, while also reducing any corresponding undesired side-effects (such as cytotoxicity) of the therapy. In further embodiments, another advantage of the methods provided herein is that the combination of CD8$^+$CD39$^+$CD103$^+$ T cells with checkpoint inhibitors such as a PD-1 antagonist, PD-L1 antagonist, BTLA antagonist, TIM-3 antagonist, LAG3 antagonist and/or a CTLA-4 antagonist, or with a 4-1BB agonist, for treating the tumor, such as for reducing tumor volume, reducing or preventing metastasis, preventing the conversion of a benign to a malignant tumor and/or preventing or inhibiting reoccurrence of the tumor. In additional embodiments, the combination of CD8$^+$CD39$^+$CD103$^+$ T cells with checkpoint inhibitors such as a PD-1 antagonist, PD-L1 antagonist, BTLA antagonist, TIM-3 antagonist, LAG3 antagonist and/or a CTLA-4 antagonist, or a 4-1BB agonist allows for increased survival.

Additional agents can also be administered to the subject of interest, such as, but not limited to, cancer therapeutics. Additional treatments can also be administered to the subject, such as, but not limited to, surgical resection of the tumor.

The subject can be selected for treatment. For example, a diagnostic assay (such as an immunohistochemical (IHC) assay can be performed on the tumor (or a sample on the tumor) to identify the subject as one likely to respond to the disclosed method of treatment. Methods of selection are disclosed below.

In further embodiments, the subject is selected for treatment if the tumor tests positive for PD-L1 or PD-L2 expression by an IHC assay. Exemplary assays for detecting a tumor that tests positive for PD-L1 expression are provided in Topalian et al. 2012. Safety, activity, and immune correlates of anti-PD-1 antibody in cancer. N. Engl. J. Med. 366:2443-2454; Wolchok et al. 2013. Nivolumab plus ipilimumab in advanced melanoma. N. Engl. J. Med. 369:122-133; Herbst et al. 2014. Predictive correlates of response to the anti-PD-L1 antibody MPDL3280A in cancer patients. Nature. 515:563-567; Garon et al. 2015. Pembrolizumab for the treatment of non-small-cell lung cancer. N. Engl. J. Med. 372:2018-2028; and Reck et al. Pembrolizumab versus chemotherapy for PD-L-positive non-small-cell lung cancer. N. Engl. J. Med. 375:1823-1833, each of which is incorporated by reference herein.

The tumor can be benign or malignant. The tumor can be any tumor of interest, including, but not limited to, a head and neck squamous cell carcinoma, lung cancer, melanoma, ovarian cancer renal cell carcinoma, bladder cancer, cervical cancer, liver cancer, prostate cancer, breast cancer, glioblastoma or rectal cancer. The lung cancer can be small cell or non-small cell carcinoma of the lung. The liver cancer can be a hepatic carcinoma. The breast cancer can be triple negative breast cancer. In some embodiments, the tumor is a head and neck tumor, such as tumors of the nasal cavity, paranasal sinuses, nasopharynx, oral cavity, oropharynx, larynx, hypopharynx, salivary glands and paragangliomas. Additional examples are skin tumors, brain tumors, cervical carcinomas, testicular carcinomas, gastrointestinal tract tumors, genitourinary system tumors, gynecological system tumors, endocrine system tumors, a sarcoma of the soft tissue and bone, a mesothelioma, a melanoma, a neoplasm of the central nervous system, or a leukemia. In other embodiments, the tumor is a lung tumor, such as a non-small cell lung cancer or a small cell lung cancer. In further embodiments, the tumor can be a tumor of the gastrointestinal tract, such as cancer of the esophagus, stomach, pancreas, liver, biliary tree, small intestine, colon, rectum and anal region. In yet other embodiments, the tumor can be a tumor of the genitourinary system, such as cancer of the kidney, urethra, bladder, prostate, urethra, penis and testis. In some embodiments, the tumor is a gynecologic tumor, such as cancer of the cervix, vagina, vulva, uterine body, gestational trophoblastic diseases, ovarian, fallopian tube, peritoneal, or breast. In other embodiments, the tumor is an endocrine system tumor, such as a thyroid tumor, parathyroid tumor, adrenal cortex tumor, pancreatic endocrine tumor, carcinoid tumor and carcinoid syndrome. The tumor can be a sarcoma of the soft tissue and bone, a mesothelioma, a cancer of the skin, a melanoma, comprising cutaneous melanomas and intraocular melanomas, a neoplasm of the central nervous system, a cancer of the childhood, comprising retinoblastoma, Wilm's tumor, neurofibromatoses, neuroblastoma, Ewing's sarcoma family of tumors, rhabdomyosarcoma. The tumor can be a lymphoma, comprising non-Hodgkin's lymphomas, cutaneous T-cell lymphomas, primary central nervous system lymphoma, and Hodgkin's disease. The tumor can be a leukemia, such as acute leukemia, chronic myelogenous leukemia and lymphocytic leukemia. The tumor can be plasma cell neoplasms, a cancer of unknown primary site, a peritoneal carcinomastosis, a Kaposi's sarcoma, AIDS-associated lymphomas, AIDS-associated primary central nervous system lymphoma, AIDS-associated Hodgkin's disease and AIDS-associated anogenital cancers, a metastatic cancer to the liver, metastatic cancer to the bone, malignant pleural and pericardial effusions and malignant ascites.

In some embodiments, treatment of the tumor is initiated after the diagnosis of the tumor, or after the initiation of a precursor condition (such as dysplasia or development of a benign tumor). Treatment can be initiated at the early stages of cancer, for instance, can be initiated before a subject manifests symptoms of a condition, such as during a stage I diagnosis or at the time dysplasia is diagnosed or an in situ proliferative condition is diagnosed. However, treatment can be initiated during any stage of the disease, such as but not limited to stage I, stage II, stage III and stage IV cancers. In some examples, treatment is administered to these subjects with a benign tumor that can convert into a malignant or even metastatic tumor.

Treatment prior to the development of the condition, such as treatment upon detecting dysplasia or an early (benign) precursor condition, is referred to herein as treatment of a subject that is "at risk" of developing the condition. In some embodiments, administration of a composition can be performed during or after the occurrence of the conditions described herein. The compositions can be administered to a subject at risk of developing the tumor.

The presence of a tumor can be determined by methods known in the art, and typically include cytological and morphological evaluation. The tumor can be an established tumor. The cells can be in vivo or ex vivo, including cells obtained from a biopsy.

Treatment initiated after the development of a condition, such as malignant cancer, may result in decreasing the severity of the symptoms of one of the conditions, or completely removing the symptoms, or reducing metastasis, tumor volume or number of tumors. In some example, the tumor becomes undetectable following treatment.

In one aspect of the disclosure, the formation of tumors, such as metastasis, is delayed, prevented or decreased. In another aspect, the size of the primary tumor is decreased. In a further aspect, a symptom of the tumor is decreased. In yet another aspect, tumor volume is decreased. In yet another aspect reoccurrence of the tumor is delayed or prevented, such as for 1, 2, 3, 4, 5, 6, 7, 8, 9, 10, 11, 12, 13, 14, 15, 16, 17, 18, 19, 20, 2, 22, 23, or 24 months, or for 1, 2, 3, 4, 5, 6, 7, 8, 9, or 10 years.

In some embodiments immune response can be measured, tumor volume can be measured, the number of metastatic lesions can be measured, and/or a symptom of a tumor can be measured. A therapeutically effective dose can increase the immune response, decrease tumor volume, decrease the number and/or size of metastases, and/or decrease one or more symptoms of the tumor.

While the disclosed methods and compositions will typically be used to treat human subjects they may also be used to treat similar or identical diseases in other vertebrates, such as other primates, dogs, cats, horses, and cows. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988. The dosage form of the pharmaceutical composition will be determined by the mode of administration chosen.

$CD8^+CD39^+CD103^+$ T cells can be administered locally or systemically, by any route. For example, $CD8^+CD39^+CD103^+$ T cells can be administered intratumorally, intraperitoneally, intravenously. In one non-limiting example, the $CD8^+CD39^+CD103^+$ T cells can be administered intravenously. A PD-1, PD-L1, PD-L2, BTLA, TIM-3, LAG3, or CTLA-4 antagonist (or a 4-1BB agonist) also can be administered by any route, including parenteral administration, for example, intravenous, intraperitoneal, intramuscular, intraperitoneal, intrasternal, or intraarticular injection or infusion, or by sublingual, oral, topical, intranasal, or transmucosal administration, or by pulmonary inhalation. In some embodiments, the $CD8^+CD39^+CD103^+$ T cells and/or the PD-1, PD-L1, PD-L2, BTLA, TIM-3, LAG3, or CTLA-4 antagonist are administered to a tissue wherein the tumor is located, or directly into the tumor (intratumoral). When a parenteral composition is provided, e.g. for injection or infusion, active agents are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate-acetic acid buffers. A form of repository or "depot" slow release preparation may be used so that therapeutically effective amounts of the preparation are delivered into the bloodstream over many hours or days following transdermal injection or delivery.

In certain embodiments, the PD-1, PD-L1, PD-L2, BTLA, TIM-3, LAG3, or CTLA-4 antagonist (such as, but not limited to, an antibody or antigen binding fragment), or the 4-1BB agonist can be administered at a dose in the range of from about 0.01-10 mg/kg, 0.01-5 mg/kg, 0.01-1 mg/kg, 0.01-0.1 mg/kg, 1-10 mg/kg, 1-5 mg/kg, 1-3 mg/kg, 0.5-1.0 mg/kg, 0.05-0.5 mg/kg, according to a dosing schedule of administration including without limitation daily, 2 or 3 times per week, weekly, every 2 weeks, every 3 weeks, monthly, etc., or other dose and dosing schedule deemed appropriate by the treating physician. As part of the combination therapy, the $CD8^+CD39^+CD103^+$ T cells can be administered to the subject before, after, or concurrent with the additional agent, as long as the administration schedule provides for a sufficient physiological concentrations of the agents to provide a therapeutic benefit.

In some embodiments, the PD-1 or PD-L1 antagonist (such as an antibody or antigen binding fragment that specifically binds to PD-1 or PD-L1) can be administered at a dose in the range of from about 0.01-10 mg/kg, 0.01-5 mg/kg, 0.01-1 mg/kg, 0.01-0.1 mg/kg, 1-10 mg/kg, 1-5 mg/kg, 1-3 mg/kg, 0.5-1.0 mg/kg, 0.05-0.5 mg/kg, according to a dosing schedule of administration including without limitation daily, 2 or 3 times per week, weekly, every 2 weeks, every 3 weeks, monthly, etc., or other dose and dosing schedule deemed appropriate by the treating physician. As part of the combination therapy, the CD8$^+$CD39$^+$CD103$^+$ T cells can be administered to the subject before, after, or concurrent to the PD-1 or PD-L1 antagonist, as long as the administration schedule provides for a sufficient physiological concentrations of the agents to provide a therapeutic benefit. In certain embodiments, the CTLA-4 antagonist (such as an antibody or antigen binding fragment that specifically binds to CTLA-4) can be administered at a dose in the range of from about 0.01-10 mg/kg, 0.01-5 mg/kg, 0.01-1 mg/kg, 0.01-0.1 mg/kg, 1-10 mg/kg, 1-5 mg/kg, 1-3 mg/kg, 0.5-1.0 mg/kg, 0.05-0.5 mg/kg, according to a dosing schedule of administration including without limitation daily, 2 or 3 times per week, weekly, every 2 weeks, every 3 weeks, monthly, etc., or other dose and dosing schedule deemed appropriate by the treating physician. As part of the combination therapy, the CD8$^+$CD39$^+$CD103$^+$ T cells can be administered to the subject before, after, or concurrent to the CTLA-4 antagonist, as long as the administration schedule provides for a sufficient physiological concentrations of the agents to provide a therapeutic benefit. In further embodiments, the BTLA antagonist (such as an antibody or antigen binding fragment that specifically binds to BTLA) can be administered at a dose in the range of from about 0.01-10 mg/kg, 0.01-5 mg/kg, 0.01-1 mg/kg, 0.01-0.1 mg/kg, 1-10 mg/kg, 1-5 mg/kg, 1-3 mg/kg, 0.5-1.0 mg/kg, 0.05-0.5 mg/kg, according to a dosing schedule of administration including without limitation daily, 2 or 3 times per week, weekly, every 2 weeks, every 3 weeks, monthly, etc., or other dose and dosing schedule deemed appropriate by the treating physician. As part of the combination therapy, the CD8$^+$CD39$^+$CD103$^+$ T cells can be administered to the subject before, after, or concurrent to the BTLA antagonist, as long as the administration schedule provides for a sufficient physiological concentrations of the agents to provide a therapeutic benefit. In additional embodiments, the LAG3 or TIM-3 antagonist (such as an antibody or antigen binding fragment that specifically binds to LAG3 or TIM-3) can be administered at a dose in the range of from about 0.01-10 mg/kg, 0.01-5 mg/kg, 0.01-1 mg/kg, 0.01-0.1 mg/kg, 1-10 mg/kg, 1-5 mg/kg, 1-3 mg/kg, 0.5-1.0 mg/kg, 0.05-0.5 mg/kg, according to a dosing schedule of administration including without limitation daily, 2 or 3 times per week, weekly, every 2 weeks, every 3 weeks, monthly, etc., or other dose and dosing schedule deemed appropriate by the treating physician. As part of the combination therapy, the CD8$^+$CD39$^+$CD103$^+$ T cells can be administered to the subject before, after, or concurrent to the LAG3 or TIM-3 antagonist, as long as the administration schedule provides for a sufficient physiological concentrations of the agents to provide a therapeutic benefit. In yet other embodiments, the 4-1BB agonist (such as an antibody or antigen binding fragment that specifically binds to 4-1BB) can be administered at a dose in the range of from about 0.01-10 mg/kg, 0.01-5 mg/kg, 0.01-1 mg/kg, 0.01-0.1 mg/kg, 1-10 mg/kg, 1-5 mg/kg, 1-3 mg/kg, 0.5-1.0 mg/kg, 0.05-0.5 mg/kg, according to a dosing schedule of administration including without limitation daily, 2 or 3 times per week, weekly, every 2 weeks, every 3 weeks, monthly, etc., or other dose and dosing schedule deemed appropriate by the treating physician. As part of the combination therapy, the CD8$^+$CD39$^+$CD103$^+$ T cells can be administered to the subject before, after, or concurrent to the 4-1BB agonist, as long as the administration schedule provides for a sufficient physiological concentrations of the agents to provide a therapeutic benefit.

Sustained release compositions can be utilized. Suitable examples of sustained-release compositions include suitable polymeric materials (such as, for example, semi-permeable polymer matrices in the form of shaped articles, e.g., films, or mirocapsules), suitable hydrophobic materials (such as, for example, an emulsion in an acceptable oil) or ion exchange resins, and sparingly soluble derivatives (such as, for example, a sparingly soluble salt). Sustained-release formulations may be administered orally, rectally, parenterally, intracistemally, intravaginally, intraperitoneally, topically (as by powders, ointments, gels, drops or transdermal patch), bucally, or as an oral or nasal spray, depending on the location of the tumor.

The pharmaceutically acceptable carriers and excipients useful in the disclosed methods are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

Kits are also provided. CD8$^+$CD39$^+$CD103$^+$ T cells and/or the PD-1, PD-L1, PD-L2, LAG3, TIM-3, BTLA, or CTLA-4 antagonist can be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. Multiple treatments are envisioned, such as over defined intervals of time, such as daily, bi-weekly, weekly, bi-monthly or monthly, such that chronic administration is achieved.

Additional agents can be administered, such as a cytokine, a chemokine, or a chemotherapeutic agent. These can be included in the disclosed pharmaceutical compositions. A cytokine can be administered, such as interleukin-2 (IL-2), granulocyte macrophage colony stimulating factor (GM-CSF), or interferon, such as interferon (IFN) 0. In one example, for the prevention and treatment of cancer, surgical treatment can be administered to the subject. In one example, this administration is sequential. In other examples, this administration is simultaneous.

Examples of chemotherapeutic agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum. Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor, Genentech). In some embodiments, the subject is administered sorafenib.

Additional chemotherapeutic agent can be an antibody. Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. The antibody can specifically bind programmed death (PD)-1 or programmed death ligand (PD-L1) (see below). Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Treatment regimens also include combination with surgery, chemotherapy, radiation, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation, peptide vaccine, such as that described in Izumoto et al. 2008 J Neurosurg 108:963-971. Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (ARIMIDEX®), bicalutamide (CASODEX®), bleomycin sulfate (BLENOXANE®), busulfan (MYLERAN®), busulfan injection (BUSULFEX®), capecitabine (XELODA®), N4-pentoxycarbonyl-5-deoxy-5-fluorocytidine, carboplatin (PARAPLATIN®), carmustine (BICNU®), chlorambucil (LEUKERAN®), cisplatin (PLATINOL®), cladribine (LEUSTATIN®), cyclophosphamide (CYTOXAN® or NEOSAR®), cytarabine, cytosine arabinoside (CYTOSAR-U®), cytarabine liposome injection (DEPOCYT®), dacarbazine (DTIC-DOME®), dactinomycin (Actinomycin D, Cosmegan), daunorubicin hydrochloride (CERUBIDINE®), daunorubicin citrate liposome injection (DAUNOXOME®), dexamethasone, docetaxel (TAXOTERE®), doxorubicin hydrochloride (ADRIAMYCIN®, RUBEX®), etoposide (VEPESID@), fludarabine phosphate (FLUDARA®), 5-fluorouracil (ADRUCIL®, EFUDEX®), flutamide (EULEXIN®), tezacitibine, Gemcitabine (difluorodeoxycitidine), hydroxyurea (HYDREA®), Idarubicin (IDAMYCIN®), ifosfamide (IFEX®), irinotecan (CAMPTOSAR®), L-asparaginase (ELSPAR®), leucovorin calcium, melphalan (ALKERAN®), 6-mercaptopurine (PURINETHOL®), methotrexate (FOLEX®), mitoxantrone (NOVANTRONE®), mylotarg, paclitaxel (TAXOL®), phoenix (Yttrium90/MX-DTPA), pentostatin, polifeprosan 20 with carmustine implant (GLIADEL®), tamoxifen citrate (NOLVADEX®), teniposide (VUMON®), 6-thioguanine, thiotepa, tirapazamine (TIRAZONE®), topotecan hydrochloride for injection (HYCAMPTIN®), vinblastine (VELBAN®), vincristine (ONCOVIN®), and vinorelbine (NAVELBINE®). Exemplary alkylating agents include, without limitation, nitrogen mustards, ethylenimine derivatives, alkyl sulfonates, nitrosoureas and triazenes): uracil mustard (AMINOURACIL MUSTARD@, CHLORETHAMINACIL®, DEMETHYLDOPAN®, DESMETHYLDOPAN®, HAEMANTHAMINE®, NORDOPAN®, URACIL NITROGEN MUSTARD®, URACILLOST®, URACILMOSTAZA®. URAMUSTIN®, URAMUSTINE®), chlormethine (MUSTARGEN®), cyclophosphamide (CYTOXAN®, NEOSAR®, CLAFEN®, ENDOXAN®, PROCYTOX®, REVIMMUNE®), ifosfamide (MITOXANA®), melphalan (ALKERAN®), Chlorambucil (LEUKERAN®), pipobroman (AMEDEL®, VERCYTE®), triethylenemelamine (HEMEL®, HEXYLEN®, HEXASTAT®), triethylenethiophosphoramine. Temozolomide (TEMODAR®), thiotepa (THIOPLEX®), busulfan (BUSILVEX®, MYLERAN®), carmustine (BiCNU®), lomustine (CEENU®), streptozocin (ZANOSAR®), and Dacarbazine (DTIC-DOME®). Additional exemplary alkylating agents include, without limitation, Oxaliplatin (ELOXATIN®); Temozolomide (TEMODAR® and TEMODAL®); Dactinomycin (also known as actinomycin-D, COSMEGEN®); Melphalan (also known as L-PAM, L-sarcolysin, and phenylalanine mustard, ALKERAN®); Altretamine (also known as hexamethylmelamine (HMM), HEXYLEN®); Carmustine (BICNU®); Bendamustine (TREANDA®); Busulfan (BUSULFEX® and MYLERAN®); Carboplatin (PARAPLATIN®); Lomustine (also known as CCNU, CEENU®); Cisplatin (also known as CDDP, PLATINOL® and PLATINOL®-AQ); Chlorambucil (LEUKERAN®); Cyclophosphamide (CYTOXAN® and NEOSAR®); Dacarbazine (also known as DTIC, DIC and imidazole carboxamide, DTIC-DOME®); Altretamine (also known as hexamethylmelamine (HMM), HEXYLEN®); Ifosfamide (IFEX®); Prednumustine; Procarbazine (MATULANE®); Mechlorethamine (also known as nitrogen mustard, mustine and mechloroethamine hydrochloride. MUSTARGEN®); Streptozocin (ZANOSAR®); Thiotepa (also known as thiophosphoamide, TESPA and TSPA, THIOPLEX®); Cyclophosphamide (ENDOXAN®, CYTOXAN®, NEOSAR®, PROCYTOX®, REVIMMUNE®); and Bendamustine HCl (TREANDA®). Exemplary mTOR inhibitors include, e.g., temsirolimus; ridaforolimus (formally known as deferolimus, (1R,2R,4S)-4-[(2R)-2[(1R,9S,12S,15R,16E,18R,19R, 21R, 23S,24E,26E,28Z,30S,32S,35R)-1,18-dihydroxy-19, 30-dimethoxy-15,17,21,23, 29,35-hexamethyl-2,3,10,14, 20-pentaoxo-11,36-dioxa-4-azatricyclo[30.3.1.0$^{4.9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (AFINITOR® or RAD001); rapamycin (AY22989, SIROLIMUS®); simapimod (CAS164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS1013101-36-4); and $N^2$-[1,4-dioxo-4-[[4-(4-oxo-8-phenyl-4H-1-benzopyran-2-yl)morpholinium-4-yl]methoxy] butyl]-L-arginylglycyl-L-α-aspartylL-serine-, inner salt (SF1126, CAS 936487-67-1), and XL765. Exemplary immunomodulators include, e.g., afutuzumab (available from ROCHE®); pegfilgrastim (NEULASTA®); lenalidomide (CC-5013, REVLIMID®); thalidomide (THALOMID®), actimid (CC4047); and IRX-2 (mixture of human cytokines including interleukin 1, interleukin 2, and interferon γ, CAS 951209-71-5, available from IRX Therapeutics). Exemplary anthracyclines include. e.g., doxorubicin (Adriamycin® and RUBEX®); bleomycin (LENOXANE®); daunorubicin (dauorubicin hydrochloride, daunomycin, and rubidomycin hydrochloride, CERUBIDINE®); daunorubicin liposomal (daunorubicin citrate liposome, DAUNOXOME®); mitoxantrone (DHAD, NOVANTRONE®); epirubicin (ELLENCE™); idarubicin (IDAMYCIN®, IDAMYCIN PFS®); mitomycin C (MUTAMYCIN®); geldanamycin; herbimycin; ravidomycin; and desacetylravidomycin. Exemplary vinca alkaloids include, e.g., vinorelbine tartrate (NAVELBINE®), Vincristine (ONCOVIN®), and Vindesine (ELDISINE®)); vinblastine (also known as vinblastine sulfate, vincaleukoblastine and VLB, ALKABAN-AQ® and VELBAN®); and vinorelbine (NAVELBINE®). Exemplary proteosome inhibitors include bortezomib (VELCADE®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912). Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962. European Patent No. 1947183B1, U.S. Pat. Nos. 7,812,135, 8,388,967, 8,591,886, European Patent No. EP 1866339, PCT Publication No. WO 2011/028683, PCT Publication No. WO 2013/039954, PCT Publication No. WO2005/007190, PCT Publication No. WO 2007/133822, PCT Publication No. WO2005/055808, PCT Publication No. WO 1999/40196, PCT Publication No. WO 2001/03720, PCT Publication No. WO 1999/20758, PCT Publication No. WO2006/083289, PCT Publication No. WO 2005/115451, U.S. Pat. No. 7,618,632, and PCT Publication No. WO 2011/051726.

Method of Expanding CD39+CD103+CD8+ T Cells $CD8^+CD39^+CD103^+$ T cells can be expanded in vitro. In some embodiments, $CD8^+CD39^+CD103^+$ T cells isolated from a subject can be cultured in tissue culture medium comprising glutamine, serum, and antibiotics to form primary cultures. The cells are generally seeded in an appropriate culture vessel. A culture vessel used for culturing the cell(s) can include, but is particularly not limited to: flask, flask for tissue culture, dish, petri dish, dish for tissue culture, multi dish, micro plate, micro-well plate, multi plate, multi-well plate, micro slide, chamber slide, tube, tray, CELLSTACK® Chambers, culture bag, and roller bottle, as long as it is capable of culturing the T cells therein. The cells can be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In some embodiments, the culture vessel can be a tissue culture plate, for example, a 6-well, 24-well, or 96-well plate. In other embodiments, the culture vessel can be a bioreactor, which may refer to any device or system ex vivo that supports a biologically active environment such that cells can be propagated. The bioreactor can have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein, can be cultured with the nutrients necessary to support the growth of the population of cells.

Generally, the cells are cultured in growth media including a carbon source, a nitrogen source and a buffer to maintain pH. The medium can also contain fatty acids or lipids, amino acids (such as non-essential amino acids), vitamin(s), growth factors, cytokines, antioxidant substances, pyruvic acid, buffering agents, and inorganic salts. An exemplary growth medium contains a minimal essential media, such as Dulbecco's Modified Eagle's medium (DMEM) or ESSENTIAL 8M (E8) medium, supplemented with various nutrients, such as non-essential amino acids and vitamins, to enhance T cell growth. Examples of minimal essential media include, but are not limited to, Minimal Essential Medium Eagle (MEM) Alpha medium, Dulbecco's modified Eagle medium (DMEM), Roswell Park Memorial Institute (RPMI)-1640 medium, 199 medium, and F12 medium. Optionally, antibiotics can be added to a medium, such as, but not limited to, penicillin, streptomycin, or tetracycline. Glutamine can also be added to a tissue culture medium. Additives such as antibiotics and amino acids are known in the art.

Additionally, the minimal essential media may be supplemented with additional additives such as human, fetal calf or bovine serum. Serum can be included, for example, at a concentration of 10-15% (volume/volume), such as at about 5%, about 6%, about 7%, about 8%, about 9%, about 10%, about 11%, about 12%, about 13%, about 14%, or about 15% serum. The serum can be fetal calf serum. In other embodiments, the serum is human serum, such as human AB serum.

Alternatively, the medium can be serum free. In other cases, the growth media may contain a serum replacement. Exemplary serum replacements are known in the art. For example, KNOCKOUT™ serum replacement is disclosed, for example, in U.S. Patent Application No. 2002/0076747, which is incorporated herein by reference. Alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolgiycerol, or equivalents thereto. The alternatives to serum can be prepared by the method disclosed in International Publication No. WO 98/30679, for example.

A culture can be "xeno-Free (XF)" which refers to a medium or a culture condition, which is essentially free from heterogeneous animal-derived components. For culturing human cells, any proteins of a non-human animal, such as mouse, would be xeno components. Thus, in some embodiments, the disclosed conditions are xeno-free. Thus, for culturing human cells, a culture including human AB serum can be "xeno free."

Other culturing conditions can be appropriately defined. For example, the culturing temperature can be about 30 to 40° C., for example, at least or about 31, 32, 33, 34, 35, 36, 37, 38, 39° C. but particularly not limited to them. In one embodiment, the cells are cultured at 37° C. The $CO_2$ concentration can be about 1 to 10%, for example, about 2% to 5%, or any range derivable therein. In one non-limiting example, about 5% $CO_2$ concentration is utilized.

The primary cultures are stimulated with an effective amount of allogenic irradiated feeder cells and a cytokine, such as interleukin (IL)-15 or IL-2, to form stimulated T cells. The feeder cells can be, for example, allogeneic irradiated peripheral blood mononuclear cells. Feeder cells, including human feeder cells, can be irradiated, such as with 4000 rad of gamma irradiation.

In some embodiments, the cells are also stimulated with a polyclonal T cells stimulator, such as phytohemagglutinin. In some non-limiting examples, a concentration of 1 µg/ml to 2 µg/ml is utilized. In further embodiments, both a cytokine, such as IL-15 and/or IL-2, and PHA are utilized.

In some embodiments, a ratio is used such that about 1,000 to about 2,000 $CD8^+CD39^+CD103^+$ T cells are stimulated with about 100,000 to about 300,000 allogeneic feeder cells, such as irradiated allogeneic PBMC. In other embodiments, a ratio is used such that about 1,000 to about 2,000 $CD8^+CD39^+CD103^+$ T cells are stimulated with about 200,000 allogeneic feeder cells.

A cytokine, such as IL-2 or IL-15 can be included in the culture. In some embodiments, IL-15 can be used at a concentration of about 5 ng/ml to about 15 ng/ml of IL-15. In some embodiments, IL-15 is included in the culture at a concentration of about 7 ng/ml to about 12 ng/ml, such as at concentration of about 7, about 8, about 9, about 10, about 11, or about 12 ng/ml. In one non-limiting example, IL-15 is included at a concentration of about 10 ng/ml.

The stimulated CD39+CD103+CD8+ T cell cultures are then replenished with fresh tissue culture medium and the cytokine, such as IL-15 and/or IL-2, throughout the in-vitro expansion. IL-15 can be included in this tissue culture medium at a concentration of about 5 ng/ml to about 50 ng/ml of IL-15, such as about 10 ng/ml to about 50 ng/ml of IL-15. In some embodiments, IL-15 is included in the culture at a concentration of about 7 ng/ml to about 12 ng/ml, such as at concentration of about 7, about 8, about 9, about 10, about 11, or about 12 ng/ml. In one non-limiting example, IL-15 is included at a concentration of about 10 ng/ml. In other examples, IL-15 is included at a concentration of about 20, about 30, about 40, or about 50 ng/ml.

The cell culture can be maintained for any period. In some embodiments, following 15 to 30 days in culture, the expanded CD39+CD103+CD8+ T cells are harvested.

Methods of Isolating and Using a Nucleic Acid Encoding T Cell Receptors

Methods are provided for isolating nucleic acid encoding T cell receptors (TCRs) that specifically bind tumor cell antigens. These methods include isolating $CD39^+CD8^+$ T cells, such as CD39+ CD103+ CD8 T cells, from a sample from a subject with a tumor expressing the tumor cell antigen. In some embodiments, the tumor is a solid tumor, such as a head and neck squamous cell carcinoma, lung cancer, melanoma, ovarian cancer renal cell carcinoma, bladder cancer, cervical cancer, liver cancer, prostate cancer, breast cancer, glioblastoma or rectal cancer. The subject can be a human subject or a veterinary subject. The sample can be any sample from the subject, including, but not limited to, a peripheral blood sample or a tumor biopsy. Methods for isolating $CD8^+CD39^+$ T cells, such as CD39+ CD103+ CD8 T cells, are disclosed above.

In some embodiments, the methods include expanding the $CD8^+CD39^+$ T cells, such as CD39+ CD103+ CD8 T cells. Methods expanding for the $CD8^+CD39^+$ T cells, such as CD39+CD103+ CD8 T cells, in vitro are also disclosed above. In other embodiments, primary $CD8^+CD39^+$ T cells, such as CD39+ CD103+ CD8 T cells, are utilized, wherein the cells are not expanded in vitro.

The methods further include cloning a nucleic acid molecule encoding a TCR from the $CD8^+CD39^+$ T cells, such as CD39+ CD103+ CD8 T cells. Methods for cloning TCRs are known in the art, see for example, U.S. Pat. No. 8,697,854, incorporated herein by reference. TCR's are members of the immunoglobulin superfamily and usually consist of and α- and β-subunits. These possess one N-terminal immunoglobulin (Ig)-variable (V) domain, one Ig-constant (C) domain, a transmembrane/cell membrane-spanning region, and a short cytoplasmic tail at the C-terminal end. The variable domains of both the TCR α-chain and β-chain have three hypervariable or complementarity determining regions (CDRs), whereas the variable region of the 3-chain has an additional area of hypervariability (HV4) that does not normally contact antigen and therefore is not considered a CDR.

CDR3 is the primary CDR that recognizes processed antigen, although CDR1 of the alpha chain has also been shown to interact with the N-terminal part of an antigenic peptide. CDR1 of the 3-chain also interacts with the C-terminal part of the peptide. CDR2 is thought to recognize the MHC. CDR4 of the O-chain is not thought to participate in antigen recognition, but has been shown to interact with superantigens. The constant domain of the TCR domain consists of short connecting sequences in which a cysteine residue forms disulfide bonds, which forms a link between the two chains. The affinity of TCR's for a specific antigen makes them of use therapeutically. For example, tumors can be effectively treated by using adoptive immunotherapy with T cells expressing a specific TCR. Methods for cloning TCRs, and for using adoptive immunotherapy using cells transfected with TCRs, are disclosed in PCT Publication No. WO 2006/031221, U.S. Pat. No. 5,906,936; PCT Publication No. WO97/32603; PCT Publication No. WO2007/065957, and PCT Publication No. WO2008/039818. Methods of generating nucleic acid molecules encoding TCR and T cells (or NK cells) including such receptors are disclosed, for example, in Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.*, 29:550-557, 2011; Grupp et al., N Engl J Med., 368:1509-1518, 2013; Han et al., J. Hematol Oncol., 6:47, 2013; PCT Pub. WO2012/079000, WO2013/126726; and U.S. Pub. 2012/0213783, each of which is incorporated by reference herein in its entirety).

In some embodiments, single cell RNA sequences are used for the T cell receptors or pair-seq (Adaptive). In one non-limiting example, purified T cells are isolated to single cells using a fluidigm or 10x genomics instrument. T Cell DNA is then amplified and sequenced. T cells do not need to be primed or have antigen presented for this process.

Additional examples of appropriate cloning and sequencing techniques, and instructions sufficient to direct persons of skill through many cloning exercises are known (see, e.g, Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acid sequences encoding the TCR can be prepared by any suitable method. Once the entire sequence is cloned and known, it can also be prepared by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill. Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

The nucleic acid molecule encoding the TCR can operably linked to a heterologous promoter. The nucleic acid molecule encoding the TCR can be included in a vector (such as a lentiviral vector or gamma retroviral vector) for expression in a host cell. Exemplary cells are mammalian cells, and include a T cell, such as a cytotoxic T lymphocyte (CTL) and a NK cell. In specific non-limiting examples, the cell is a T cell, such as a CD3$^+$ T cell. The CD3$^+$ T cell can be a CD4$^+$ or a CD8$^+$ T cell.

The nucleic acid molecules also can be expressed in a recombinantly engineered cell such as bacteria, plant, yeast, insect and mammalian cells. The TCR can be expressed as a fusion protein. Methods of expressing and purifying antibodies and antigen binding fragments are known and further described herein (see, e.g., Al-Rubeai (ed), *Antibody Expression and Production*, Springer Press, 2011). Those of skill in the art are knowledgeable in the numerous expression systems available for expression of proteins including *E. coli*, other bacterial hosts, yeast, and various higher eukaryotic cells such as the COS, CHO, HeLa and myeloma cell lines. The term "host cell" also includes any progeny of the subject host cell. It is understood that all progeny may not be identical to the parental cell since there may be mutations that occur during replication. Methods of stable transfer, meaning that the foreign DNA is continuously maintained in the host, are known in the art. As disclosed herein, specific embodiments of the present disclosure include T cells, such as human T cells and human NK cells, which express the TCR. These T cells can be CD3$^+$ T cells, such as CD4$^+$ or CD8$^+$ T cells.

The expression of nucleic acids encoding the TCR to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences).

When the host is a eukaryote, such methods of transfection of DNA as calcium phosphate coprecipitates, conventional mechanical procedures such as microinjection, electroporation, insertion of a plasmid encased in liposomes, or virus vectors may be used. Cells transformed by the cassettes can be selected by resistance to antibiotics conferred by genes contained in the cassettes, such as the amp, gpt, neo and hyg genes.

Eukaryotic cells can also be cotransformed with polynucleotide sequences encoding the TCR, and a second foreign DNA molecule encoding a selectable phenotype, such as the herpes simplex thymidine kinase gene. Another method is to use a eukaryotic viral vector, such as simian virus 40 (SV40), a lentivirus or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

In some embodiments, a viral vector is utilized for expression of the TCR. Viral vectors include, but are not limited to simian virus 40, adenoviruses, adeno-associated virus (AAV), lentiviral vectors, and retroviruses, such as gamma retroviruses. Retroviral vectors provide a highly efficient method for gene transfer into eukaryotic cells. Moreover, retroviral integration takes place in a controlled fashion and results in the stable integration of one or a few copies of the new genetic information per cell. Without being bound by theory, lentiviral vectors have the advantage over vectors derived from onco-retroviruses such as murine leukemia viruses in that they can transduce non-proliferating cells, such as hepatocytes. They also have the added advantage of low immunogenicity. The use of lentiviral vectors to express a TCR is known in the art, and is disclosed for example in U.S. Application No. 2014/0050708, which is incorporated herein by reference. A transposon can be used.

In some embodiments, host cells are produced for introduction into subject of interest. The host cell can be a peripheral blood lymphocyte (PBL) or a peripheral blood mononuclear cell (PBMC), a purified T cell, or a purified NK cell. The T cell can be any T cell, such as a cultured T cell, e.g., a primary T cell, or a T cell from a cultured T cell line, e.g., Jurkat, SupT1, etc., or a T cell obtained from a mammal (such as a human patient to which the TCR-T cell will later be administered). If obtained from a mammalian subject, such as a human subject, the T cell can be obtained from numerous sources, including but not limited to blood, bone marrow, lymph node, the thymus, or other tissues or fluids. T cells can also be enriched for or purified. The T cell can be any type of T cell and can be of any developmental stage, including but not limited to, $CD3^+$ cells, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naive T cells, and the like. The T cell may be a $CD3^+$ T cell, such as a $CD8^+$ T cell or a $CD4^+$ T cell. In alternative embodiments, the cell can be an NK cells, such as an NK cell obtained from the same subject to which the TCR-NK cell will later be administered.

In some embodiments, the cells are human. In other embodiments, the cells are from a veterinary subject.

Also provided is a population of cells comprising at least one host cell described herein. The population of cells can be a heterogeneous population comprising the host cell comprising any of the recombinant expression vectors encoding the TCR, in addition to at least one other cell, e.g., a host cell (e.g., a T cell), which does not comprise any recombinant expression vector, or a cell other than a T cell, e.g., a B cell, a macrophage, a neutrophil, an erythrocyte, etc. Alternatively, the population of cells can be a substantially homogeneous population, in which the population comprises mainly host cells (e.g., consisting essentially of) comprising the recombinant expression vector encoding the TCR. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein. The T cells can be CD3+ T cells, such as $CD8^+$ T cell or a $CD4^+$ T cells. The cells can also be NK cells.

The cells can be autologous to a recipient. The recipient can have a tumor, or be at risk for having a tumor. The recipient can have undergone prior treatment for a tumor. The tumor can be a solid tumor, such as solid tumor is a head and neck squamous cell carcinoma, lung cancer, melanoma, ovarian cancer renal cell carcinoma, bladder cancer, cervical cancer, liver cancer, prostate cancer, breast cancer, glioblastoma or rectal cancer. In some embodiments, autologous T cells or NK cells are isolated from a subject, such as a human subject, and the isolated TCR is introduced into these cells. These transformed cells are then re-introduced to the subject. In this scenario, the donor and the recipient are the same subject. The subject can be human. In some embodiments, a subject is administered a therapeutically effective amount of T cells and/or NK cells expressing the cloned TCR. In particular embodiments (see U.S. Published Application No. US20140271635 A1, incorporated herein by reference), prior to expansion and genetic modification, a source of T cells is obtained from a subject.

In some embodiments, the T and/or NK cells are autologous. In other embodiments, the T cells and/or NK cells are allogeneic. The T cells and/or NK cells are then introduced into the subject, as disclosed above. In one embodiment, the cells transiently express the vector for 4, 5, 6, 7, 8, 9, 10, 11, 12, 13, 14, 15 days after transduction. In one non-limiting example, the vector is transduced into the T cell by electroporation.

The term "subject" is intended to include living organisms in which an immune response can be elicited (e.g., mammals). Examples of subjects include humans, dogs, cats, mice, rats, pigs (and other veterinary subjects) and non-human primates. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In other embodiments, any number of T cell lines available in the art, may be used. In some embodiments, subjects can undergo leukapheresis, wherein leukocytes are collected, enriched, or depleted ex vivo to select and/or isolate the cells of interest, e.g., T cells and or NK cells. These cell isolates may be expanded by methods known in the art and treated such that a TCR construct is introduced, thereby creating an autologous cell that express the cloned TCR. In one aspect, TCR expressing cells are generated using viral vector, such as, but not limited to, lentiviral viral vectors. In some non-limiting examples, T cells and/or NK cells can be obtained from a unit of blood collected from a subject using any number of techniques known to the skilled artisan, such as FICOLL™ separation, or the cells can be obtained by apheresis. The apheresis product typically contains lymphocytes, including T cells, monocytes, granulocytes, B cells, NK cells, other nucleated white blood cells, red blood cells, and platelets.

Cells collected by apheresis can be washed to remove the plasma fraction and to place the cells in an appropriate buffer or media for subsequent processing steps. In some non-limiting examples, the cells are washed with phosphate buffered saline (PBS). In an alternative examples, the wash solution lacks calcium and may lack magnesium or may lack many if not all divalent cations. Initial activation steps in the absence of calcium can lead to magnified activation. The washing step can be accomplished by methods known in the art, such as by using a semi-automated "flow-through" centrifuge (for example, the Cobe 2991 cell processor, the Baxter CYTOMATE®, or the HAEMONETICS CELL SAVER 5®) according to the manufacturer's instructions. After washing, the cells can be resuspended in a variety of biocompatible buffers, such as a saline solution with or without buffer. Alternatively, the undesirable components of the apheresis sample can be removed and the cells directly resuspended in culture media.

In some embodiments, T cells are isolated from peripheral blood lymphocytes by negative selection. A specific subpopulation of T cells, such as CD3+, CD4+, CD8+, CD28+ CD45RA+, and CD45RO+ T cells, naïve and/or memory T cells, can be further isolated by positive or negative selection techniques. For example, T cells can isolated by incubation with anti-CD3/anti-CD28 conjugated beads, such as DYNABEADS® M-450 CD3/CD28 T, or CD3/IL-2, for a time period sufficient for positive selection of the desired T cells, see for example U.S. Published Application No. US20140271635 A1. In a non-limiting example the time period is about 24 to about 72 hours and all integer values there between. In further non-limiting examples, the time period is at least 24 hours, 36, 48 hours or longer. Longer incubation times can be used to isolate T cells in any situation where there are few T cells as compared to other cell types, such in isolation from immunocompromised individuals. Multiple rounds of selection can also be used.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD8a, CD14, CD15, CD16, CD19, CD36, CD56, CD132, TCR γ/δ, and CD235a (Glycophorin A). To enrich for CD8+ cells by negative selection, the monoclonal antibody cocktail contains antibodies to CD4, CD15, CD16, CD19, CD34, CD36, CD56, CD123, TCR γ/δ, and CD235a. A T cell population can be selected that expresses one or more cytokines. Methods for screening for cell expression are disclosed in PCT Publication No. WO 2013/126712.

For isolation of a desired population of cells by positive or negative selection, the concentration of cells and surface (e.g., particles such as beads) can be varied to ensure maximum contact of cells and beads. In some embodiments, a concentration of 1 million cells/ml is used. In further embodiments, greater than 100 million cells/ml is used. In other embodiments, a concentration of cells of 10, 15, 20, 25, 30, 35, 40, 45, 50, 65, 70, 75, 80, 85, 90, 95, or 100 million cells/ml is used. Without being bound by theory, using high concentrations can result in increased cell yield, cell activation, and cell expansion. Lower concentrations of cells can also be used. Without being bound by theory, significantly diluting the mixture of T cells and surface (e.g., particles such as beads), interactions between the particles and cells is minimized. This selects for cells that express high amounts of desired antigens to be bound to the particles. In some embodiments, the concentration of cells used is $5 \times 10^6$/ml. In other embodiments, the concentration used can be from about $1 \times 10^5$/ml to $1 \times 10^6$/ml, and any integer value in between.

Cells can be incubated on a rotator for varying lengths of time at varying speeds at either 2-10° C. or at room temperature. T cells for stimulation can also be frozen after a washing step. Without being bound by theory, the freeze and subsequent thaw step provides a more uniform product by removing granulocytes and to some extent monocytes in the cell population. After the washing step that removes plasma and platelets, the cells can be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 10 per minute and stored in the vapor phase of a liquid nitrogen storage tank. Other methods of controlled freezing may be used as well as uncontrolled freezing immediately at −20° C. or in liquid nitrogen, see U.S. Publication No. US-2014-0271635 A1.

Blood samples or apheresis product can be collected from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one aspect a blood sample or an apheresis is taken from a generally healthy subject. In certain aspects, a blood sample or an apheresis is taken from a generally healthy subject who is at risk of developing a disease, such as a tumor, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease, such as a tumor, as described herein but prior to any treatments. In a further aspect, the cells are isolated from a blood sample or an apheresis from a subject prior to any number of relevant treatment modalities. In certain aspects, cryopreserved cells are thawed and washed as described herein and allowed to rest for one hour at room temperature prior to use. Blood samples or apheresis product can be collected from a subject when needed, and not frozen. In some embodiments, autologous tumor-bearing T cells are isolated from individuals for subsequent transfection and infusion.

T cells can be activated and expanded generally using methods as described, for example, in U.S. Pat. Nos. 6,352, 694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded by contact with a surface having attached thereto an agent that stimulates a CD3/TCR complex associated signal and a ligand that stimulates a costimulatory molecule on the surface of the T cells. T cells can also be expanded using PHA or bulk PBMCs can to be transfected with CD3/28 or CD3/IL2. In some non-limiting examples, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9): 13191328, 1999; Garland et al., J. Immunol. Meth. 227(1-2):53-63, 1999). Other methods include the use of allogeneic, irradiated PBMC's together with phytohaemagglutinin to stimulate T cell proliferation.

Once a TCR is isolated, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. In some embodiments, the upregluation of activation markers, such as, but not limited to, 1-1BB is evaluated, such as by flow cytometry.

The method includes administering to the subject a therapeutically effective amount of the pharmaceutical composition cells, such as T cells and/or NK cells, that express the cloned TCR. Subjects in need thereof, such as a subject with a tumor, may subsequently undergo standard treatment with chemotherapy or surgery (for cancer) or anti-viral agents (for an HIV infection). The administration of the host cells expressing the heterologous TCR can result in treating the tumor, such as decreasing tumor volume, decreasing metastasis, or decreasing a sign or symptom of the tumor.

Pharmaceutical compositions can include a TCR-expressing host cell, e.g., a plurality of TCR-expressing host cells, as described herein, in combination with one or more pharmaceutically or physiologically acceptable carriers, diluents or excipients. The TCR-expressing host cells can be T cells, such as CD3+ T cells, such as CD4+ and/or CD8+ T cells, and/or NK cells. Such compositions may include buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

With regard to the cells, a variety of aqueous carriers can be used, for example, buffered saline and the like, for introducing the cells. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration in these formulations can vary widely, and will be selected primarily based on fluid volumes, viscosities, body weight and the like in accordance with the particular mode of administration selected and the subject's needs.

In one embodiment, the pharmaceutical composition is substantially free of, e.g., there are no detectable levels of a contaminant, such as endotoxin, *mycoplasma*, replication competent lentivirus (RCL), p24, VSV-G nucleic acid, HIV gag, residual anti-CD8/anti-CD39/anti-CD103 coated beads, mouse antibodies, pooled human serum, bovine serum albumin, bovine serum, culture media components, vector packaging cell or plasmid components, a bacterium and a fungus.

The precise amount of the composition to be administered can be determined by a physician with consideration of individual differences in age, weight, tumor size, extent of metastasis, and condition of the patient (subject). It can generally be stated that a pharmaceutical composition comprising the T cells (and/or NK cells) described herein may be administered at a dosage of $10^4$ to $10^9$ cells/kg body weight, such as $10^5$ to $10^6$ cells/kg body weight, including all integer values within those ranges. Exemplary doses are $10^6$ cells/kg to about $1\times10^8$ cells/kg, such as from about $5\times10^6$ cells/kg to about $7.5\times10^7$ cells/kg, such as at about $2.5\times10^7$ cells/kg, or at about $5.0\times10^7$ cells/kg.

A composition can be administered once or multiple times, such as 2, 3, 4, 5, 6, 7, 8, 9, or 10 times at these dosages. The composition can be administered by using infusion techniques that are commonly known in immunotherapy (see, e.g., Rosenberg et al., New Eng. J. of Med. 319:1676, 1988). The compositions can be administered daily, weekly, bimonthly or monthly. In some non-limiting examples, the composition is formulated for intravenous administration and is administered multiple times. The quantity and frequency of administration will be determined by such factors as the condition of the subject, and the type and severity of the subject's disease, although appropriate dosages may be determined by clinical trials.

In one embodiment, the TCR is introduced into cells, such T cells or NK cells, and the subject receives an initial administration of cells, and one or more subsequent administrations of the cells, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the cells is provided to the subject (e.g., human) per week, e.g., 2, 3, or 4 administrations of the TCR expressing cells are administered per week. In one embodiment, the subject receives more than one administration of the T cells per week (e.g., 2, 3 or 4 administrations per week) (also referred to as a cycle), followed by a week of no administrations, and then one or more additional administration of the TCR expressing cells (e.g., more than one administration of the cells per week) is administered to the subject. In another embodiment, the subject (e.g., human subject) receives more than one cycle of TCR expressing cells, and the time between each cycle is less than 10, 9, 8, 7, 6, 5, 4, or 3 days. In one embodiment, the TCR expressing cells are administered every other day for 3 administrations per week. In another embodiment, the TCR expressing cells are administered for at least two, three, four, five, six, seven, eight or more weeks. The dosage of the above treatments to be administered to a patient will vary with the precise nature of the condition being treated and the recipient of the treatment. The scaling of dosages for human administration can be performed according to art-accepted practices.

In some embodiments, TCR-modified T cells are able to replicate in vivo resulting in long-term persistence that can lead to sustained tumor control. In various aspects, the T cells administered to the subject, or the progeny of these cells, persist in the subject for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, or for years after administration of the T cell to the subject. In other embodiments, the cells and their progeny are present for less than six months, five month, four months, three months two months, or one month, e.g., three weeks, two weeks, one week, after administration of the T cell to the subject.

The administration of the subject compositions may be carried out in any convenient manner, including by injection, transfusion, implantation or transplantation. The disclosed compositions can be administered to a patient trans arterially, subcutaneously, intradermally, intratumorally, intranodally, intramedullary, intramuscularly, by intravenous (i.v.) injection, or intraperitoneally. In some embodiments, the compositions are administered to a patient by intradermal or subcutaneous injection. In other embodiments, the compositions of the present invention are administered by i.v. injection. The compositions can also be injected directly into a tumor or lymph node.

In one embodiment, compositions containing isolated populations of cells can also contain one or more additional pharmaceutical agents, such as one or more anti-microbial agents (for example, antibiotics, anti-viral agents and anti-fungal agents), anti-tumor agents (for example, fluorouracil, methotrexate, paclitaxel, fludarabine, etoposide, doxorubicin, or vincristine), depleting agents (for example, fludarabine, etoposide, doxorubicin, or vincristine), or non-steroidal anti-inflammatory agents such as acetylsalicylic acid, ibuprofen or naproxen sodium), cytokines (for example, interleukin-2), or a vaccine. Many chemotherapeutic agents are presently known in the art. In one embodiment, the chemotherapeutic agent is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

For the treatment of malignancy, the method can also include administering to the subject a therapeutically effective amount of an additional cancer therapeutic (including chemotherapeutic agents and radiation) or surgery.

The cells expressing the TCR can be administered in conjunction with surgery, radiation, chemotherapy, or immunotherapy. Suitable chemotherapeutic agents are disclosed above. Cells expressing the TCR can also be administered with a PD-1, CTLA-4, TIM-3, LAG3, BTLA Antagonist and/or a 4-1BB Agonist, as disclosed in detail below.

Methods of Detecting and Treatment

It is disclosed herein that administration of $CD39^+CD8^+$ T cells, such as CD39+CD103+ CD8 T cells, are of use in diagnosis and treatment. In these embodiments, $CD39^+$ $CD8^+$ T cells, such as CD39+ CD103+ CD8 T cells, are measured in a biological sample from a subject. In some embodiments, the sample is a peripheral blood sample or a tumor biopsy. The subject can be any subject, such as a human or a veterinary subject. In further embodiments, the subject has a tumor, is suspected of having a tumor, or is at risk of having a tumor. The tumor can be a solid tumor. In some non-limiting examples, the solid tumor is a head and neck squamous cell carcinoma, lung cancer, melanoma, ovarian cancer renal cell carcinoma, bladder cancer, cervical cancer, liver cancer, prostate cancer, breast cancer, glioblastoma or rectal cancer.

In some embodiments, methods are disclosed for determining if a subject with a tumor will respond to a cancer therapeutic, which include, but a not limited to, biological response modifiers (such as cytokines and chemokines), cancer vaccines, chemotherapeutic agents, immunotherapeutic agents, and radiation. In some embodiments, the cancer therapeutic can be a checkpoint inhibitor, a 4-1BB agonist and/or radiation. The cancer therapeutic can be a chemical. The methods can also be used to detect if a subject will respond to surgery.

These methods include detecting the presence of $CD39^+$ $CD8^+$ T cells, such as CD39+ CD103+ CD8 T cells, in a biological sample from a subject, wherein the presence of the CD39+CD8+ T cells, such as CD39+ CD103+ CD8 T cells, in the biological sample that the cancer therapeutic, such as, but not limited to, a checkpoint inhibitor, 4-1BB agonist, and/or radiation, will be effective for treating the tumor in the subject. The method can also indicate that the subject will respond to a surgical procedure, such as resection. The method can also include administering the cancer therapeutic to the subject, or performing the surgical procedure. In some non-limiting examples, the cancer therapeutic is a checkpoint inhibitor, which can be, without limitation, a PD-1 antagonist, a PD-L1 antagonist, a CTLA-4 antagonist, a BTLA antagonist, a TIM-3 antagonist or a LAG3 antagonist. Suitable antagonists are disclosed in detail below. Suitable 4-1BB agonists are also disclosed below.

In other embodiments, methods are disclosed for determining if a subject with a tumor will respond to a therapeutic regimen, such as including a cancer therapeutic. The cancer therapeutic can be a chemotherapeutic agent or radiation. The cancer therapeutic can be a checkpoint inhibitor, such as a PD-1 antagonist, a PD-L1 antagonist, a CTLA-4 antagonist, a BTLA antagonist, a TIM-3 antagonist or a LAG3 antagonist, or can be a 4-1BB agonist. In some embodiments, the methods include administering to a subject a first dose of the cancer therapeutic, and determining the number of $CD39^+CD8^+$ T cells, such as CD39+ CD103+ CD8 T cells, in a biological sample from a subject. An increase in the amount of $CD39^+CD8^+$ T cells, such as CD39+ CD103+ CD8 T cells, in the biological sample as compared to a control indicates that the first dose of the cancer therapeutic is effective for treating the tumor in the subject.

In further embodiments, methods are disclosed for determining if a subject with a tumor will respond to a cancer therapeutic. The cancer therapeutic can be a chemotherapeutic agent or radiation. The cancer therapeutic can be a checkpoint inhibitor, such as a PD-1 antagonist, a PD-L1 antagonist, a CTLA-4 antagonist, a BTLA antagonist, a TIM-3 antagonist or a LAG3 antagonist, or can be a 4-1BB agonist. These methods include administering to a subject a first dose of the cancer therapeutic, and determining the number of CD39+CD8+ T cells, such as CD39+ CD103+ CD8 T cells, in a biological sample from a subject, wherein an increase in the amount of CD39+CD8+ T cells, such as CD39+ CD103+ CD8 T cells, in the biological sample as compared to a control indicates that the first dose of the cancer therapeutic is effective for treating the tumor in the subject. In additional embodiments, the methods further include administering a second dose of the cancer therapeutic to the subject, wherein the first dose is the same as the second dose, or wherein the second dose is lower than the first dose.

In yet other embodiments, methods are disclosed for treating a subject with a tumor. These methods include administering to a subject a first dose of the cancer therapeutic, and determining the number of CD39+CD8+ T cells, such as CD39+ CD103+ CD8 T cells, in a biological sample from a subject. A decrease or no change in the amount of CD39+CD8+ T cells, such as CD39+CD103+ CD8 T cells, in the biological sample as compared to a control indicates that the first dose of the cancer therapeutic is not effective for treating the tumor in the subject. A second dose of the cancer therapeutic is administered to the subject, wherein the second dose is higher than the first dose, or wherein the second dose is the same as the first dose.

In some embodiments, the subject has tumor, or is at risk of developing a tumor, as discussed above. These subjects can be identified by standard methods suitable by one of skill in the art, such as a physician. The disclosed methods include selecting a subject of interest, and administering the cancer therapeutic of interest, including, but not limited to a checkpoint inhibitor, such as a PD-1 antagonist, a PD-L1 antagonist, a CTLA-4 antagonist, a BTLA antagonist, a TIM-3 antagonist or a LAG3 antagonist. The subject can also be administered a 4-1BB agonist. The method can detect subjects that will respond to a surgical procedure.

In additional embodiments, the subject is administered a therapeutically effective amount of CD39+CD8+ T cells, such as CD39+ CD103+ CD8 T cells, and a therapeutically effective amount of a cancer therapeutic, such as, but not limited to, a checkpoint inhibitor, for example a PD-1 antagonist, a PD-L1 antagonist, a CTLA-4 antagonist, a BTLA antagonist, a TIM-3 antagonist or a LAG3 antagonist. In additional embodiments, subject can be administered a 4-1BB agonist. Administration of the purified CD39+CD8+ T cells, such as CD39+ CD103+ CD8 T cells, and a checkpoint inhibitor or a 4-1BB agonist, as disclosed herein, will increase the ability of a subject to overcome pathological conditions, such as a tumor. The cells and the checkpoint inhibitor can be included in a single pharmaceutical composition or in separate pharmaceutical compositions. Therefore, by purifying and generating a purified population of CD39+CD8+ T cells, such as CD39+ CD103+ CD8 T cells, from a subject ex vivo and introducing a therapeutic amount of these cells, the immune response of the recipient subject is enhanced. The administration of a therapeutically effective amount of a checkpoint inhibitor or a 4-1BB agonist also enhances the immune response of the recipient. Thus, the methods disclosed herein for determining if a chemotherapeutic agent or radiation is effective can be used in combination with any of the therapeutic methods (and in any of the subjects) described above.

The methods can also be used to evaluate the dose of a cancer therapeutic that is therapeutically effective for a subject. For example, the methods disclosed herein can be used to determine if the dose administered to a subject of interest can be lowered and still be effective. The methods disclosed herein also can be used to determine if the dose administered to a subject is too low, and thus must be increased to be therapeutically effective.

Any of the disclosed methods can include measuring other cell types, such as B and/or T cells. The disclosed methods can also include measuring the expression of markers such as PD-1, PD-L1, CTLA-4, BTLA, TIM-3 or LAG3. The expression of CD8, CD39 and/or CD103 is evaluated.

In some embodiments, CD39+CD8+ T cells, such as CD39+ CD103+ CD8 T cells, are measured. An increase in the number of CD39+CD8+ T cells, such as CD39+ CD103+ CD8 T cells, from the biological sample as compared to a control indicates that the dose of the cancer therapeutic is of use treating the subject, and wherein an absence of a significant alteration in the number of CD39+CD8+ T cells, such as CD39+ CD103+ CD8 T cells, as compared to the control indicates that the dose of the cancer therapeutic is not of use to treat the subject. The control can be a previously determined standard value, or the quantity of CD39+CD8+ T cells, such as CD39+ CD103+ CD8 T cells, in a sample from the subject prior to the administration of the cancer therapeutic, or the quantity of CD39+CD8+ T cells, such as CD39+ CD103+ CD8 T cells, in a sample from the subject, when the subject is administered a control substance.

Generally, measuring the number of CD39+CD8+ T cells, such as CD39+ CD103+ CD8 T cells, includes obtaining a sample that includes T cells from a subject, and determining the presence or number of CD39+CD8+ T cells, such as CD39+ CD103+ CD8 T cells, in the sample. In some examples, the sample is a biopsy sample, a blood sample, or a sample of peripheral blood mononuclear cells. The methods include immunohistochemistry and/or flow cytometry.

The methods can include immunohistochemistry methods, such as on a biological sample from a subject. The sample can be a tumor sample. In some embodiments, an antibody (or antigen binding fragment), such as an antibody that binds CD8, CD39 or CD103 is directly labeled with a detectable label. In another embodiment, the antibody (or antigen binding fragment) that binds CD8, CD39 or CD103 (the first antibody) is unlabeled and a second antibody or other molecule that can bind the antibody that binds the first antibody is utilized. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

Cells can also be quantitated using flow cytometry. In additional embodiments, the sample can be purified, for example to separate T cells, such as CD8 T cells or CD39+ CD8+ T cells, such as CD39+ CD103+ CD8 T cells. In some embodiments, the methods include measuring the quantity of CD39+CD8+ T cells, such as CD39+ CD103+ CD8 T cells. In some examples, the quantity of CD39+CD8+ T cells, such as CD39+ CD103+ CD8 T cells, in a biological sample is compared to a control. Suitable controls are noted above.

In some examples, cell suspensions are produced from a tumor sample. In one non-limiting example, under sterile conditions, tumors are cut into small pieces and digested in RPMI-1640 with hyaluronidase, collagenase, DNase as well as human serum albumin. Cells can be digested, for example, for 1 hour at room temperature under agitation with a magnetic stir bar. Cell suspensions are filtered through a cell filter. Tumor infiltrating lymphocytes can be enriched as by centrifugation with a density gradient solution.

Methods for isolating, detecting, and/or quantitating T cells are known in the art, and exemplary protocols are provided herein. Methods also are known in the art to measure the proliferation of T cells. These methods generally involve the use of molecular and/or biochemical techniques and not simple visual observation. Cells in some examples, fluorescence activated cell analyses (FACS) is utilized. FACS can be used to sort (isolate) cells such as T cells by staining the cells with an appropriately labeled antibody. In one embodiment, several antibodies (such as antibodies that bind CD8, CD39 and CD103) and FACS sorting can be used to produce substantially purified populations of CD39+CD8+ T cells, such as CD39+ CD103+ CD8 T cells. Any FACS technique can be employed, see, for example, methods of FACS disclosed in U.S. Pat. No. 5,061,620.

However, other techniques of differing efficacy can be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Separation procedures include magnetic separation, using antibody-coated magnetic beads, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the cells expressing a marker of interest (e.g., CD39 or CD103) to bind to the solid-phase linked antibodies. The bound cells are then separated from the solid phase by any appropriate method, depending mainly upon the nature of the solid phase and the antibody employed.

Antibodies can be conjugated to biotin, which then can be removed with avidin or streptavidin bound to a support, or fluorochromes, which can be used, with FACS, to enable cell separation.

For example, cells expressing CD8 or CD3 are initially separated from other cells by the cell-surface expression of CD8 or CD3. Purity of the isolated CD8+ cells or CD3+ cells is then checked, such as with a BD LSRFORTESSA® flow cytometer (Becton Dickinson, San Jose, Calif.), if so desired. In one embodiment, further purification steps are performed, such as FACS sorting the population of cells. In one example, this sorting can be performed to detect expression of CD39, CD103, and CD8.

The methods can also include measuring cell proliferation. Methods for analyzing cell proliferation, such as the assessment of the proliferation are known in the art. For example, membrane dye dilution approaches can be utilized which include ex vivo chemical labeling of cells of interest with fluorescent dyes. Labeling with tritiated nucleoside analogues (commonly $^3$H-thymidine deoxyribonucleoside, $^3$H-TdR) or bromodeoxyuridine (BrdU) can be utilized. FACS analysis is available for the measurement of BrdU incorporation. Surrogate markers of proliferation such as DNA content and cell cycle-associated proteins, can also be used.

In one example, measurement of Ki67 or PCNA can be utilized. Ki67 antigen is the prototypic cell cycle related nuclear protein that is expressed by proliferating cells in all phases of the active cell cycle (G1, S, G2 and M phase). It is absent in resting (G0) cells. Ki67 antibodies are useful in establishing proliferation. Ki67 antibodies can be used to quantify proliferating cells among and resting cells (Ki67 index). Ki67 is routinely used as a marker of cell cycling and proliferation; antibodies to Ki67 are commercially available, such as from ABCAM®, and methods are available to use these antibodies in immunohistochemical and FACS analyses.

Other methods can be used to detect those cells that are in the active cell cycle at the time of sampling. Proliferation of lymphocytes, such as CD39+CD8+ T cells, for example CD39+ CD103+ CD8 T cells, can also be measured by using methods that utilize stable isotopes to label DNA in biological samples including cells. DNA is uniformly and highly labeled via the de novo synthesis pathway. The stable isotope labels used, e.g. $^2$H-glucose or heavy water ($^2$H$_2$O or H$_2$$^{18}$O), are non-toxic to animals and humans, and generally regarded as safe by the US Food and Drug Administration (FDA) (see U.S. Patent Application Publication No. 2009/0155179). The measurement of stable isotope label incorporation into lymphocyte DNA comprises the following steps: (i) extraction of DNA or its release from chromatin without further isolation, hydrolysis of DNA to deoxyribonucleotides, (ii) selective release of deoxyribose from purine deoxyribonucleotides, (iii) derivatization of purine deoxyribose to a volatile derivative (e.g., pentane tetraacetate, pentafluorobenzyl tetraacetyl derivative, or another suitable derivative) suitable for analysis by gas chromatography/mass spectrometry (GC/MS), (iv) GC/MS analysis of said derivative, (v) analysis of the pattern of mass isotopomer abundance of said derivative, and (vi) calculation from said pattern of an excess enrichment value that is a measure of stable isotope incorporation. Specific embodiments of each of these methods have been taught (see U.S. Pat. No. 591,040).

PD-1, CTLA-4, TIM-3, LAG3, BTLA Antagonists and 4-1BB Agonists

Check-point inhibitors, such as PD-1 antagonists, PD-L1 antagonists, CTLA-4 antagonists, LAG3 antagonists, TIM-3 antagonists and/or BTLA antagonists are of use in the method disclosed herein, for example in combination with CD8+CD39+CD103+ T cells. 4-1BB agonists are also of use in the method disclosed herein. The PD-1 antagonist, PD-L1 antagonist, CTLA-4 antagonist, LAG3 antagonist, TIM-3 antagonist, BTLA antagonist, and/or 4-1BB agonist can be a chemical or biological compound. The agent can be an antibody, including but not limited to a chimeric, humanized, or human antibody. Suitable antagonists and agonists also include antigen binding fragments of these antibodies (see above for a description of antigen binding fragments). The antagonist can be, for example, an inhibitor nucleic acid molecule or a small molecule, such as a molecule less than 900 daltons or less than 800 daltons.

A PD-1 antagonist can be any chemical compound or biological molecule that blocks binding of PD-L1 or PD-L2 expressed on a cell to human PD-1 expressed on an immune cell (T cell, B cell or NKT cell). Alternative names or synonyms for PD-1 and its ligands include: PDCD1, PD1, CD279 and SLEB2 for PD-1; PDCD1L1, PD-L1, B7H1, B7-4, CD274 and B7-H for PD-L; and PDCD1L2, PDL2, B7-DC, Btdc and CD273 for PD-L2. Exemplary human PD-1 amino acid sequences can be found in NCBI Accession No.: NP_005009. Exemplary human PD-L1 and PD-L2 amino acid sequences can be found in NCBI Accession No.: NP_054862 and NP_079515, respectively, Apr. 28, 2017, incorporated by reference. In vivo, PD-1 is expressed on activated T cells, B cells, and monocytes. In humans, PD-1 is a 50-55 kDa type I transmembrane receptor that was originally identified in a T cell line undergoing activation-induced apoptosis. PD-1 is expressed on T cells, B cells, and macrophages. The ligands for PD-1 are the B7 family members PD-ligand 1 (PD-L1, also known as B7-H1) and PD-L2 (also known as B7-DC). A PD-L1 or PD-L2 inhibitor can be used in the methods disclosed herein.

Experimental data implicates the interactions of PD-1 with its ligands in downregulation of central and peripheral immune responses. In particular, proliferation in wild-type T cells but not in PD-1-deficient T cells is inhibited in the presence of PD-L1. (See e.g., Ishida et al., EMBO J. 11:3887, 1992; Shinohara et al. Genomics 23:704, 1994; U.S. Pat. No. 5,698,520, incorporated herein by reference).

Additional PD-1 amino acid sequences are disclosed in U.S. Pat. No. 6,808,710 and U.S. Patent Application Publication Nos. 2004/0137577, 2003/0232323, 2003/0166531, 2003/0064380, 2003/0044768, 2003/0039653, 2002/0164600, 2002/0160000, 2002/0110836, 2002/0107363, and 2002/0106730, which are incorporated herein by reference.

PD-1 is a member of the CD28/CTLA-4 family of molecules based on its ability to bind to PD-L1. In vivo, like CTLA-4, PD-1 is rapidly induced on the surface of T-cells in response to anti-CD3 (Agata et al. Int. Immunol. 8:765, 1996). T cell exhaustion is concomitant with an induction in PD-1 expression, see PCT Publication No. 2008/083174, incorporated herein by reference. T-cell cytotoxicity can be increased by contacting a T-cell with an agent that reduces the expression or activity of PD-1. An agent that reduces the expression or activity of PD-1 can be used to increase an immune response, such as to a tumor. Without being bound by theory, reduction of PD-1 expression or activity results in an increase in cytotoxic T cell activity, increasing the specific immune response.

PD-1 family members bind to one or more receptors, such as PD-L1 and PD-L2 on antigen presenting cells. An exemplary amino acid sequence for PD-L1 is provided as GENBANK® Accession No. AAG18508, which is incorporated by reference herein as available Oct. 4, 2000. An exemplary PD-L2 precursor amino acid sequence is provided as GENBANK® Accession No. AAK15370, which is incorporated by reference herein as available Apr. 8, 2002. An exemplary variant PD-L2 precursor amino acid sequence is provided as GENBANK® Accession No. Q9BQ51, which is incorporated by reference herein as available Dec. 12, 2006.

Antagonists of use in the methods disclosed herein include agents that reduce the expression or activity of a PD ligand 1 (PD-L1) or a PD ligand 2 (PD-L2) or reduces the interaction between PD-1 and PD-L1 or the interaction between PD-1 and PD-L2; these are PD-antagonists. Exemplary compounds include antibodies (such as an anti-PD-1 antibody, an anti-PD-L1 antibody, and an anti-PD-L2 antibody), RNAi molecules (such as anti-PD-1 RNAi molecules, anti-PD-L1 RNAi, and an anti-PD-L2 RNAi), antisense molecules (such as an anti-PD-1 antisense RNA, an anti-PD-L1 antisense RNA, and an anti-PD-L2 antisense RNA), dominant negative proteins (such as a dominant negative PD-1 protein, a dominant negative PD-L1 protein, and a dominant negative PD-L2 protein), and small molecule inhibitors. Any of these PD-1 antagonists are of use in the methods disclosed herein.

Other antibodies are of use in the methods disclosed herein (such as an anti-CTLA-4 antibody, and anti-LAG3 antibody, an-anti-TIM-3 antibody or an anti-BTLA antibody), RNAi molecules (such as anti-CTLA-4 RNAi molecules, anti-LAG3 RNAi, anti-TIM-3 RNAi and an anti-BTLA RNAi), antisense molecules (such as an anti-CTLA-4 antisense RNA, anti-LAG3 antisense RNA, anti-TIM-3 antisense RNA and an anti-BTLA antisense RNA). Dominant negative proteins also of use are a dominant negative CTLA-4 protein, a dominant negative LAG3 protein, a dominant negative LAG-3 protein and a dominant negative BTLA protein). Any of these antagonists are of use in the methods disclosed herein. In addition, 4-1BB agonists, such as antibodies that bind 4-1BB and RNA Aptamers, are of use in the methods disclosed herein. A TGF-β receptor inhibitory or dominant negative protein is also of use.

An antagonist is an agent having the ability to reduce the expression or the activity of the target in a cell. In some embodiments, PD-1, PD-L1, PD-L2, LAG3, TIM-3, CTLA-4 or BTLA expression or activity is reduced by at least about 10%, 20%, 30%, 40%, 50%, 60%, 70%, 80%, 90%, or 100% compared to such expression or activity in a control. Exemplary reductions in activity are at least about 50%, at least about 60%, at least about 70%, at least about 80%, at least about 90%, at least about 95%, or a complete absence of detectable activity. In one example, the control is a cell that has not been treated with the PD-1 antagonist. In another example, the control is a standard value, or a cell contacted with an agent, such as a carrier, known not to affect activity. Expression or activity can be determined by any standard method in the art. In one non-limiting example, a PD-1 antagonist inhibits or reduces binding of PD-1 to PD-L1, PD-L2, or both. In one non-limiting example, a PD-L1 antagonist reduces the binding of PD-L1 or PD-1.

An agonist is an agent having the ability to increase the expression or the activity of the target in a cell. In some embodiments, 4-1BB expression or activity is increased by at least about 10%, 20%, 30%, 40%, 50%, 60%, 70%, 80%, 90%, or 100% compared to such expression or activity in a control. Exemplary increases in activity are at least about 50%, at least about 60%, at least about 70%, at least about 80%, at least about 90%, at least about 95%, or a complete absence of detectable activity. In one example, the control is a cell that has not been treated with the 4-1BB agonist. In another example, the control is a standard value, or a cell contacted with an agent, such as a carrier, known not to affect activity. Expression or activity can be determined by any standard method in the art. In one non-limiting example, 4-1BB agonist stimulates or increases binding.

A. Antibodies

In some embodiments, the antagonist is an antibody. Exemplary amino acid sequence of antibodies that bind PD-1 are disclosed, for example, in U.S. Patent Publication No. 2006/0210567, which is incorporated herein by reference. Antibodies that bind PD-1 are also disclosed in U.S. Patent Publication No. 2006/0034826, which is also incorporated herein by reference. Antibodies that bind PD-1 are also disclosed in U.S. Pat. Nos. 7,488,802, 7,521,051, 8,008, 449, 8,354,509, 8,168,757, and U.S. PCT Publication No. WO2004/004771, PCT Publication No. WO2004/072286, PCT Publication No. WO2004/056875, and US Published Patent Application No. 2011/0271358. The antibody can be KEYTRUDA® (pembrolizumab). The antibody can be an anti-PD-1 antibody such as Nivolumab (ONO-4538/BMS-936558) or OPDIVO® from Ono Pharmaceuticals. PD-L1 binding antagonists include YW243.55.570, MPDL3280A, MDX-1105 and MEDI 4736, see U.S. Published Patent Application No. 2017/0044256. Examples of monoclonal antibodies that specifically bind to human PD-L1, and are useful in the disclosed methods and compositions are disclosed in PCT Publication No. WO2013/019906, PCT Publication No. WO2010/077634 A1 and U.S. Pat. No. 8,383, 796. The checkpoint inhibitor antibodies against PD-1 (e.g., Nivolumab, pidilizumab, and Pembrolizumab) or PD-L1 (e.g., Durvalumab, Atezolizumab, and Avelumab) are of use in any of the methods disclosed herein. Antibodies that bind PD-1, PD-L2 and PD-1 are also disclosed in U.S. Pat. No. 8,552,154. In several examples, the antibody specifically binds CTLA-4, BTLA, PD-1, PD-L1, or PD-L2 with an affinity constant of at least $10^7$ M$^{-1}$, such as at least $10^8$ M$^{-1}$ at least $5 \times 10^8$ M$^{-1}$ or at least $10^9$ M$^{-1}$. Any of these antibodies, and antigen binding fragments, are of use in the methods disclosed herein.

Exemplary antibodies that specifically bind CTLA-4 are disclosed in PCT Publication No. WO 2001/014424, PCT Publication No. WO 2004/035607, U.S. Publication No. 2005/0201994, European Patent No. EP 1141028, and European Patent No. EP 1212422 B1. Additional CTLA-4 antibodies are disclosed in U.S. Pat. Nos. 5,811,097, 5,855,887, 6,051,227, 6,984,720, 6,682,736, 6,207,156, 5,977,318, 6,682,736, 7,109,003, 7,132,281, 7,452,535, and 7,605,238; PCT Publication No. WO 01/14424, PCT Publication No. WO 00/37504, PCT Publication No. WO 98/42752, U.S. Published Patent Application No. 2000/037504, U.S. Published Application No. 2002/0039581, and U.S. Published Application No. 2002/086014. Antibodies that specifically bind CTLA-4 are also disclosed in Hurwitz et al., Proc. Natl. Acad. Sci. USA, 95(17):10067-10071 (1998); Camacho et al., J. Clin. Oncol., 22(145): Abstract No. 2505 (2004) (antibody CP-675206); Mokyr et al., Cancer Res., 58:5301-5304 (1998). In some embodiments the CTLA-4 antagonist is Ipilmumab (also known as MDX-010 and MDX-101 and YERVOY®), see PCT Publication No. WO 2001/014424, incorporated herein by reference. These antibodies, and antigen binding fragments, are of use in the methods disclosed herein.

In further embodiments, a BTLA antagonist is utilized in the methods disclosed herein. Antibodies that specifically bind BTLA are disclosed, for example, in U.S. Published Patent Application No. 2016/0222114, U.S. Published Patent Application No. 2015/0147344, and U.S. published Patent Application No. 2012/0288500, all incorporated herein by reference. Biological agents that modulate BTLA activity, specifically using Herpesvirus entry mediator (HVEM) cis complexes are disclosed in U.S. Published Patent Application No. 2014/0220051 and U.S. Published Patent Application No. 2010/0104559, both incorporated herein by reference. In yet other embodiments, the antibody specifically binds TIM-3, such as TSR-022. In further embodiments, the antibody specifically binds LAG3, such as BMS-986016, GSK2831781, or the antibodies disclosed in PCT Publication No. WO2015042246 A1, incorporated herein by reference. See also Clinical trial number NCT01968109 for "Safety Study of Anti-LAG-3 With and Without Anti-PD-1 in the Treatment of Solid Tumors" available on the internet at clinicaltrials.gov and incorporated by reference herein. These antibodies, and antigen binding fragments, are of use in the methods disclosed herein.

A 4-1BB agonist antibody is also of use. Suitable antibodies are disclosed, for example, in U.S. Pat. No. 8,337,850 and PCT Publication No. WO 2015179236 A1, both incorporated by reference herein. Antibodies of use in any of the disclosed methods include urelumab (BMS-663513) and PF-05082566 (Pfizer).

The antibodies of use in the disclosed methods include monoclonal antibodies, humanized antibodies, deimmunized antibodies (such as to reduce a human-anti-mouse response), chimeric antibodies, and immunoglobulin (Ig) fusion proteins. Antigen binding fragments of these antibodies are also of use in the methods disclosed herein. Polyclonal antibodies can be prepared by one of skill in the art, such as by immunizing a suitable subject (such as a veterinary subject) with an immunogen. The antibody titer in the immunized subject can be monitored over time by standard techniques, such as with an enzyme linked immunosorbent assay (ELISA) using immobilized antigen. In one example, an antibody that specifically bind CTLA-4, BTLA, TIM-3, LAG3, PD-1, PD-L1, or PD-L2 (or combinations thereof) can be isolated from the mammal (such as from serum) and further purified by techniques known to one of skill in the art. For example, antibodies can be purified using protein A chromatography to isolate IgG antibodies.

Antibody-producing cells can be obtained from the subject and used to prepare monoclonal antibodies by standard techniques (see Kohler and Milstein Nature 256:495 49, 1995; Brown et al., J. Immunol. 127:539 46, 1981; Cole et al., Monoclonal Antibodies and Cancer Therapy, Alan R. Liss, Inc., pp. 77 96, 1985; Gefter, M. L. et al. (1977) Somatic Cell Genet. 3:231 36; Kenneth, R. H. in Monoclonal Antibodies: A New Dimension In Biological Analyses. Plenum Publishing Corp., New York, N.Y. (1980); Kozbor et al. Immunol. Today 4:72, 1983; Lerner, E. A. (1981) Yale J. Biol. Med. 54:387 402; Yeh et al., Proc. Natl. Acad. Sci. 76:2927 31, 1976). In one example, an immortal cell line (typically a myeloma) is fused to lymphocytes (typically splenocytes) from a mammal immunized with PD-1, PD-L1, PD-L2, TIM-3, LAG3, BTLA or CTLA-4 and the culture supernatants of the resulting hybridoma cells are screened to identify a hybridoma producing a monoclonal antibody that specifically binds to the polypeptide of interest.

In one embodiment, to produce a hybridoma, an immortal cell line (such as a myeloma cell line) is derived from the same mammalian species as the lymphocytes. For example, murine hybridomas can be made by fusing lymphocytes from a mouse immunized with a CTLA-4, BTLA, TIM-3, LAG3, PD-1, PD-L1, PD-L2, or 4-1BB peptide with an immortalized mouse cell line. In one example, a mouse myeloma cell line is utilized that is sensitive to culture medium containing hypoxanthine, aminopterin and thymidine ("HAT medium"). Any of a number of myeloma cell lines can be used as a fusion partner according to standard techniques, including, for example, P3-NS1/1-Ag4-1, P3-x63-Ag8.653 or Sp2/O-Ag14 myeloma lines, which are available from the American Type Culture Collection (ATCC), Rockville, Md. HAT-sensitive mouse myeloma cells can be fused to mouse splenocytes using polyethylene glycol ("PEG"). Hybridoma cells resulting from the fusion are then selected using HAT medium, which kills unfused (and unproductively fused) myeloma cells. Hybridoma cells producing a monoclonal antibody of interest can be detected, for example, by screening the hybridoma culture supernatants for the production antibodies that bind a PD-1, PD-L1, TIM-3, LAG3, BTLA, CTLA-4, PD-L2 or 4-1BB molecule, such as by using an immunological assay (such as an enzyme-linked immunosorbant assay (ELISA) or radioimmunoassay (RIA).

As an alternative to preparing monoclonal antibody-secreting hybridomas, a monoclonal antibody that specifically binds CTLA-4, BTLA, TIM-3, LAG3, PD-1, PD-L1, PD-L2 or 4-1BB can be identified and isolated by screening a recombinant combinatorial immunoglobulin library (such as an antibody phage display library) with CTLA-4, BTLA, TIM-3, LAG3, PD-1, PD-L1, PD-L2 or 4-BB to isolate immunoglobulin library members that specifically bind the polypeptide. Kits for generating and screening phage display libraries are commercially available (such as, but not limited to, Pharmacia and Stratagene). Examples of methods and reagents particularly amenable for use in generating and screening antibody display library can be found in, for example, U.S. Pat. No. 5,223,409; PCT Publication No. WO 90/02809; PCT Publication No. WO 91/17271; PCT Publication No. WO 92/18619; PCT Publication WO 92/20791; PCT Publication No. WO 92/15679; PCT Publication No. WO 92/01047; PCT Publication WO 93/01288; PCT Publication No. WO 92/09690; Barbas et al., Proc. Natl. Acad. Sci. USA 88:7978 7982, 1991; Hoogenboom et al., Nucleic Acids Res. 19:4133 4137, 1991.

In one example the sequence of the specificity determining regions of each CDR is determined. Residues are outside the SDR (non-ligand contacting sites) are substituted. For example, in any of the CDR sequences as in the table above, at most one, two or three amino acids can be substituted. The production of chimeric antibodies, which include a framework region from one antibody and the CDRs from a different antibody, is well known in the art. For example, humanized antibodies can be routinely produced. The antibody or antibody fragment can be a humanized immunoglobulin having complementarity determining regions (CDRs) from a donor monoclonal antibody that binds CTLA-4, BTLA, TIM-3, LAG3, PD-1, PD-L1, PD-L2, or 4-1BB and immunoglobulin and heavy and light chain variable region frameworks from human acceptor immunoglobulin heavy and light chain frameworks. Humanized monoclonal antibodies can be produced by transferring donor complementarity determining regions (CDRs) from heavy and light variable chains of the donor mouse immunoglobulin (such a CTLA-4, BTLA, TIM-3, LAG3, PD-1, PD-L1, PD-L2 or 4-1BB specific antibody) into a human variable domain, and then substituting human residues in the framework regions when required to retain affinity. The use of antibody components derived from humanized monoclonal antibodies obviates potential problems associated with the immunogenicity of the constant regions of the donor antibody. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Natl. Acad Sci. U.S.A.* 89:4285, 1992; Sandhu, *Crit. Rev. Biotech.* 12:437, 1992; and Singer et al., *J. Immunol.* 150: 2844, 1993. The antibody may be of any isotype, but in several embodiments the antibody is an IgG, including but not limited to, $IgG_1$, $IgG_2$, $IgG_3$ and $IgG_4$. In some embodiments, the humanized immunoglobulin specifically binds to the antigen of interest (e.g., CTLA-4, BTLA, TIM-3, LAG3, PD-1, PD-L1, PD-L2, or 4-1BB) with an affinity constant of at least $10^7$ $M^{-1}$, such as at least $10^8$ $M^{-1}$ at least $5\times10^8$ $M^{-1}$ or at least $10^9$ $M^{-1}$.

In one embodiment, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 99% or at least about 95%, identical to the sequence of the donor immunoglobulin heavy chain variable region framework. Human framework regions, and mutations that can be made in humanized antibody framework regions, are known in the art (see, for example, in U.S. Pat. No. 5,585,089, which is incorporated herein by reference).

Antibodies, such as murine monoclonal antibodies, chimeric antibodies, and humanized antibodies, include full length molecules as well as fragments thereof, such as Fab, $F(ab')_2$, and Fv which include a heavy chain and light chain variable region and are capable of binding specific epitope determinants. These antibody fragments retain some ability to selectively bind with their antigen or receptor. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

Methods of making these antigen binding fragments are known in the art (see for example, Harlow and Lane, *Antibodies: A Laboratory Manual*, Cold Spring Harbor Laboratory, New York, 1988). In several examples, the variable region includes the variable region of the light chain and the variable region of the heavy chain expressed as individual polypeptides. Fv antibodies are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra).

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Thus, one of skill in the art can readily review the amino acid sequence of an antibody of interest, locate one or more of the amino acids in the brief table above, identify a conservative substitution, and produce the conservative variant using well-known molecular techniques.

Effector molecules, such as therapeutic, diagnostic, or detection moieties can be linked to an antibody that specifically binds CTLA-4, BTLA, TIM-3, LAG3, PD-1, PD-L1, PD-L2, or 4-1BB using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

Nucleic acid sequences encoding the antibodies can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding sequences encoding an antibody that specifically binds CTLA-4, BTLA, TIM-3, LAG3, PD-1, PD-L1, PD-L2, or 4-1BB can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, an antibody of use is prepared by inserting the cDNA which encodes a variable region from an antibody that specifically binds CTLA-4, BTLA, TIM-3, LAG3, PD-1, PD-L, PD-L2, or 4-1BB into a vector which comprises the cDNA encoding an effector molecule (EM). The insertion is made so that the variable region and the EM are read in frame so that one continuous polypeptide is produced. Thus, the encoded polypeptide contains a functional Fv region and a functional EM region. In one embodiment, cDNA encoding a detectable marker (such as an enzyme) is ligated to a scFv so that the marker is located at the carboxyl terminus of the scFv. In another example, a detectable marker is located at the amino terminus of the scFv. In a further example, cDNA encoding a detectable marker is ligated to a heavy chain variable region of an antibody that specifically binds CTLA-4, BTLA, TIM-3, LAG3, PD-1, PD-L1, PD-L2, or 4-1BB so that the marker is located at the carboxyl terminus of the heavy chain variable region. The heavy chain-variable region can subsequently be ligated to a light chain variable region of the antibody that specifically binds CTLA-4, BTLA, TIM-3, LAG3, PD-1, PD-L1, PD-L2, or 4-1BB using disulfide bonds. In a yet another example, cDNA encoding a marker is ligated to a light chain variable region of an antibody that binds CTLA-4, BTLA, TIM-3, LAG3, PD-1, PD-L1, PD-L2, or 4-1BB, so that the marker is located at the carboxyl terminus of the light chain variable region. The light chain-variable region can subsequently be ligated to a heavy chain variable region of the antibody that specifically binds CTLA-4, BTLA, TIM-3, LAG3, PD-1, PD-L1, PD-L2, or 4-1BB using disulfide bonds.

Once the nucleic acids encoding the antibody or functional fragment thereof are isolated and cloned, the protein can be expressed in a recombinantly engineered cell such as bacteria, plant, yeast, insect and mammalian cells. One or more DNA sequences encoding the antibody or functional fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding the antibody or functional fragment thereof can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the antibody or functional fragment thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as $E.$ $coli$, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody of functional fragment thereof and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the recombinant antibodies can be purified according to standard procedures of the art, including ammonium sulfate precipitation, affinity columns, column chromatography, and the like (see, generally, R. Scopes, Protein Purification, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

In addition to recombinant methods, the antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis*, Part A. pp. 3-284; Merrifield et al., *J. Am. Chem. Soc.* 85:2149-2156, 1963, and Stewart et al., *Solid Phase Peptide Synthesis, 2nd ed.*, Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicyclohexylcarbodimide) are well known in the art.

B. Inhibitory Nucleic Acids

Inhibitory nucleic acids that decrease the expression and/or activity of CTLA-4, BTLA, TIM-3, LAG3, PD-1, PD-L1, or PD-L2 can also be used in the methods disclosed herein. One embodiment is a small inhibitory RNA (siRNA) for interference or inhibition of expression of a target gene. Nucleic acid sequences encoding PD-1, PD-L1 and PD-L2 are disclosed in GENBANK® Accession Nos. NM_005018, AF344424, NP_079515, and NP_054862, all incorporated by reference as available on Apr. 28, 2017.

Generally, siRNAs are generated by the cleavage of relatively long double-stranded RNA molecules by Dicer or DCL enzymes (Zamore, *Science*, 296:1265-1269, 2002; Bernstein et al., *Nature*, 409:363-366, 2001). In animals and plants, siRNAs are assembled into RISC and guide the sequence specific ribonucleolytic activity of RISC, thereby resulting in the cleavage of mRNAs or other RNA target molecules in the cytoplasm. In the nucleus, siRNAs also guide heterochromatin-associated histone and DNA methylation, resulting in transcriptional silencing of individual genes or large chromatin domains. PD-1 siRNAs are commercially available, such as from Santa Cruz Biotechnology, Inc.

The present disclosure provides RNA suitable for interference or inhibition of expression of a target gene, which RNA includes double stranded RNA of about 15 to about 40 nucleotides containing a 0 to 5-nucleotide 3' and/or 5' overhang on each strand. The sequence of the RNA is substantially identical to a portion of an mRNA or transcript of a target gene, such as CTLA-4, BTLA, TIM-3, LAG3, PD-1, PD-L1, or PD-L2, for which interference or inhibition of expression is desired. For purposes of this disclosure, a sequence of the RNA "substantially identical" to a specific portion of the mRNA or transcript of the target gene for which interference or inhibition of expression is desired differs by no more than about 30 percent, and in some embodiments no more than about 10 percent, from the specific portion of the mRNA or transcript of the target gene. In particular embodiments, the sequence of the RNA is exactly identical to a specific portion of the mRNA or transcript of the target gene.

Thus, siRNAs disclosed herein include double-stranded RNA of about 15 to about 40 nucleotides in length and a 3' or 5' overhang having a length of 0 to 5-nucleotides on each strand, wherein the sequence of the double stranded RNA is substantially identical to (see above) a portion of a mRNA or transcript of a nucleic acid encoding CTLA-4, BTLA, TIM-3, LAG3, PD-1, PD-L1, or PD-L2. In particular examples, the double stranded RNA contains about 19 to about 25 nucleotides, for instance 20, 21, or 22 nucleotides substantially identical to a nucleic acid encoding CTLA-4, BTLA, TIM-3, LAG3, PD-1, PD-L1, or PD-L2. In additional examples, the double stranded RNA contains about 19 to about 25 nucleotides 100% identical to a nucleic acid encoding CTLA-4, BTLA, TIM-3, LAG3, PD-1, PD-L1, or PD-L2. It should be not that in this context "about" refers to integer amounts only. In one example, "about" 20 nucleotides refers to a nucleotide of 19 to 21 nucleotides in length.

Regarding the overhang on the double-stranded RNA, the length of the overhang is independent between the two strands, in that the length of one overhang is not dependent on the length of the overhang on other strand. In specific examples, the length of the 3' or 5' overhang is 0-nucleotide on at least one strand, and in some cases it is 0-nucleotide on both strands (thus, a blunt dsRNA). In other examples, the length of the 3' or 5' overhang is 1-nucleotide to 5-nucleotides on at least one strand. More particularly, in some examples the length of the 3' or 5' overhang is 2-nucleotides on at least one strand, or 2-nucleotides on both strands. In particular examples, the dsRNA molecule has 3' overhangs of 2-nucleotides on both strands.

Thus, in one particular provided RNA embodiment, the double-stranded RNA contains 20, 21, or 22 nucleotides, and the length of the 3' overhang is 2-nucleotides on both strands. In embodiments of the RNAs provided herein, the double-stranded RNA contains about 40-60% adenine+uracil (AU) and about 60-40% guanine+cytosine (GC). More particularly, in specific examples the double-stranded RNA contains about 50% AU and about 50% GC.

Also described herein are RNAs that further include at least one modified ribonucleotide, for instance in the sense strand of the double-stranded RNA. In particular examples, the modified ribonucleotide is in the 3' overhang of at least one strand, or more particularly in the 3' overhang of the sense strand. It is particularly contemplated that examples of modified ribonucleotides include ribonucleotides that include a detectable label (for instance, a fluorophore, such as rhodamine or FITC), a thiophosphate nucleotide analog, a deoxynucleotide (considered modified because the base molecule is ribonucleic acid), a 2'-fluorouracil, a 2'-aminouracil, a 2'-aminocytidine, a 4-thiouracil, a 5-bromouracil, a 5-iodouracil, a 5-(3-aminoallyl)-uracil, an inosine, or a 2'O-Me-nucleotide analog.

Antisense and ribozyme molecules for CTLA-4, BTLA, TIM-3, LAG3, PD-1, PD-L1, or PD-L2 are also of use in the method disclosed herein. Antisense nucleic acids are DNA or RNA molecules that are complementary to at least a portion of a specific mRNA molecule (Weintraub, *Scientific American* 262:40, 1990). In the cell, the antisense nucleic acids hybridize to the corresponding mRNA, forming a double-stranded molecule. The antisense nucleic acids interfere with the translation of the mRNA, since the cell will not translate an mRNA that is double-stranded. Antisense oligomers of about 15 nucleotides are preferred, since they are easily synthesized and are less likely to cause problems than larger molecules when introduced into the target cell producing CTLA-4, BTLA, TIM-3, LAG3, PD-1, PD-L1, or PD-L2. The use of antisense methods to inhibit the in vitro translation of genes is well known in the art (see, for example, Marcus-Sakura, *Anal. Biochem.* 172:289, 1988).

An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid molecule can be chemically synthesized using naturally occurring nucleotides or variously modified nucleotides designed to increase the biological stability of the molecules or to increase the physical stability of the duplex formed between the antisense and sense nucleic acids, such as phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridin- e, 5-carboxymethylaminomethyluracil, dihydrouracil, beta-D-galactosylqueosine, inosine, amongst others.

Use of an oligonucleotide to stall transcription is known as the triplex strategy since the bloomer winds around double-helical DNA, forming a three-strand helix. Therefore, these triplex compounds can be designed to recognize a unique site on a chosen gene (Maher, et al., *Antisense Res. and Dev.* 1(3):227, 1991; Helene, C., *Anticancer Drug Design* 6(6):569), 1991. This type of inhibitory oligonucleotide is also of use in the methods disclosed herein.

Ribozymes, which are RNA molecules possessing the ability to specifically cleave other single-stranded RNA in a manner analogous to DNA restriction endonucleases, are also of use. Through the modification of nucleotide sequences which encode these RNAs, it is possible to engineer molecules that recognize specific nucleotide sequences in an RNA molecule and cleave it (Cech, *J. Amer. Med. Assn.* 260:3030, 1988). A major advantage of this approach is that, because they are sequence-specific, only mRNAs with particular sequences are inactivated.

There are two basic types of ribozymes namely, tetrahymena-type (Hasselhoff, *Nature* 334:585, 1988) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences.

Various delivery systems are known and can be used to administer the siRNAs and other inhibitory nucleic acid molecules as therapeutics. Such systems include, for example, encapsulation in liposomes, microparticles, microcapsules, nanoparticles, recombinant cells capable of expressing the therapeutic molecule(s) (see, e.g., Wu et al., *J. Biol. Chem.* 262, 4429, 1987), construction of a therapeutic nucleic acid as part of a retroviral or other vector, and the like.

C. Small Molecules

CTLA-4, BTLA, TIM-3, LAG3, PD-1, PD-L1, or PD-L2 antagonists, and 4-1BB agonist, include molecules that are identified from large libraries of both natural product or synthetic (or semi-synthetic) extracts or chemical libraries according to methods known in the art. The screening methods that detect decreases in CTLA-4, BTLA, TIM-3, LAG3, PD-1, PD-L1, or PD-L2 activity (such as detecting cell death for PD-1, PD-L1 and PD-L2) are useful for identifying compounds from a variety of sources for activity. Screening methods that detect increases in 4-1BB activity are also of use for identifying compounds from such sources. The initial screens may be performed using a diverse library of compounds, a variety of other compounds and compound libraries. Thus, molecules that bind CTLA-4, BTLA, TIM-3, LAG3, PD-1, PD-L1, or PD-L2 molecules that inhibit the expression of CTLA-4, BTLA, TIM-3, LAG3, PD-1, PD-L1, or PD-L2 and molecules that inhibit the activity of CTLA-4, BTLA, TIM-3, LAG3, PD-1, PD-L1, or PD-L2 can be identified. Molecules that increase the expression and/or activity of 4-1BB can also be identified. These small molecules can be identified from combinatorial libraries, natural product libraries, or other small molecule libraries. In addition, CTLA-4, BTLA, TIM-3, LAG3, PD-1, PD-L1, and PD-L2 antagonists, and 4-1BB agonists, can be identified as compounds from commercial sources, as well as commercially available analogs of identified inhibitors. In some embodiments, the small molecule is less than 900 daltons, or less than 800 daltons.

The precise source of test extracts or compounds is not critical to the identification of antagonists. Accordingly, antagonists can be identified from virtually any number of chemical extracts or compounds. Examples of such extracts or compounds that can be antagonists include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Agonists and antagonists can be identified from synthetic compound libraries that are commercially available from a number of companies including Maybridge Chemical Co. (Trevillet, Cornwall, UK), Comgenex (Princeton, N. J.), Brandon Associates (Merrimack, N.H.), and Microsource (New Milford, Conn.). CTLA-4, BTLA, TIM-3, LAG3, PD-1, PD-L1, and PD-L2 antagonists, or 4-1BB agonists, can be identified from a rare chemical library, such as the library that is available from Aldrich (Milwaukee, Wis.). CTLA-4, BTLA, TIM-3, LAG3, PD-1, PD-L1, and PD-L2 antagonists, or 4-1BB agonists, can be identified in libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 daltons, such as less than about 750 or less than about 350 daltons can be utilized in the methods disclosed herein. Exemplary classes include heterocycles, peptides, saccharides, steroids, and the like. The compounds may be modified to enhance efficacy, stability, pharmaceutical compatibility, and the like. In several embodiments, compounds of use has a Kd for CTLA-4, BTLA, TIM-3, LAG3, PD-1, PD-L1, or PD-L2 of less than 1 nM, less than 10 nm, less than 1 µM, less than 10 µM, or less than 1 mM.

D. Peptide Variants

An immunoadhesin that specifically binds to human CTLA-4, human BTLA, human TIM-3, human LAG3, human PD-1, human PD-L1, or human PD-L2 can also be utilized. An immunoadhesin is a fusion protein containing the extracellular or a binding portion of a protein fused to a constant region such as an Fc region of an immunoglobulin molecule. Examples of immunoadhesion molecules that specifically bind to PD-1 are disclosed in PCT Publication Nos. WO2010/027827 and WO2011/066342, both incorporated by reference. These immunoadhesion molecules include AMP-224 (also known as B7-DCIg), which is a PD-L2-FC fusion protein. Additional PD-1 antagonists that are fusion proteins are disclosed, for example, in U.S. Published Patent Application No. 2014/0227262, incorporated herein by reference.

In one embodiment, a LAG3 antagonist of use in the disclosed methods is IMP321, a soluble LAG3, which has been used to activate dendritic cells. In another embodiment, aTIM-3 antagonists if use in the disclosed methods is CA-327 (Curis).

A CTLA-4 antagonist can be a dominant negative protein or an immunoadhesins, see for example U.S. Published Patent Application No. 2016/0264643, incorporated herein by reference. Additional anti-CTLA-4 antagonists include any inhibitor, including but not limited to a small molecule, that can inhibit the ability of CTLA-4 to bind to its cognate ligand, disrupt the ability of B7 to CTLA-4, disrupt the ability of CD80 to bind to CTLA-4, disrupt the ability of CD86 to bind to CTLA-4.

In one embodiment, variants of a CTLA-4, BTLA, TIM-3, LAG3, PD-1, PD-L1, or PD-L2 protein which function as an antagonist can be identified by screening combinatorial libraries of mutants, such as point mutants or truncation mutants, of a CTLA-4, BTLA, TIM-3, LAG3, PD-1, PD-L1, or PD-L2 protein to identify proteins with antagonist activity. In one example, the antagonist is a soluble protein.

In further embodiments, variants of 4-1BB that function as an agonist can be identified by screening combinatorial libraries of 4-1BB mutants, such as point mutation or truncation mutants, to identify a protein with agonist activity. The agonist can be a soluble protein.

Thus, a library of CTLA-4, BTLA, TIM-3, LAG3, PD-1, PD-L1, PD-L2, or 4-1BB variants can be generated by combinatorial mutagenesis at the nucleic acid level and is encoded by a variegated gene library. A library of CTLA-4, BTLA, TIM-3, LAG3, PD-1, PD-L1, PD-L2 or 4-1BB variants can be produced by, for example, by enzymatically ligating a mixture of synthetic oligonucleotides into gene sequences such that a degenerate set of potential sequences is expressible as individual polypeptides, or alternatively, as a set of larger fusion proteins (such as for phage display) containing the set of sequences of interest.

There are a variety of methods, which can be used to produce libraries of potential CTLA-4, BTLA, TIM-3, LAG3, PD-1, PD-L1, PD-L2 or 4-1BB variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CTLA-4, BTLA, TIM-3, LAG3, PD-1, PD-L1, PD-L2 or 4-1BB sequences. Methods for synthesizing degenerate oligonucleotides are known in the art (see, for example, Narang, et al., Tetrahedron 39:3, 1983; Itakura et al. Annu. Rev. Biochem. 53:323, 1984; Itakura et al. Science 198: 1056, 1984).

In addition, libraries of fragments of a CTLA-4, BTLA, TIM-3, LAG3, PD-1, PD-L1, PD-L2 or 4-1BB protein coding sequence can be used to generate a population of fragments for screening and subsequent selection of variants of a specified antagonist (or agonist, in the case of 4-1BB). In one embodiment, a library of coding sequence fragments can be generated by treating a double stranded PCR fragment of a CTLA-4, BTLA, TIM-3, LAG3, PD-1, PD-L1, PD-L2, or 4-1BB coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of CTLA-4, BTLA, TIM-3, LAG3, PD-1, PD-L1, PD-L2, or 4-1BB.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM) can be used in combination with the screening assays to identify CTLA-4, BTLA, TIM-3, LAG3, PD-1, PD-L1, or PD-L2 antagonists, or a 4-1BB agonist (Arkin and Youvan, Proc. Natl. Acad. Sci. USA 89:7811 7815, 1992; Delagrave et al., Protein Eng. 6(3):327 331, 1993).

In one embodiment, cell based assays can be exploited to analyze a library of CTLA-4, BTLA, TIM-3, LAG3, PD-1, PD-L1, or PD-L2 variants. For example, a library of expression vectors can be transfected into a cell line, which ordinarily synthesizes and secretes CTLA-4, BTLA, TIM-3, LAG3, PD-1, PD-L1, or PD-L2. The transfected cells are then cultured such that CTLA-4, BTLA, TIM-3, LAG3, PD-1, PD-L1, or PD-L2 and a particular CTLA-4, BTLA, TIM-3, LAG3, PD-1, PD-L1, or PD-L2 (respectively) variant are secreted. The effect of expression of the mutant on activity in cells or in supernatants can be detected, such as by any of a functional assay. Plasmid DNA can then be recovered from the cells wherein endogenous activity is inhibited, and the individual clones further characterized.

Peptidomimetics can also be used as CTLA-4, BTLA, TIM-3, LAG3, PD-1, PD-L1, or PD-L2 antagonists. Peptide analogs are commonly used in the pharmaceutical industry as non-peptide drugs with properties analogous to those of the template peptide. These types of non-peptide compounds and are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (for example, polypeptide that has a PD-1 biological activity), but has one or more peptide linkages optionally replaced by a —CH$_2$NH—, —CH$_2$S—, —CH$_2$—CH$_2$—, —CH=.CH— (cis and trans), —COCH$_2$—, —CH(OH)CH$_2$—, and —CH$_2$SO— linkages. These peptide linkages can be replaced by methods known in the art (see, for example, Morley, Trends Pharm. Sci. pp. 463 468, 1980; Hudson et al. Int. J. Pept. Prot. Res. 14:177 185, 1979; Spatola, Life Sci. 38:1243 1249, 1986; Holladay, et al. Tetrahedron Lett. 24:4401 4404, 1983). Peptide mimetics can be procured economical, be stable, and can have increased have-life or absorption. Labeling of peptidomimetics usually involves covalent attachment of one or more labels, directly or through a spacer (such as by an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization of peptidomimetics should not substantially interfere with the desired biological or pharmacological activity of the peptidomimetic.

A dominant negative protein or a nucleic acid encoding a dominant negative protein that interferes with the biological activity of CTLA-4, BTLA, TIM-3, LAG3, PD-1, PD-L1, or PD-L2 can also be used in the methods disclosed herein. A dominant negative protein is any amino acid molecule having a sequence that has at least 50%, 70%, 80%, 90%, 95%, or even 99% sequence identity to at least 10, 20, 35, 50, 100, or more than 150 amino acids of the wild type protein to which the dominant negative protein corresponds. For example, a dominant-negative PD-L1 has mutation such that it binds PD-1 more tightly than native (wild-type) PD-1 but does not activate any cellular signaling through PD-1.

The dominant negative protein may be administered as an expression vector. The expression vector may be a non-viral vector or a viral vector (e.g., retrovirus, recombinant adeno-associated virus, or a recombinant adenoviral vector). Alternatively, the dominant negative protein may be directly administered as a recombinant protein systemically or to the infected area using, for example, microinjection techniques.

Polypeptide antagonists can be produced in prokaryotic or eukaryotic host cells by expression of polynucleotides encoding the amino acid sequence, frequently as part of a larger polypeptide (a fusion protein, such as with ras or an enzyme). Alternatively, such peptides can be synthesized by chemical methods. Methods for expression of heterologous proteins in recombinant hosts, chemical synthesis of polypeptides, and in vitro translation are well known in the art (see Maniatis el al. Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Kaiser et al., Science 243:187, 1989; Merrifield, Science 232:342, 1986; Kent, Annu. Rev. Biochem. 57:957, 1988).

Peptides can be produced, such as by direct chemical synthesis, and used as antagonists. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (for example, acetylation) or alkylation (for example, methylation) and carboxy-terminal-modifications such as amidation, as well as other terminal modifications, including cyclization, can be incorporated into various embodiments. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others.

The disclosure is illustrated by the following non-limiting Examples.

EXAMPLES

Example 1

Materials and Methods

Healthy Donor Blood Samples and Patient Blood and Tissue Samples:

Peripheral blood, uninvolved lymph nodes, metastatic lymph nodes and tumor samples were obtained from individuals with HNSCC, melanoma, colon cancer, rectal cancer, lung cancer, colorectal liver metastasis and ovarian cancer. All subjects signed written informed consent approved by the institute's Institutional Review Board (Providence Portland Medical Center, IRB).

At the time of sample collection, patients were not undergoing therapy. Previously, they had undergone a wide range of therapies, including chemotherapy, radiotherapy, surgery and immunotherapy, or none of the above.

Peripheral blood mononuclear cells were purified from whole blood over Ficoll-Paque PLUS (GE Healthcare) gradient and cryopreserved prior to analysis.

Tumor specimens were prepared as follows: Briefly, under sterile conditions, tumors were cut into small pieces and digested in RPMI-1640 supplemented with Hyaluronidase at 0.5 mg/ml, Collagenase at 1 mg/ml (both Sigma-Aldrich), DNase at 30 U/ml (Roche) as well as human serum albumin (MP Biomedicals) at 1.5% final concentration. Cells were digested for 1 hr at room temperature under agitation with a magnetic stir bar. Cell suspensions were filtered through a 70 µm filter. Tumor infiltrating lymphocytes were enriched as described above by Ficoll-Paque PLUS density centrifugation. Tumor single-cell suspensions were cryopreserved until further analysis.

Antibodies and Flow Cytometry:

Fluorescently labeled antibodies were purchased from the following manufacturers:

Biolegend: CD3 (UCHT1), CD4 (OKT-4 or RPA-T4), CD8 (RPA-T8), CD25 (BC96), CD38 (HIT2), CD45RA (HI100), CD69 (FN50), HLA-DR (L243), CTLA-4 (BNI3), 4-1BB (4B4-1), CCR7 (G043H7), Granzyme B (GBI 1), IFN-g (4S.B3), TNF-α (Mab11)

BD Bioscience: CD27 (M-T271), CD127 (HIL-7R-M21), PD-1 (EH12), Ki-67 (B56), eBioscience: CD28 (CD28.2), CD39 (eBioA1), CD103 (Ber-ACT8 and B-Ly7), FOXP3 (PCH101), ICOS (ISA-3)

R&D: TIM-3 (344823)

A fixable live/dead dye was used to distinguish viable cells (Biolegend). Cell surface staining was performed in FACS buffer (PBS, supplemented with 1% FBS and 0.01% NaN$_3$). Intracellular staining was performed using the Fix/

Perm kit from eBioscience according to the manufacturer's instructions. To analyze cytokine production by peripheral blood mononuclear cells and TIL ex vivo, cells were stimulated for 5 hrs with PMA (0.2 µM) and Ionomycin (1 µg/ml), with BFA (10 µg/ml) present for the last 2½ hrs. Intracellular cytokine staining was performed using the CytoFix/CytoPerm kit from BD Bioscience according to the manufacturer's instructions. Stained cells were acquired on a LSRII and Fortessa flow cytometer, or the FACS Ariall (all BD), for cell sorting. Data were analyzed with FlowJo software (Treestar).

Cell Sorting and Tcell Expansion:

Cryopreserved PBMC and TIL were thawed and enriched for T lymphocytes using the T cell enrichment kit from Stemcell. For TIL enrichment, Epcam beads (StemCell) were added to the cocktail. The enriched fractions were then labeled and populations of interest were purified after cell sorting to 99% purity on a FACS Ariall (BD).

For TCR sequencing analysis, cell pellets were frozen until further processing.

For expansion of DN CD8+, SP CD8+ and DP CD8+ TIL as well as naïve and memory CD8 from PBMC, T cells were sorted and cultured in complete RPMI-1640, supplemented with 2 mM glutamine, 1% (vol/vol) nonessential amino acids, 1% (vol/vol) sodium pyruvate, penicillin (50 U/ml), streptomycin (50 ug/ml) and 10% fetal bovine serum (Hyclone). T cells (from 2000-5000 cells/well) were stimulated polyclonally with 1 µg/ml PHA (Sigma) in the presence of irradiated (4000 rad) allogeneic feeder cells ($2 \times 10^5$ cells/well) and 10 ng/ml of rh IL-15 (Biolegend) in a 96 well round-bottom plate (Corning/Costar). After 1 week, once T cell clusters formed, cells were split in an additional 96 well plate in complete medium with IL-15, which was repeated again after 2 days, resulting in 4 identical replicates. The four replicates were then pooled in a well of a 24 well plate at day 12. T cell lines were maintained until analysis.

Microarray Data Acquisition:

Samples for micro array were processed in a similar manor to flow analysis. Tumor digest was completed in a 50 ml conical tube with a magnetic stir bar at room temperature for 1 hour with Collagenase at 1 mg/ml (Sigma, C-5138), halyuronidase at 0.5 mg/ml (Sigma, H-6254) in RPMI (Life Technologies, 11875-093) with 0.3% human albumin (MP Biomedicals 823051) and 30 u/ml DNASE (Roche 04536282001). Following digest samples were filtered through a 70 µm filter. Samples were then diluted 1:2 with RPMI and layered onto Ficoll (GE, 17-1440-02) to enrich for lymphocytes through a centrifugation step. Enriched cells were stained for CD3, CD8, CD103, CD39 and sorted using a BD FACSAria cell sorter. Sorted cells were lysed and RNA was purified using Direct-zol RNA miniprep kit (zymo research) RNA was then reverse transcribed to cDNA and amplified. Amplified cDNA was hybridized on a Affymetrix Prime-View gene chip.

Microarray Data Analysis:

CHP files, produced by the Affymetrix GeneChip Command Console (AGCC) v. 3.1.1 and Affymetrix Expression Console v. 1.1 software from the Affymetrix Primeview gene expression array were loaded using the BRB ArrayTools, Version 4.5.1 (available on the internet, brb_nci.nih.gov/BRB-ArrayTools/) software, and annotated with their sample type (i.e. DN, SP, DP). The Affymetrix Quality Control module was run to determine that the expression results were within specifications (applies the BioConductor R module: affy/affyQCReport). Differential expression between sample types was determined using the Class Comparison/Between Groups of Arrays BRBarray module, using a set significance threshold of univariate test (reports least-square and Kolmogorov-Smirnov tests sorted by the p-value of the univariate test). The Graphics/Visualization of Samples module was then used to produce a Multi-Dimensional Analysis of the 3 groups using selected genes (applies the BRBarray R module: MDS.R).

In-Vitro T Cell Activation:

Naïve CD8 T cell subsets were isolated by magnetic CD8 T cell enrichment (Stemcell), labeled with antibodies against CD4, CD8, CD45RA and CCR7 and sorted. $1 \times 10^5$ naïve T cells were cultured with anti-CD3/CD28 Dynabeads (Life Technologies) at a bead:T cell ratio of 1:2 in the presence or absence of 2 ng/ml rh TGFβ-1 (R&D). After 24 hours, beads were removed by magnetic capture for half of the experiment. Expression of activation and differentiation markers was assessed at days 1, 2, 3, 4, 7 and 9.

Deep TCR Sequencing of TCR VB Gene and Clonality Analysis:

Deep sequencing of the variable V-J or V-D-J regions of TCRβ genes was performed on genomic DNA of sorted T cell populations. DNA was extracted from circulating and tumor-resident CD8 T cell subsets ranging from $1 \times 10^4$-$1 \times 10^5$ cells (DNeasy Blood and Tissue Kit, Qiagen). The TCRβ CDR3 regions were sequenced and mapped (ImmunoSEQ, Adaptive Biotech). Coverage per sample was >10×. Only data from productive rearrangements were extracted from the ImmunoSEQ Analyzer platform for further analysis. Clonality of the different T cell subsets was assessed by nucleotide sequence comparison of the 500 most abundant clones in each subset.

To compare the TCR VP overlap (or similarity) of two given populations, we used the Morisita's overlap index. The Morisita-Horn similarity index accounts for both, the number of common clonotypes and the distribution of clonotype sizes, and it is most sensitive to the clone sizes of the dominant clonotypes (ref Venturi et al., J Immunologi Meth, 2008).

Assessment of Target Cell Recognition: 4-1BB and CD25 Up-Regulation and IFN-γ Secretion:

Upregulation of 4-1BB and CD25 as well as release of IFN-γ were used as measures to assess recognition of tumor cells by expanded autologous CD8 T cells. The coculture experiment was performed 17-20 days after beginning the expansion. The day before, expanded T cell were counted and starved overnight in medium without IL-15 to down-regulate remaining expression of 4-1BB and CD25. Expanded CD8 T cells ($1 \times 10^5$) were then cultured either alone or with tumor cells (autologous and allogeneic, ratio T cells: target cells=10:1). In some conditions, tumor cells were preincubated with 30 ug/ml of anti-MHC class I blocking antibody (BD Bioscience, clone W6/32) for 3 h prior to adding T cells. As positive control, Nunc Maxisorp plates were coated with anti-CD3 antibody (OKT3) and T cells were added. All conditions were plated in triplicate. After 24 hrs, supernatants were harvested and analyzed by cytometric bead array (CBA) analysis. Cells were pooled for each condition and labeled with a viability dye, followed by CD39, CD103, CD25 and 4-1BB cell surface staining. Cells were analyzed by flow cytometry. For the CBA, the manufacturer's protocol was followed. In particular, IFN-γ and TNF-α were analyzed.

Live Target Cell Killing Assay:

T cell-mediated target cell killing assays were performed in the Incucyte Zoom System housed inside a cell incubator at 37° C./5% $CO_2$, based on the manufacturer's protocol (Essen Bioscience). To assess T cell killing of autologous tumor cells, 5000-10000 tumor cells (autologous and allogeneic tumor cell lines) were seeded in triplicate into a 96-well flat-bottom plate to reach 10% confluence. Expanded autologous T cell subsets were counted and starved o.n. without exogenous IL-15. $1\times10^5$ T cells were then cultured with and without autologous and allogeneic tumor cells (ratio T cells: Tumor cells=10:1). In some conditions, anti-MHC class I antibody (BD Bioscience, clone W6/32) was added. In all conditions, NucView 488 Caspase 3/7 substrate (Essen Bioscience) was added to monitor active Caspase 3/7. Plates were incubated for 24 hrs at 37° C. and four images were captured from three experimental replicates every hour using a 10× objective lens to visualize T cell killing and caspase 3/7 activity (green fluorescence). Green channel acquisition time was 400 ms. For phase contrast, cell segmentation was achieved by applying a mask in order to exclude the smaller T cells. An area filter was applied to exclude objects below 1000 μm². Green background noise was subtracted with the Top-Hat method of background non-uniformity correction with a radius of 20 μm and a threshold of 2 green corrected units. Fluorescence signal was quantified after applying the mask to the experiment. Amount of T cell killing/apoptosis was calculated by the Zoom software provided (Essen Bioscience).

Statistical Analysis:

Statistical tests were performed using Prism software (GraphPad, San Diego Calif.). Significance was determined by one-way ANOVA analysis with Tukey correction, as noted in figure legends.

Example 2

Results

Figure 1B:
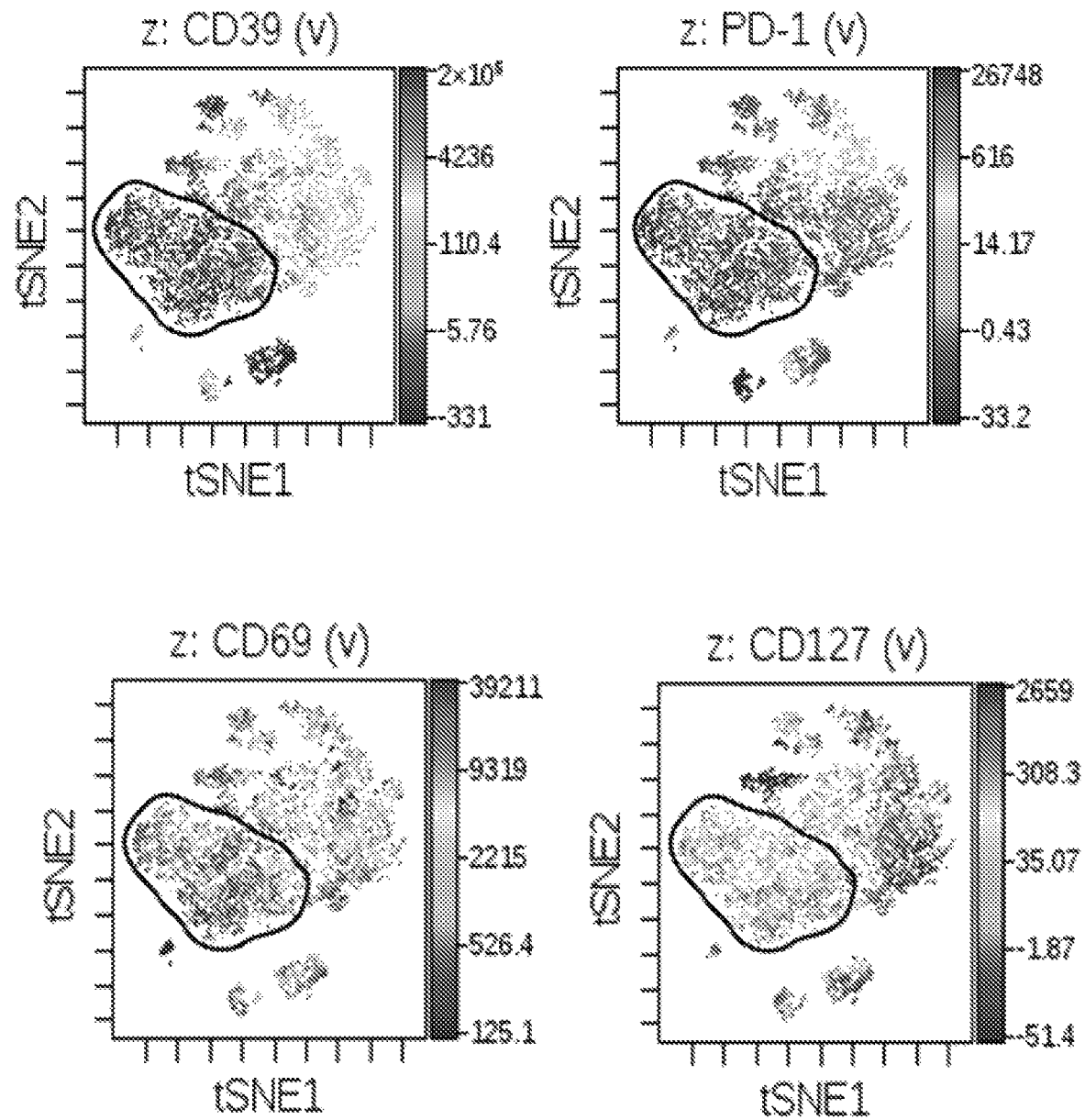
Figure 1C:
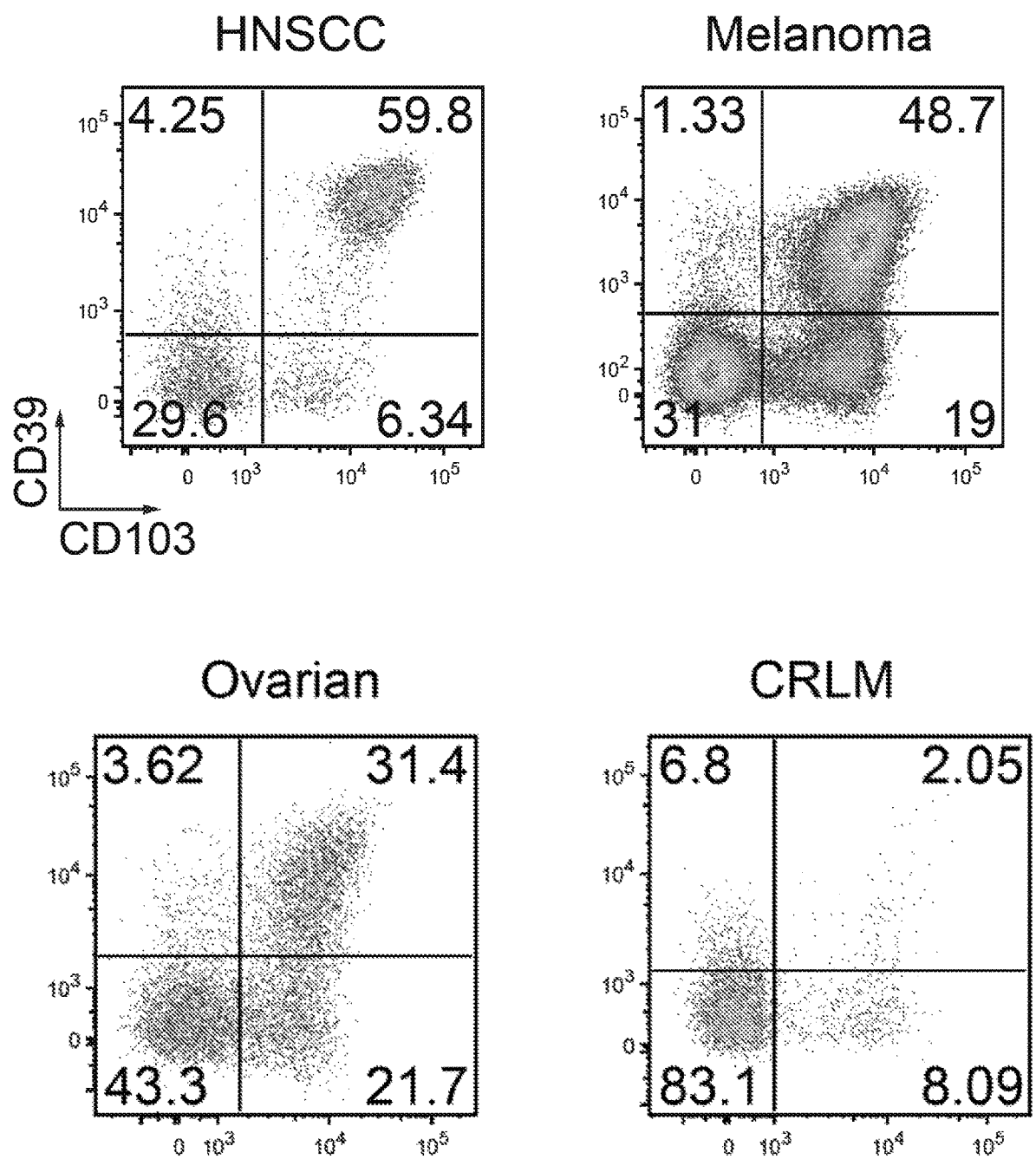
Figure 1D:
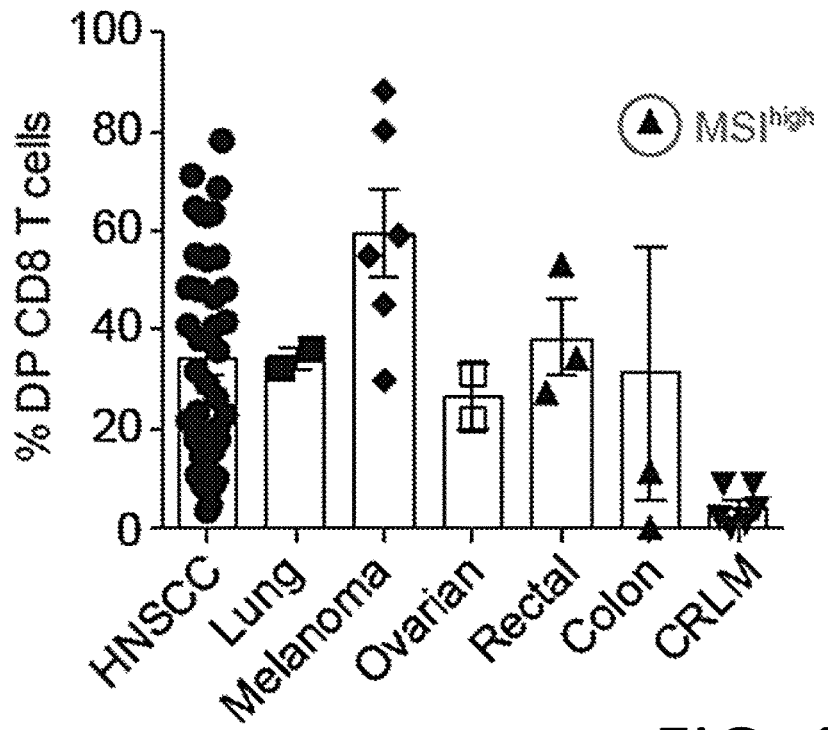

Identification of tumor-reactive CD8 T cells is key to assess the level and quality of the anti-tumor response in cancer patients and to understand the mode of action of new cancer treatment strategies such as immunotherapy. Recently, human tumor-reactive CD8 T cells have been identified by the co-expression of CD103 and PD-1 in high grade serous ovarin cancer (HGSC) and non-small cell lung cancer (NCLC). To further define their properties and function, tumor-infiltrating CD8 T cells (TIL) were sorted from two human ovarian tumors into CD103 positive and negative subsets and their gene expression profile was determined by microarray. For this analysis, attention was focused on differentially expressed cell surface molecules that could be easily detected by flow cytometry. One of the greatest differences observed in the gene array comparison that fulfilled the criteria was ENTPD1, a gene that encodes for CD39 and is found on the cell surface (Table 1). To confirm the gene array result and get a better understanding of the diversity of tumor-infiltrating CD8 T cells, CD8 T cells isolated from a head and neck squamous cell carcinoma (HNSCC) patient were stained and gated on the CD103+ population. CD39 and additional cell surface markers associated with activation/exhaustion as well as developmental state were examined. The complexity of the simultaneous analysis of all flow cytometry markers required a method called t-distributed stochastic neighbor embedding (t-SNE), widely used for mass cytometry data. Interestingly, high expression of CD39 on CD103+ CD8 T cells overlapped with high expression levels of PD-1 and CD69. Conversely, the CD103+ CD8 T cells expressed low levels of the IL-7R (CD127) (FIGS. 1A and 1B), suggesting a more effector-like T cell phenotype. Furthermore, the combined expression of CD103 and CD39 on CD8 T cells resulted in the identification of three distinct cell populations, which include the CD103−CD39− (double negative (DN) CD8), CD103+CD39− (single positive (SP) CD8) and CD103+CD39+ (double positive (DP) CD8). The DP CD8 T cells were detected at relatively high frequencies in several human solid malignancies including HNSCC, lung cancer, melanoma, ovarian cancer and rectal cancer (FIG. 1C), although melanoma had the highest frequency of these cells. In contrast, the DP CD8 T cells were present at quite low frequencies in a subset of HNSCC patients as well as most patients with colon cancer and colorectal liver metastasis (CRLM) (FIGS. 1C and 1D). Surprisingly, TIL from one colon cancer patient contained a very high frequency of DP CD8 T cells. This patient was diagnosed with Lynch syndrome, a rare hereditary disorder caused by mutations in mismatch repair genes leading to a higher rate of mutations. Interestingly, tumors with a greater frequency of mutations have a greater probability of having large number of neoantigens and those patients have a better outcome to checkpoint blockade immunotherapy as illustrated by prolonged progression-free survival (Le D T, N Engl J Med 2015; Snyder A, N Engl J Med 2014; Van Allen E M, Science 2015; Rizvi N A, Science 2015).

Figure 1F:
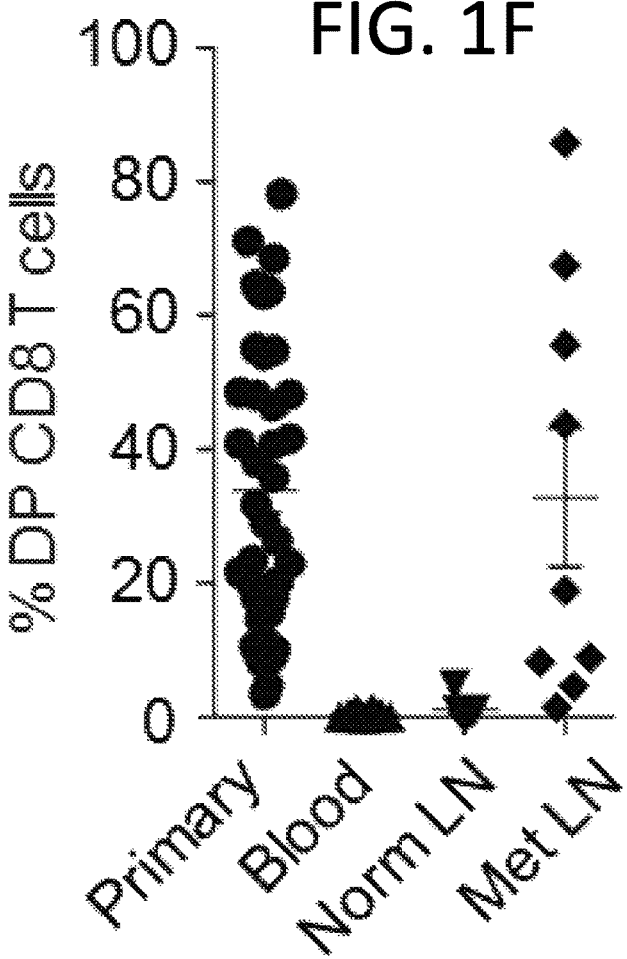
Figure 1E:
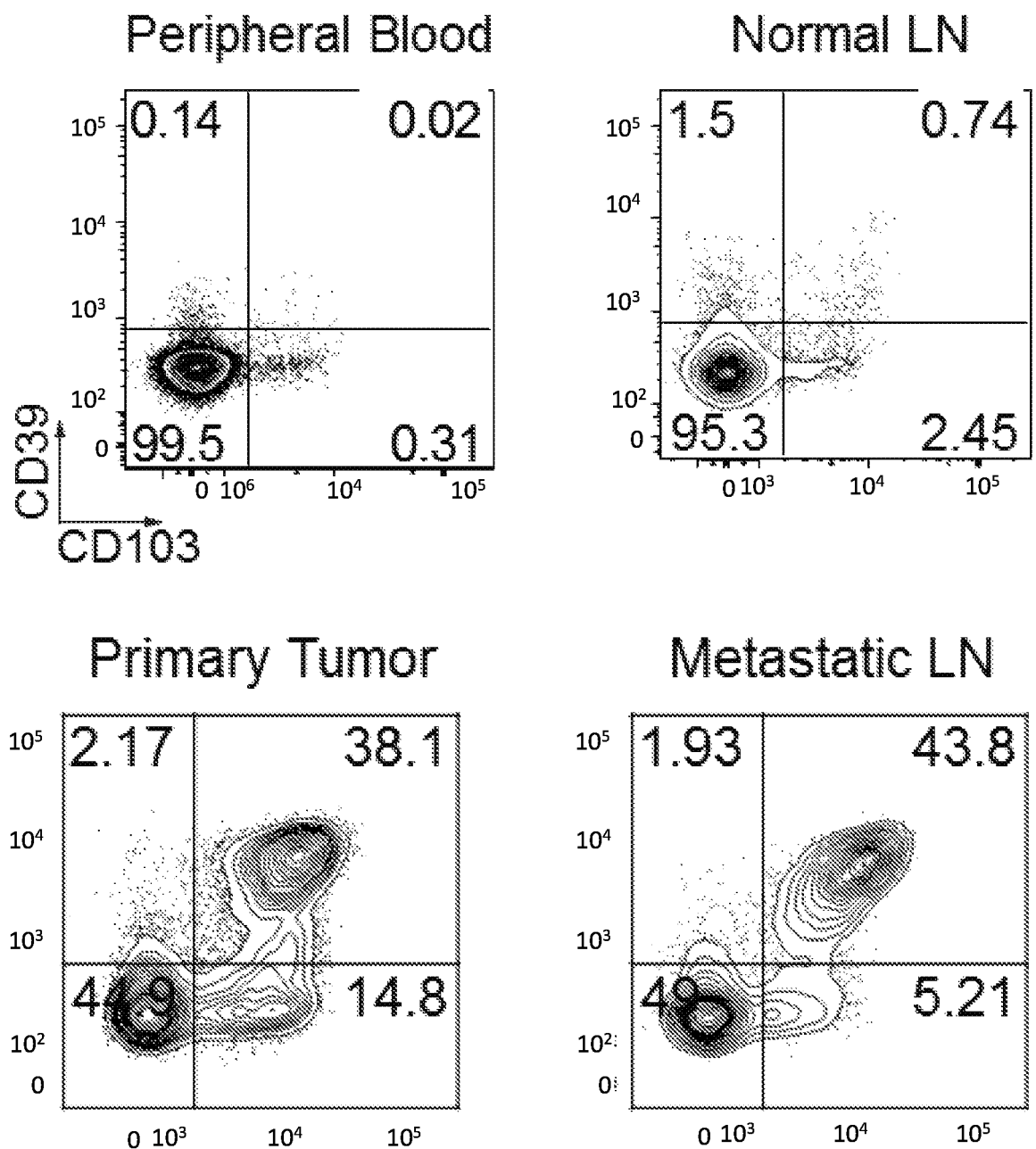

It was then examined whether the DP CD8 T cells were found only at sites where tumor cells were present. To address this, several HNSCC patients were analyzed where we obtained access to the primary tumor, metastatic lymph nodes (LN), uninvolved LNs and peripheral blood. In FIG. 1e results from a representative patient are shown, where the co-expression of CD39 and CD103 by CD8 T cells was specifically found in the primary tumor and metastatic LN but absent or present at very low frequency on CD8 T cells in the peripheral blood and the uninvolved LN. Importantly, this expression profile was confirmed in the majority of HNSCC patients that were analyzed (FIG. 1F). Therefore, the results show that CD39 expression on CD103+ CD8 T cells identifies a population of CD8 T cells specifically induced within the tumor microenvironment.

Figure 2A:
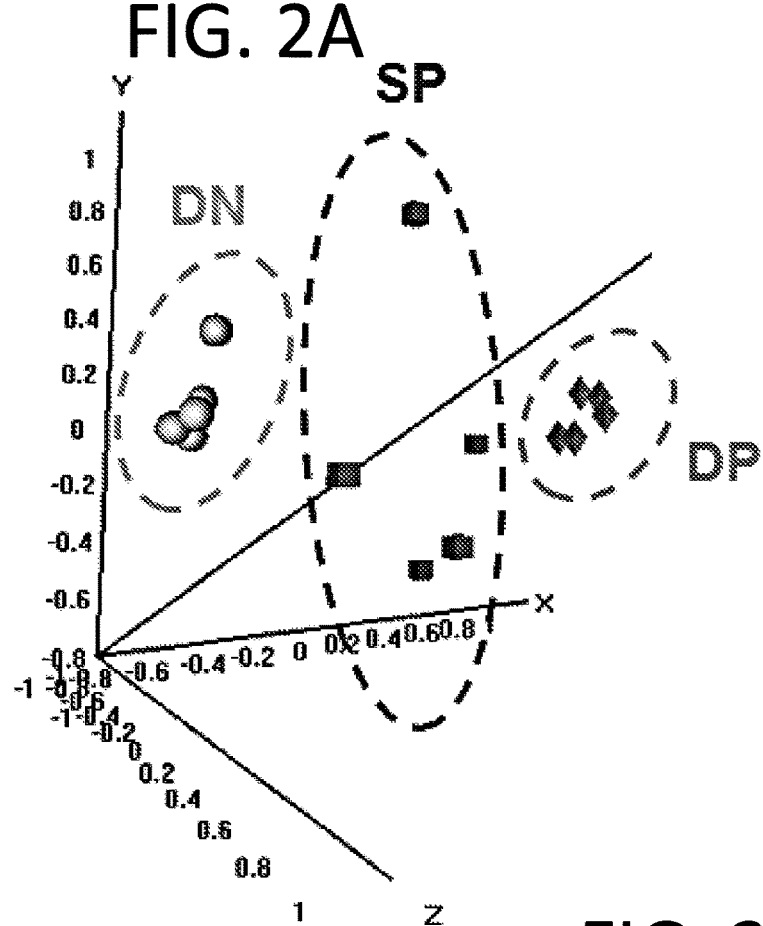
Figure 2B:
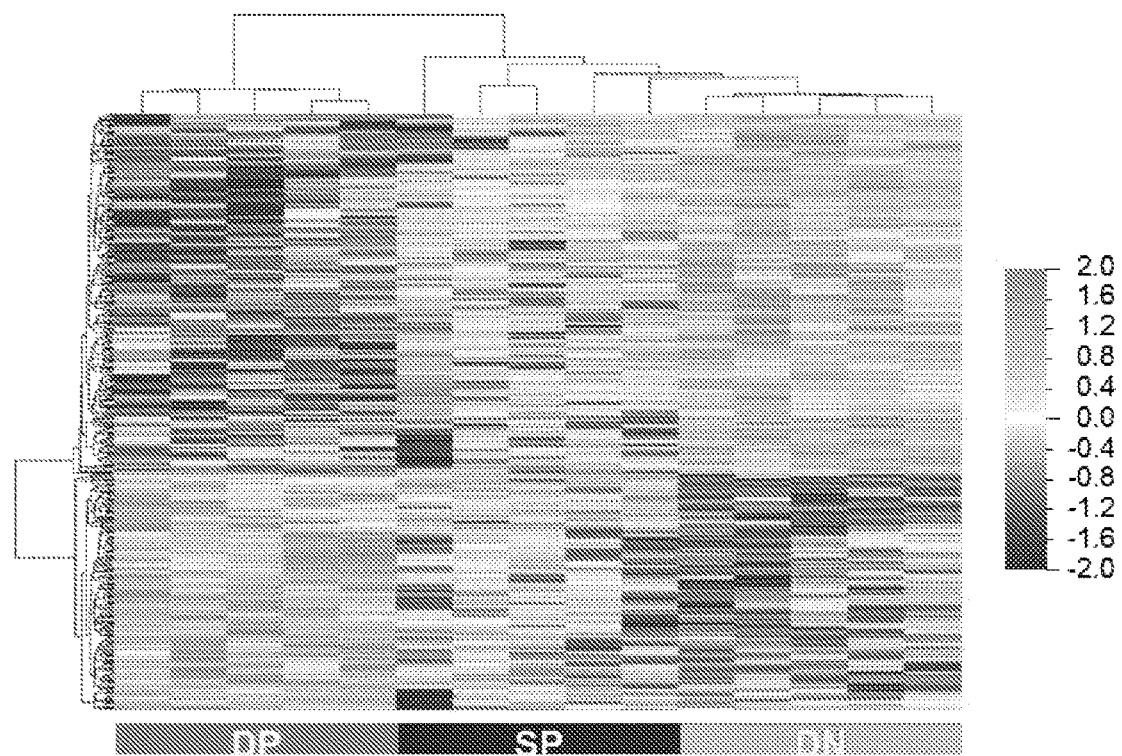
Figure 2D:
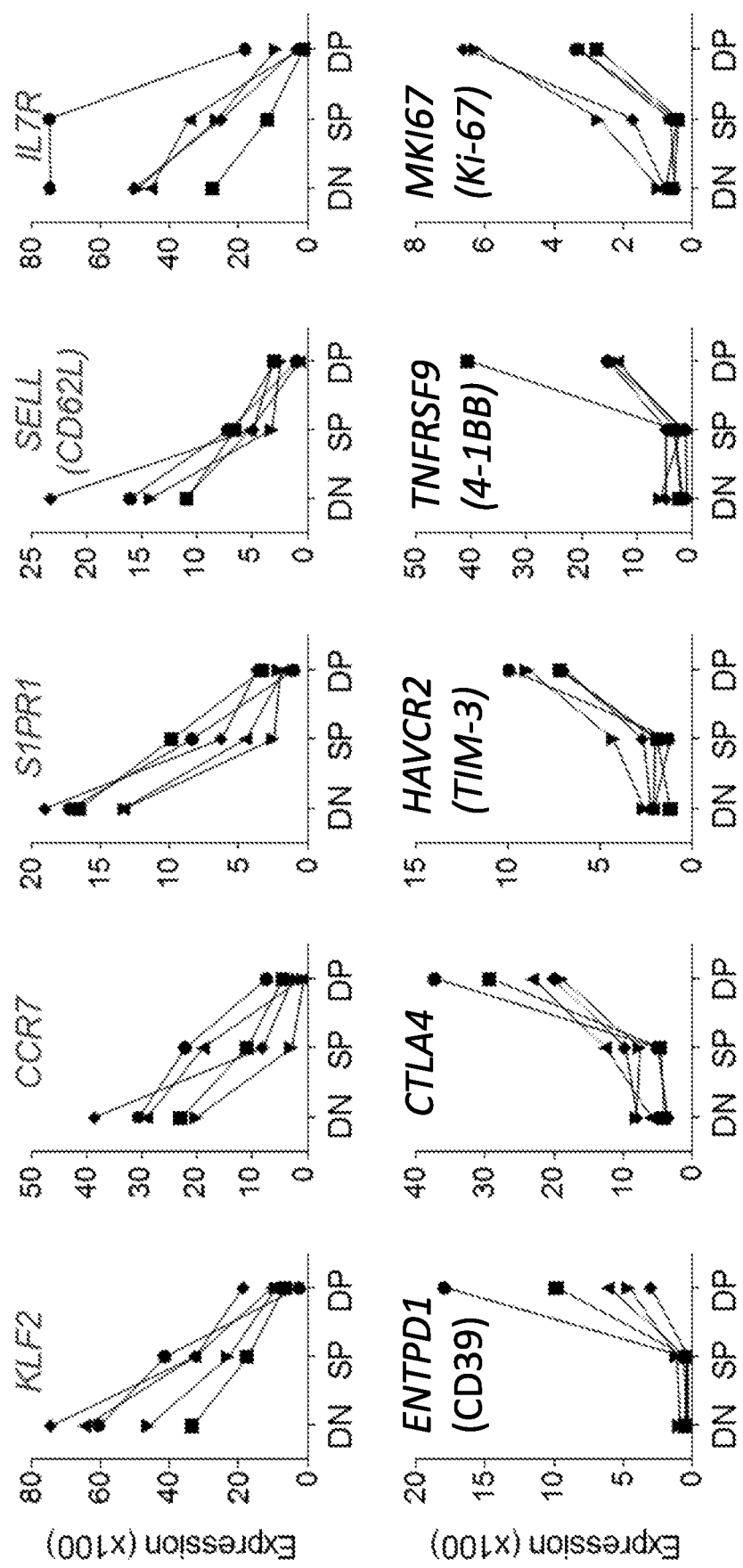
Figure 3B:
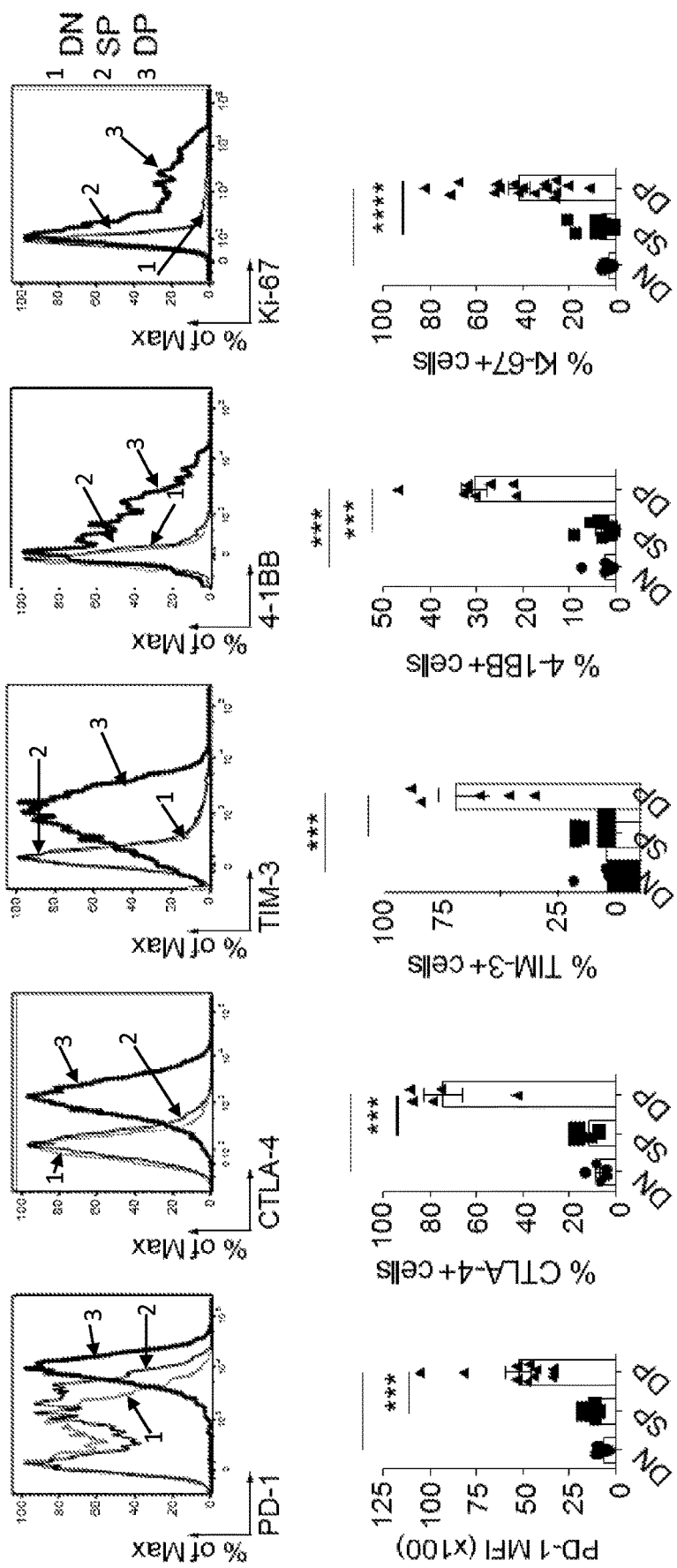

To better understand the biology of DN, SP and DP CD8 T cells, the three cell populations were sorted directly ex vivo and their global gene-expression profiles were determined by microarray. For this analysis, T cells were isolated from three HNSCC and two ovarian tumors. Comparison between DP and DN CD8 T cells identified 372 genes differentially expressed between these two cell populations. Principal Component Analysis and unsupervised hierarchical clustering on this selected gene list revealed that DP and DN CD8 T cells had distinct mRNA profiles, whereas SP CD8 T cells displayed an intermediate gene signature (FIGS. 2a and b). Principal Component Analysis and unsupervised hierarchical clustering performed on this selected set of genes revealed that the gene expression profile was cell type specific and did not segregated by patient (FIG. 2A, 2B). When comparing transcripts from the DP CD8 T cells relative to the DN CD8 T cells some of the greatest increases were associated with an activated/exhausted phenotype such as MK167, TNFRSF9, CTLA-4, HAVCR2, and GZMB. In contrast, the most down-regulated genes in DP CD8 T cells relative to DN CD8 T cells were involved in T cell recirculation patterns, such as KLF2, CCR7, SELL, S1PR1, KLF2. This gene expression profile is reminiscent of a T resident memory signature (FIG. 2C). Importantly, the expression profile for those activation and recirculation associated mRNAs was consistent across all five tumors (FIG. 2D). Therefore, the DP CD8 T cells display a gene expression signature of cells undergoing antigen-driven stimulation and activation in the tumor, which also may result in the loss recirculation out of the tumor tissue. To further assess the specific properties of tumor-infiltrating CD8 T cells, the expression of differentiation and activation markers was analyzed at the protein level by flow cytometry. The DP CD8 T cells expressed higher levels of CD69 when compared to SP or DN CD8 T cells (FIG. 3A). CD69 is an activation molecule that is up-regulated after T cell stimulation and antagonizes sphingosine 1-phosphate receptor 1 (S1PR1)-mediated egress from tissues (Mackay 2015; Skon 2013). The DP CD8 T cells also exhibited lower levels of CCR7, IL7R (CD127) and CD28, indicative of an effector memory phenotype (ref). Interestingly, even though DN and SP CD8 T cells expressed PD-1, the DP CD8 T cells expressed significantly higher levels of this protein (FIG. 3B). In addition, CTLA-4, and TIM-3 were almost exclusively expressed within DP CD8 T cell population. Hence the DP CD8 T cells displayed a highly activated effector memory phenotype especially when compared to the DN and SP CD8 T cells. Moreover, the increased frequency of 4-1BB and Ki-67 within the DP CD8 T cell population suggested that these cells were recently activated and proliferating within the tumor, which is indicative of recent cognate antigen recognition.

Figure 3C:
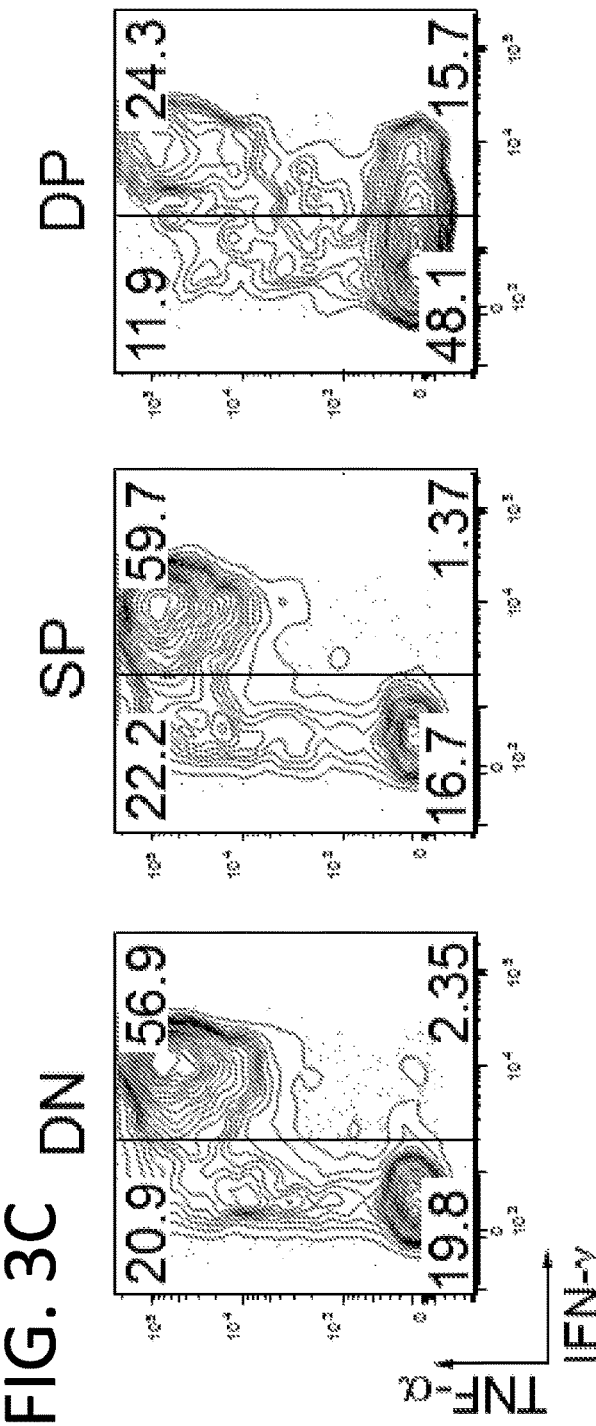
Figure 3D:
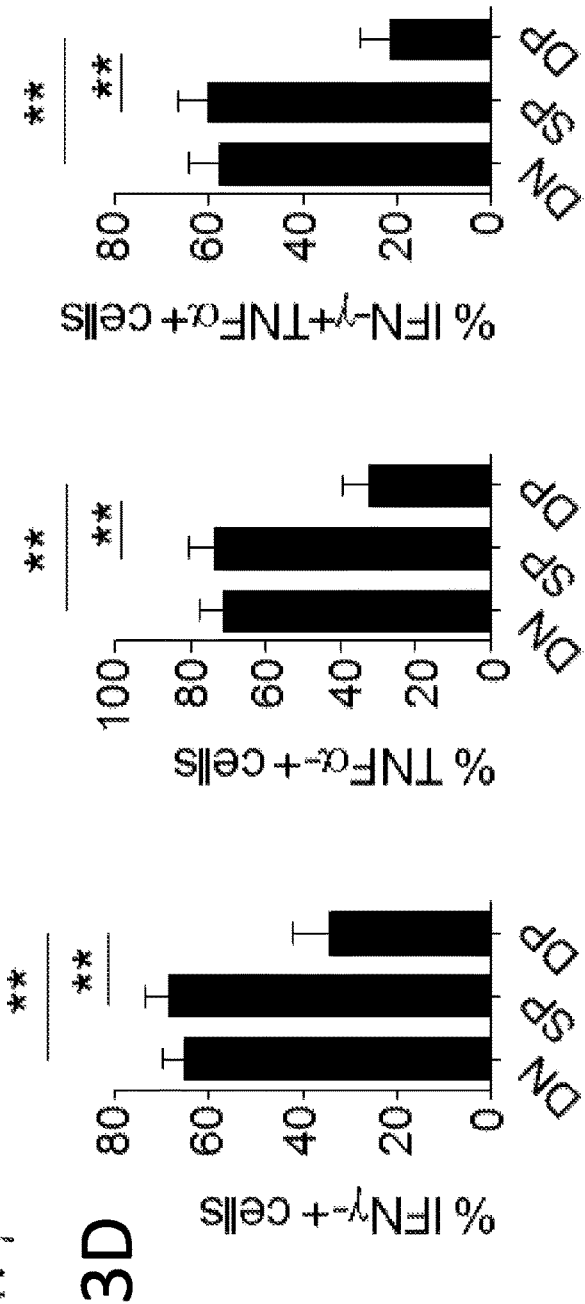
Figure 3E:
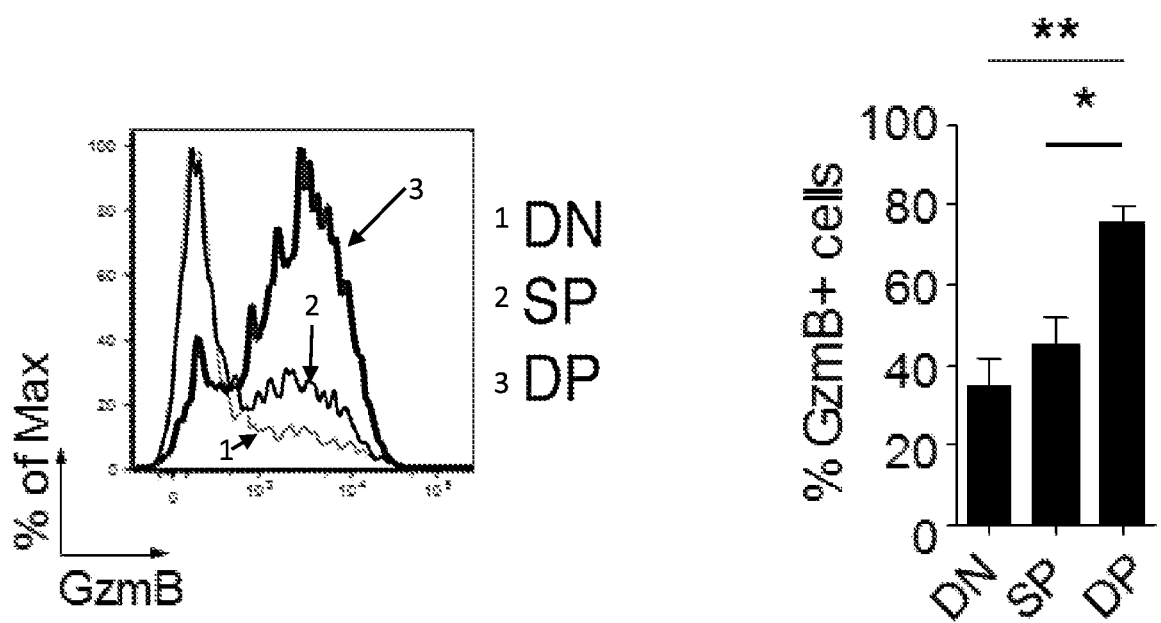

The effector function of DN, SP and DP CD8 T cells was assessed directly ex vivo by analyzing their cytokine production at the single cell level. The DP CD8 T cells had a lower frequency of cells capable of producing IFN-γ and or TNF-α when compared to DN and SP CD8 T cells and similar results were obtained in six HNSCC patients (FIG. 3C, 3D). In contrast, the DP CD8 T cells had an increased cytotoxic potential as demonstrated by a significantly higher frequency of granzyme B-positive cells (FIG. 3E).

Figure 4:
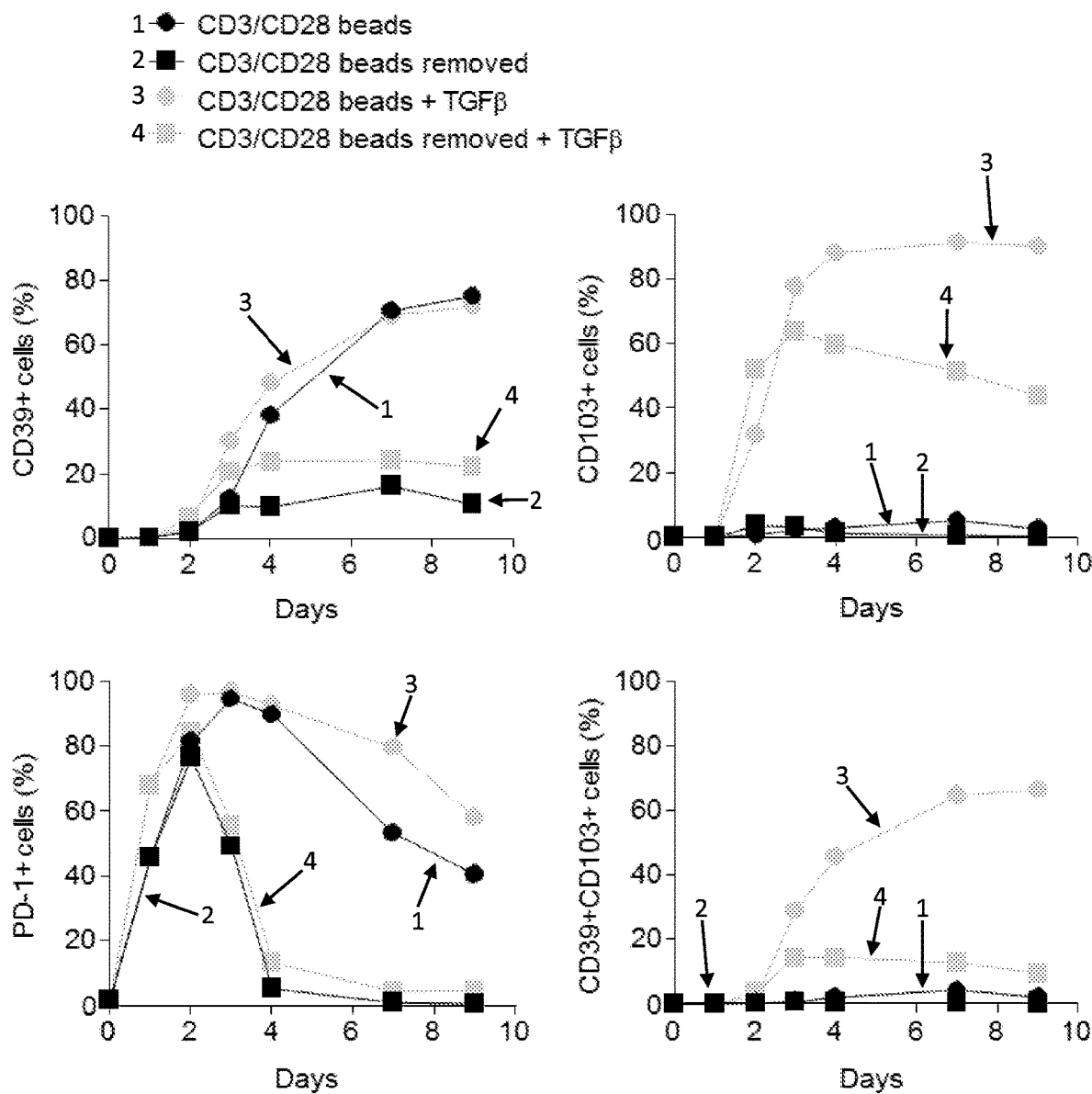
FIG. 4. Expression of CD39 and CD103 on CD8 T cells requires sustained stimulation in a TGF-β rich milieu. Kinetics of CD39, CD103 and PD-1 expression on sorted naive CD8 T cells from peripheral blood. Cells were stimulated with CD3/CD28 coated beads at a bead: T cell ratio of 1:2 in the presence or absence of TGF-β (2 ng/ml) and expression of CD39, CD103 and PD-1 was analyzed by flow cytometry at the indicated time points. Data are representative of 4 independent experiments.

Given that DP CD8 T cells were only found at sites where tumor cells were present, the factors responsible for this particular phenotype were identified to better understand the development of these cells. It is established that TGF-β drives expression of CD103 on T cells. TGF-β is produced within the tumor microenvironment and plays a major role in cancer progression through the induction of the epithelial-mesenchymal transition leading to enhanced motility and invasion. CD39 expression was found on chronically stimulated/exhausted CD8 T cells in a mouse model of chronic LCMV infection as well as in patients with chronic HCV and HIV infections (Gupta P K, PLOS Pathogen 2015), supporting a role for sustained TCR stimulation in its expression. Therefore, the kinetics of CD103 and CD39 upregulation were analyzed on naïve CD8 T cells after TCR engagement in the presence or absence of TGF-β (FIG. 4 and supplemental data). To address the role of sustained TCR stimulation in CD39 expression, T cell were stimulated continuously with CD3/CD28 beads for 9 days or the beads were removed 24 h after the initiation of the culture. CD39 expression was detected within 3 days of culture and its expression increased until day 9. CD103 was up-regulated when T cells were stimulated in the presence of TGF-β with more than 80% of cells positive after 7 days. Optimal CD103 and CD39 up-regulation was found only after sustained TCR stimulation. Importantly, the lack of CD39 up-regulation in the absence of sustained TCR stimulation was not due to limited T cell activation as the expression of other activation markers such as PD-1 was rapidly induced on the cells (FIG. 4). As opposed to CD103 expression, TGF-β had no effect on CD39 expression in the in vitro culture system. Thus, sustained TCR stimulation and TGF-β are the necessary factors required to promote the expression of CD103 and CD39 on CD8 T cells. Hence it appears that the DP CD8 T cells acquire their phenotype upon repeated exposure to their cognate antigen leading to chronic TCR signaling within the tumor in a TGF-β-rich environment.

Figure 5A:
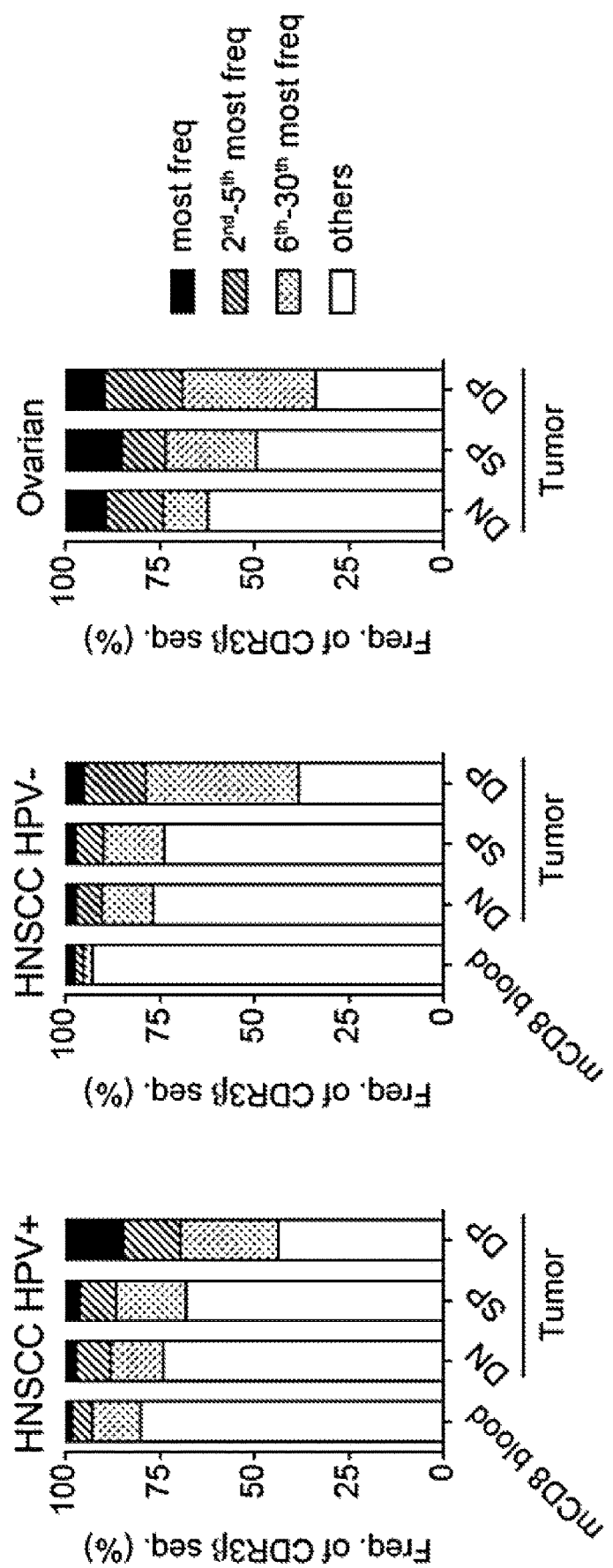
FIGS. 5A-5D. DP CD8 TIL are highly clonal and share little overlap with any other CD8 T cell subsets. (A) Diversity of the TCRβ repertoire within the blood memory CD8 T cells, DN, SP and DP CD8 TIL. The frequencies of the most frequent clonotype, the 2nd to 5th most frequent, the 6th to 30th most frequent, and the rest of the clonotypes are shown for HPV+ and HPV− HNSCC patients and one ovarian cancer patient. (B) The 500 most frequent CD8 TIL clonotypes are plotted based on their frequency in DN, SP and DP CD8 TIL subsets. Each dot represents a distinct TCR clonotype. Dots on the axis indicate the clonotypes detected within a single repertoire. (C) Same analysis as in (B) comparing the frequency of the top 500 clonotypes in memory CD8 T cells in blood and normal LN to the frequency of the top 500 clonotypes in DN and DP CD8 TIL subsets. (D) TCRβ sequence overlap analyzed using the Morisita-Horn index between the DP CD8 TIL, and the blood memory CD8 T cells, DN CD8 TIL and SP CD8 TIL. A TCRβ sequence overlap of I indicates 100% similarity between two populations.
Figure 5B:
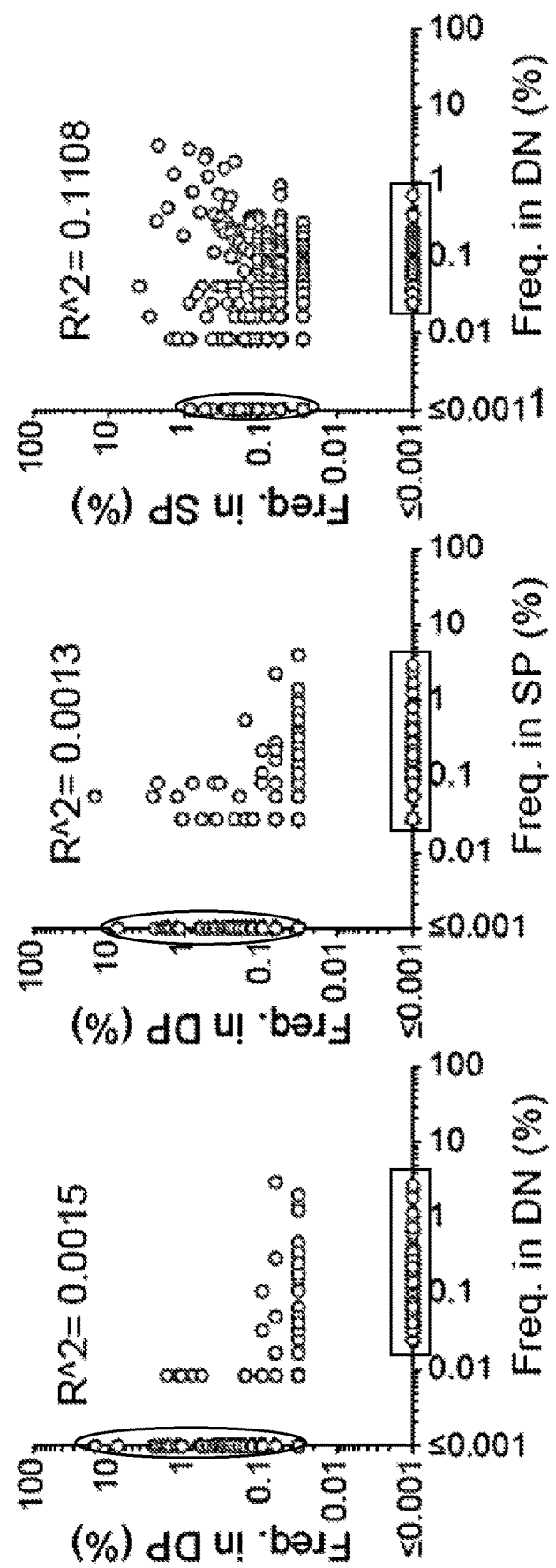
Figure 5C:
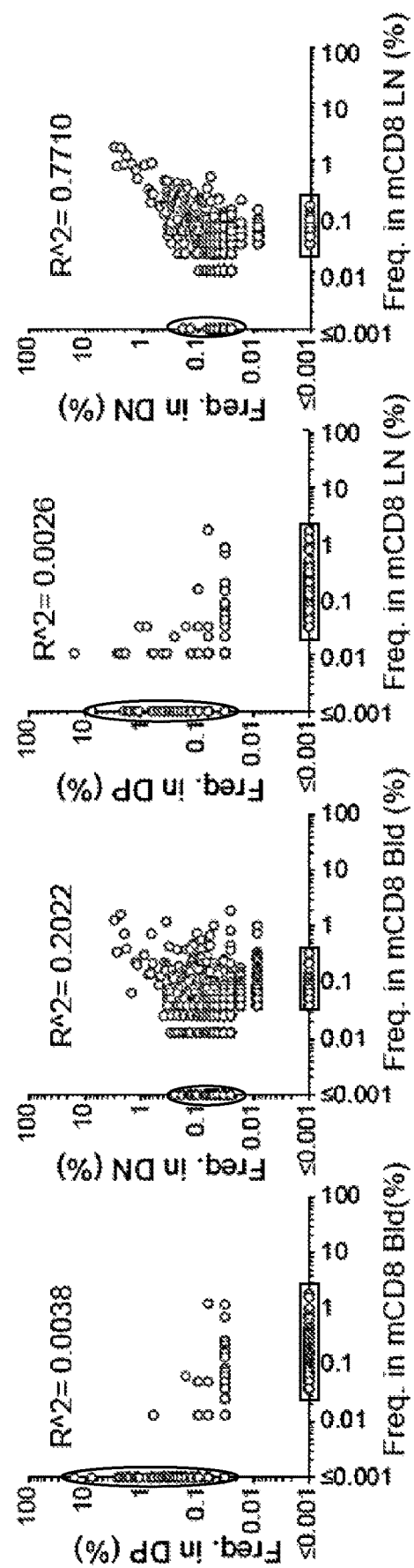
Figure 5D:
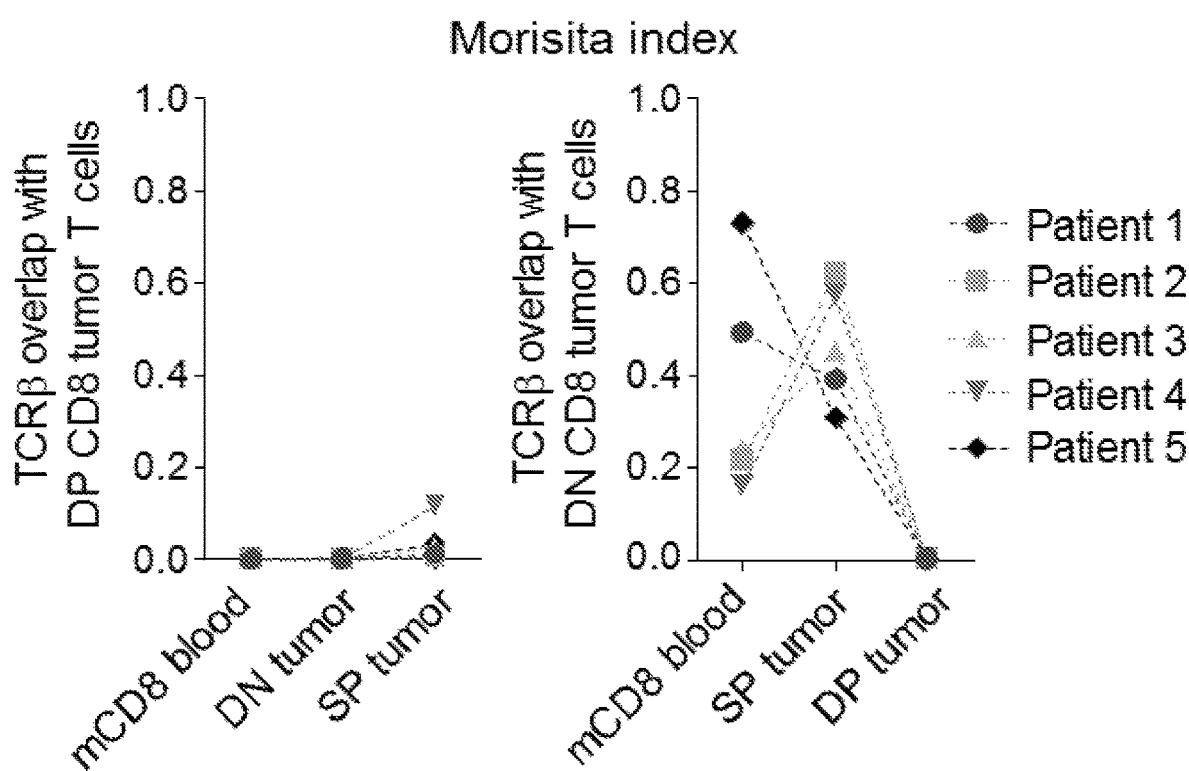

This data suggested that the DP CD8 T cells recognize their cognate antigens within the tumor site. If this is correct, it would lead to selective expansion of dominant TCR clonotypes, resulting in increased clonality when compared to the other CD8 T cell populations. To address this, the TCRβ clonotypes were assessed within the DN, SP and DP CD8 T cell populations as well as of total memory CD8 T cells from paired blood and uninvolved LN by sequencing the highly variable CDR3 region of the TCRB genes. DP CD8 T cells were more oligoclonal as compared to any other CD8 T cell population analyzed (FIG. 5A). The 30 most frequent clonotypes in each patient accounted for 56%, 61% and 66% of the DP CD8 T cell population—but only 26% and 23% and 38% of the DN CD8 T cells and less than 20% of the memory peripheral CD8 T cells—in an HPV+ HNSCC tumor, an HPV− HNSCC tumor, and an ovarian tumor, respectively. The 30 highest expanded DP CD8 T cell clonotypes were far less frequent in the DN CD8 T cell population, and represented less than 0.06% of the DN CD8 T cell repertoire for these three patients. Interestingly, there were very few shared TCR clonotypes between DP CD8 T cells and the other tumor-infiltrating CD8 T cell subsets (FIG. 5B). In contrast, a larger number of the TCR clonotypes were shared between DN CD8 T cells and SP CD8 T cells. As predicted by the resident memory signature (FIG. 2D), the majority of TCR clonotypes present in DN CD8 T cells were also shared with memory CD8 T cells within the tumor uninvolved LN as well as with memory CD8 T cells in the peripheral blood ($R^2=0.7710$ and 0.2022, respectively), suggesting that the DN CD8 T cells were able to recirculate, potentially sensing the tumor environment without ultimately recognizing their cognate antigen (FIG. 5C). In comparison, very few clonotypes present within DP CD8 T cells were detected in the uninvolved LN or peripheral blood. Calculation of the Morisita index, an abundance-based similarity index that determines the overlap between two populations further supported our results and showed consistency of this finding across 5 patient samples (FIG. 5D). Collectively, these results suggest that the DP CD8 T cells encounter their cognate antigen within the tumor site, which results in their activation and local expansion of tumor-specific T cell clones.

Figure 6A:
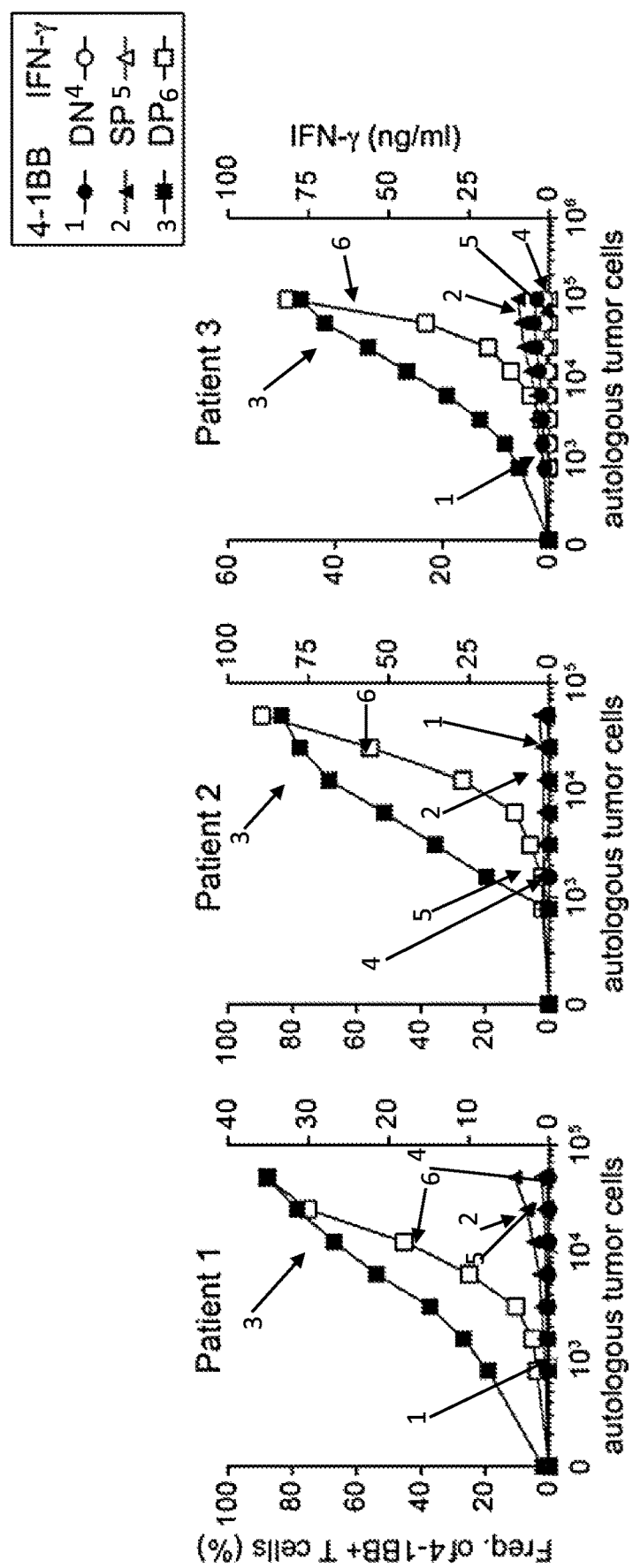
FIGS. 6A-6F. DP CD8 TIL recognize and kill autologous tumor cells and their frequency correlates with Improved overall survival. (A) Expanded CD8 TIL were tested for tumor reactivity by cultivating them for 20 hrs with increasing numbers of autologous tumor cells, and recognition was assessed by measuring the frequency of 4-1BB expression (filled symbols) and IFN-γ secretion (open symbols). Results are shown for three cancer patients. (B) Reactivity of DP CD8 TIL was confirmed by culture with autologous tumor cells with or without MHC-I blocking antibody, allogeneic tumor cells, and plate-bound anti-CD3. The up-regulation of 4-1BB after 20 hrs is shown for three cancer patients. (C) Tumor cell killing was measured by assessed the amount of caspase 3/7+ events/well monitored every hour over a 20 hrs period. (D) Representative images for DN and DP CD8 TIL taken at the beginning (T=0) and at the end of the coculture (T=20 hrs). (E) Overall survival on a cohort of 62 HNSCC patients based on the frequency of DP CD8 TIL among total CD8 TIL at the time of surgery. (F) Similar analysis performed on a cohort of 30 HPV-negative HNSCC patients.
Figure 6B:
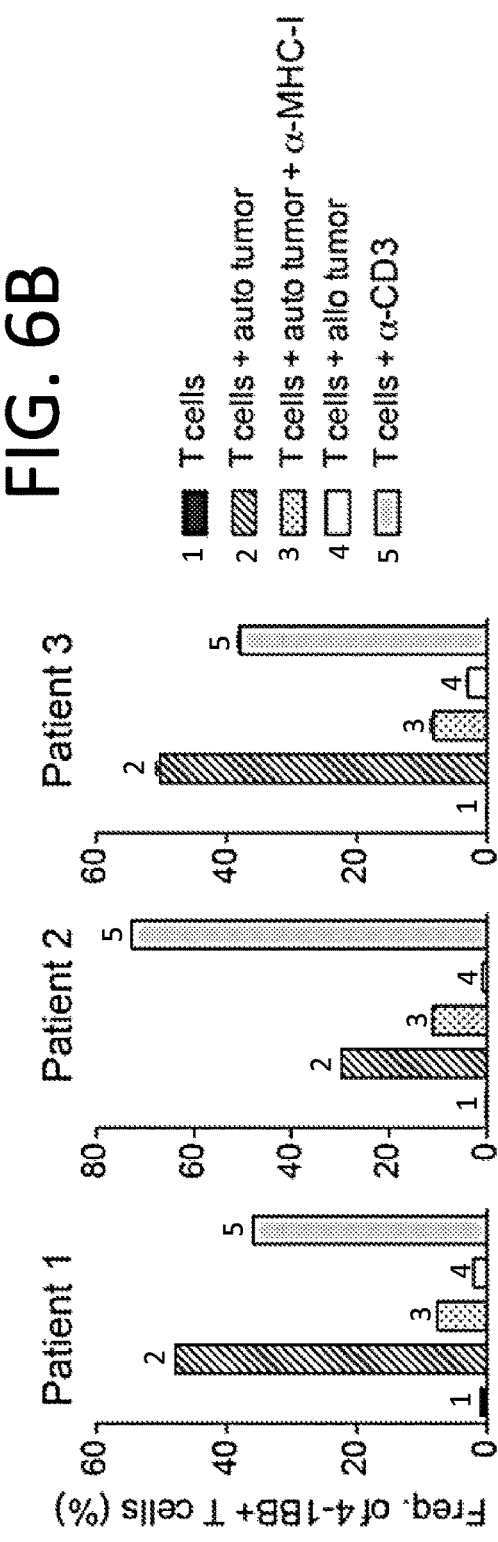
Figure 6C:
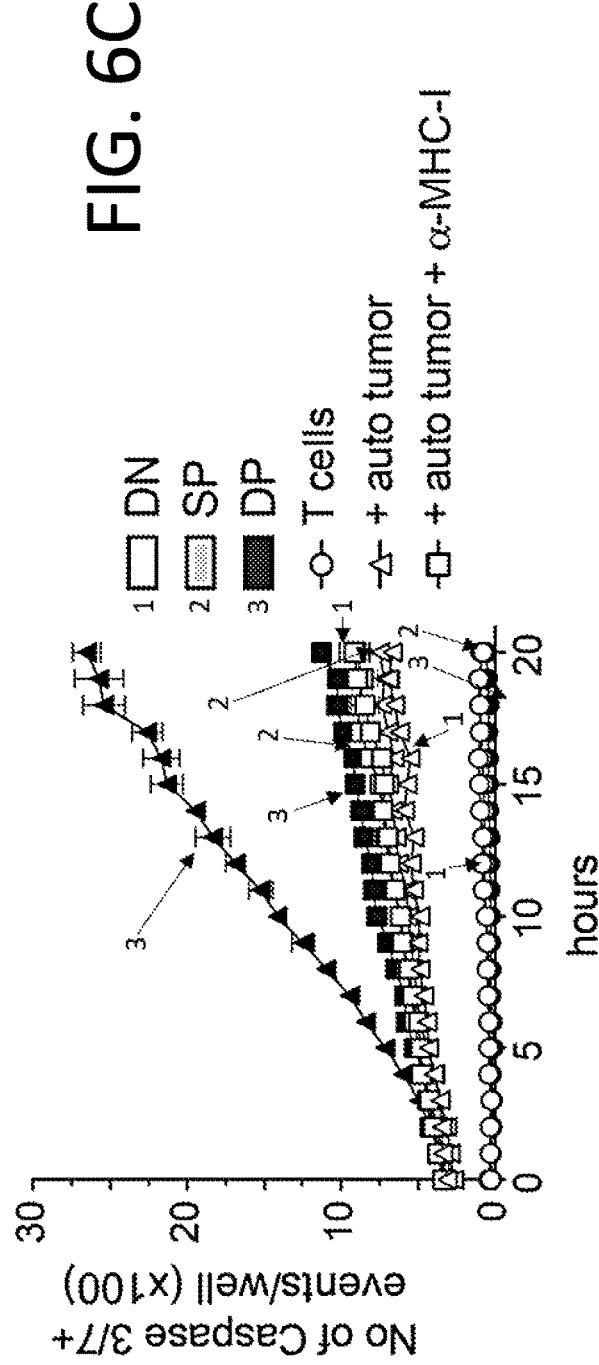
Figure 6D:
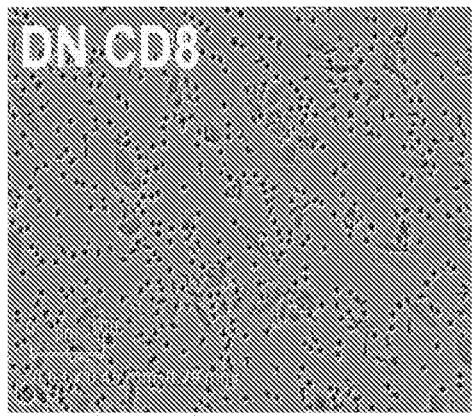
Figure 6D:
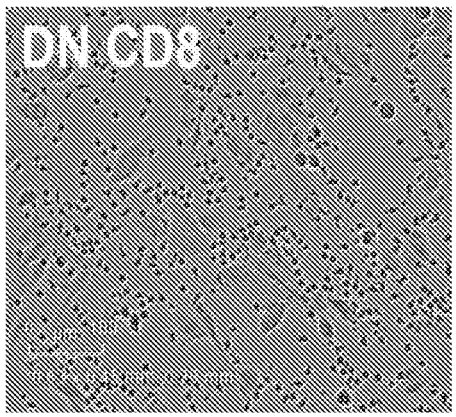
Figure 6D:
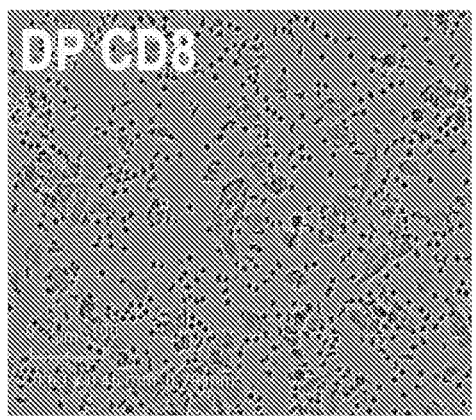
Figure 6D:
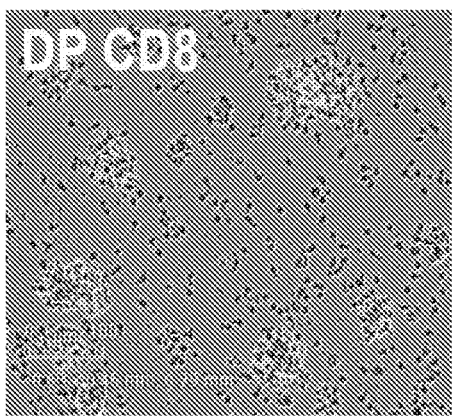

If this is correct, then the DP CD8 TIL should be enriched for tumor reactivity. Hence autologous tumor cell lines were generated from four melanoma tumors and two HNSCC tumors and we determined whether the DP CD8 TIL were enriched for tumor reactivity and killing. CD8 T cells were sorted directly from tumor digests based on the expression of CD103 and CD39 expression and the three CD8 T cell populations were expanded in vitro. Following expansion the DN, SP and DP CD8 TIL were screened for reactivity against autologous tumor cell lines as assessed by 4-1BB up-regulation as well as IFN-γ secretion. In all six patients tested it was found that the DP CD8 T cells were highly enriched for tumor reactivity when compared to the DN and SP CD8 TIL (FIG. 6A). The enrichment in tumor-reactive CD8 TIL among DP CD8 cells was illustrated by up to 87% reactive T cells at the highest tumor to T cell ratio for patient 1. Recognition of autologous tumor was specific and MHC class I restricted as no reactivity in the DP TIL subset was detected following MHC class I blockade or when cells were cultured with an allogeneic tumor cell line (FIG. 6B). To address whether the tumor-reactive DP CD8 T cells were capable of killing autologous tumor cells, the expanded T cell subsets were cocultured with autologous tumor cells and monitored for tumor-specific killing using the Incucyte live-cell analysis system. This system allows for visualization of caspase 3/7-dependent apoptosis by microscopy at 37° C. in real time. In accord with 4-1BB upregulation, only the DP CD8 T cells killed autologous tumor cells as illustrated by the increasing number of caspase 3/7+ events (FIG. 6C, 6D). This killing was MHC-class I dependent as the MHC-class I antibody W6/32 blocked this effect. In contrast there was little to no autologous tumor cell killing observed by the DN CD8 T cells.

Figure 6E:
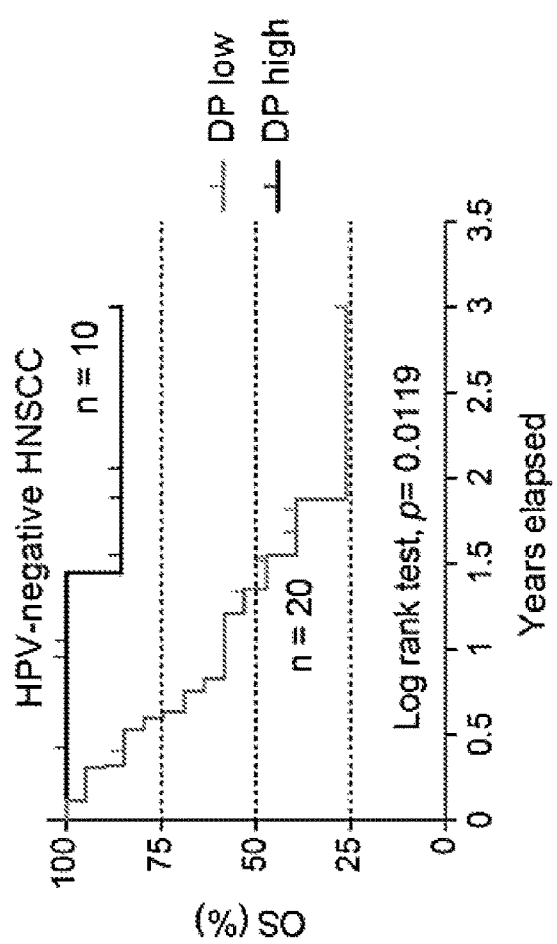
Figure 6F:
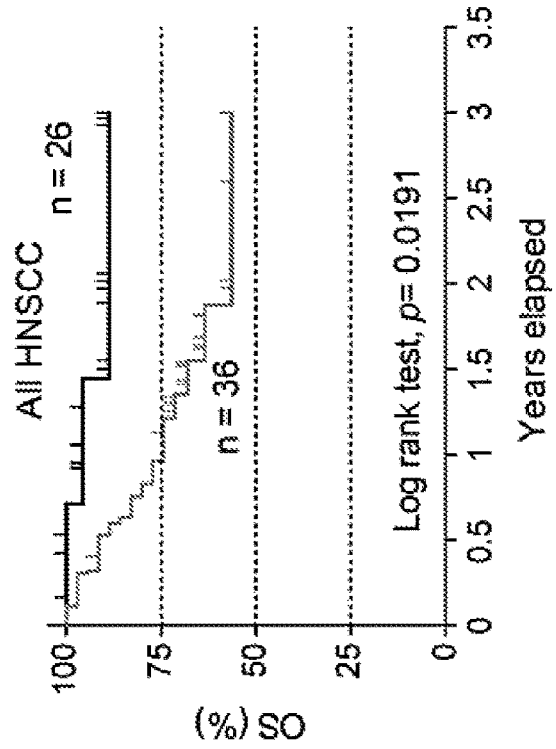

Finally, the relationship between the frequency of DP CD8 TIL and patient survival was assessed in surgical samples. This analysis focused on a small cohort of HNSCC patients (n=62). Following surgery, the frequency of DP CD8 T cells among total CD8 TIL was determined within primary tumors by flow cytometry and patients then received standard of care treatment(s). Patients were segregated based on the frequency of DP CD8 T cells, with a high and a low group relative to the average frequency of DP CD8 T cells for this cohort. Using this strategy, it was found that patients whose tumors had a higher percentage of DP CD8 TIL at the time of surgery correlated with increased overall survival (OS) (FIG. 6E), which showed greater significance in the HPV-negative subgroup (FIG. 6F). Collectively, it was shown that CD103 and CD39 co-expression strongly enriches for tumor-reactive CD8 TIL and their frequency correlated with an increase in overall survival in HNSCC patients.

Figure 7C:
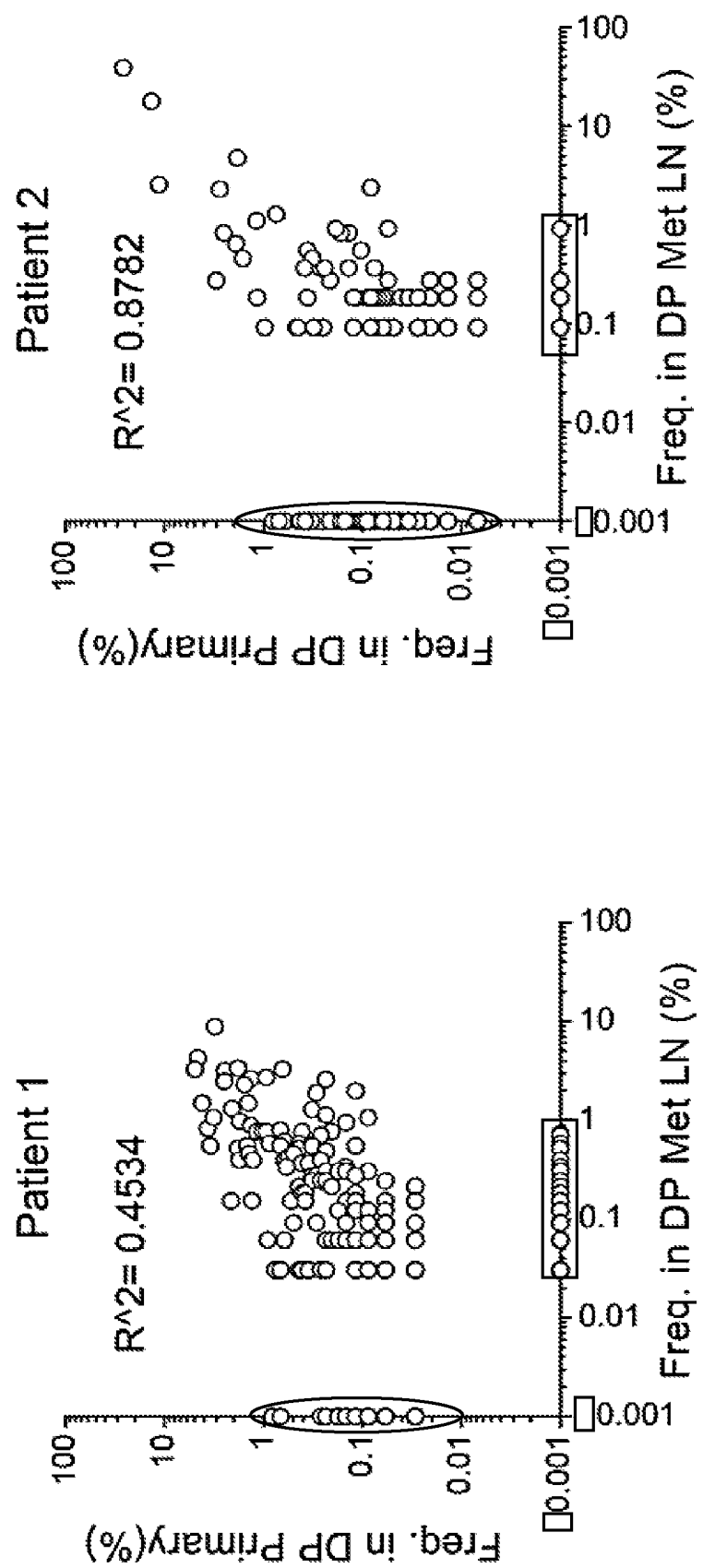

Based on these results, it was addressed whether the TCR clonotypes present at high frequencies in DP CD8 TIL were indeed tumor-specific. DP CD8 TIL were cocultured with autologous tumor cells for 20 hrs, followed by sorting of the 4-1BB+CD25+ CD8 T cells. The majority of the clonotypes present at high frequency ex-vivo were found within the 4-1BB+CD25+ fraction of DP CD8 TIL when these T cells were co-cultured with autologous tumor lines, demonstrating that they were tumor reactive (FIG. 7A. 7B). The data imply that utilizing TCRs from the DP CD8 population, would be therapeutic in an adoptive transfer setting. Of note, a strong overlap of the DP CD8 TIL TCR repertoire was observed between the primary tumor and metastatic LN within the same patient, in two different HNSCC samples (FIG. 7C). This result is significant as it suggests that the same DP CD8 TIL TCR could be isolated from either a metastatic LN or primary tumor and used for TCR therapy.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of treating a subject with a tumor, comprising administering to the subject a therapeutically effective amount of CD8$^+$CD39$^+$CD103$^+$ T cells, thereby treating the subject with the tumor.

2. The method of claim 1, further comprising administering a therapeutically effective amount of a Programmed Death (PD)-1 antagonist, a Programmed Death Ligand (PD-L1) antagonist, a Cytotoxic T-lymphocyte-Associated Protein 4 (CTLA-4) antagonist, a B- and T-lymphocyte Attenuator (BTLA) antagonist, T-cell Immunoglobulin and Mucin-domain containing-3 (TIM-3) antagonist, a Lymphocyte-Activation Gene 3 (LAG3) antagonist, or a 4-1BB agonist to the subject.

3. The method of claim 2, wherein a) the PD-1 antagonist is an antibody that specifically binds PD-1, or an antigen binding fragment thereof; b) the PD-L1 antagonist is an antibody that specifically binds PD-L1 or an antigen binding fragment thereof; c) the CTLA-4 antagonist is an antibody that specifically binds CTLA-4 or an antigen binding fragment thereof; d) the BTLA antagonist is an antibody that specifically binds BTLA or an antigen binding fragment thereof; e) the TIM-3 antagonist is an antibody that specifically binds TIM-3 or an antigen binding fragment thereof; e) the LAG3 antagonist is an antibody that specifically binds LAG3 or an antigen binding thereof.

4. The method of claim 3, wherein the antibody that specifically binds PD-1, the antibody that specifically binds PD-L1, the antibody that specifically binds CTLA-4, the antibody that specifically binds BTLA, the antibody that specifically binds TIM-3 or the antibody that specifically binds LAG3, is a human monoclonal antibody or a humanized monoclonal antibody.

5. The method of claim 1, wherein the tumor is a solid tumor.

6. The method of claim 5, wherein the solid tumor is a head and neck squamous cell carcinoma, lung cancer, melanoma, ovarian cancer renal cell carcinoma, bladder cancer, cervical cancer, liver cancer, prostate cancer, breast cancer, glioblastoma or rectal cancer.

7. The method of claim 1, wherein the CD8$^+$CD39$^+$CD103$^+$ T cells are autologous.

8. The method of claim 1, wherein the subject is human.

9. The method of claim 1, further comprising resecting the tumor in the subject.

10. The method of claim 6, wherein the solid tumor is a melanoma.

* * * * *

UNITED STATES PATENT AND TRADEMARK OFFICE
CERTIFICATE OF CORRECTION

PATENT NO. : 11,572,541 B2  
APPLICATION NO. : 16/616932  
DATED : February 7, 2023  
INVENTOR(S) : Weinberg et al.

Page 1 of 1

It is certified that error appears in the above-identified patent and that said Letters Patent is hereby corrected as shown below:

On the Title Page

Item (72) Inventors:
Line 2: "Ryan Montier" should read --Ryan Montler--.

Signed and Sealed this
Twenty-fifth Day of July, 2023

Katherine Kelly Vidal
*Director of the United States Patent and Trademark Office*

SEQUENCE LISTING

```
<160> NUMBER OF SEQ ID NOS: 30

<210> SEQ ID NO 1
<211> LENGTH: 87
<212> TYPE: DNA
<213> ORGANISM: Homo sapiens

<400> SEQUENCE: 1
ccgctcaggc tggagttggc tgctccctcc cagacatctg tgtacttctg tgccagcagt      60
tggggtggcg agcagtactt cgggccg                                         87

<210> SEQ ID NO 2
<211> LENGTH: 87
<212> TYPE: DNA
<213> ORGANISM: Homo sapiens

<400> SEQUENCE: 2
ctgagctctc tggagctggg ggactcagct ttgtatttct gtgccagcag cgggacagtt      60
aacaccgggg agctgttttt tggagaa                                         87

<210> SEQ ID NO 3
<211> LENGTH: 87
<212> TYPE: DNA
<213> ORGANISM: Homo sapiens

<400> SEQUENCE: 3
gagtccgcca gcaccaacca gacatctatg tacctctgtg ccagcagttt ccgggacagg      60
gggcttcagc cccagcattt tggtgat                                         87

<210> SEQ ID NO 4
<211> LENGTH: 87
<212> TYPE: DNA
<213> ORGANISM: Homo sapiens
```

```
<400> SEQUENCE: 4
acgatccagc gcacacagca ggaggactcg gccgtgtatc tctgtgccag cagctcgaca    60
gggggctacg agcagtactt cgggccg                                       87

<210> SEQ ID NO 5
<211> LENGTH: 87
<212> TYPE: DNA
<213> ORGANISM: Homo sapiens

<400> SEQUENCE: 5
ctgagctctc tggagctggg ggactcagct ttgtatttct gtgccagcag cttcggacag    60
ggggcctacg agcagtactt cgggccg                                       87

<210> SEQ ID NO 6
<211> LENGTH: 87
<212> TYPE: DNA
<213> ORGANISM: Homo sapiens

<400> SEQUENCE: 6
cagcgcacag agcagggga ctcggccatg tatctctgtg ccagcaggca ggagacagcc    60
gggaacactg aagctttctt tggacaa                                       87

<210> SEQ ID NO 7
<211> LENGTH: 87
<212> TYPE: DNA
<213> ORGANISM: Homo sapiens

<400> SEQUENCE: 7
ctggagtccg ccagcaccaa ccagacatct atgtacctct gtgccagcag tttagctaga    60
aacaccgggg agctgttttt tggagaa                                       87

<210> SEQ ID NO 8
<211> LENGTH: 87
<212> TYPE: DNA
<213> ORGANISM: Homo sapiens

<400> SEQUENCE: 8
aagatccagc ctgcaaagct tgaggactcg gccgtgtatc tctgtgccag cagcacgact    60
agttcagata cgcagtattt tggccca                                       87

<210> SEQ ID NO 9
<211> LENGTH: 87
<212> TYPE: DNA
<213> ORGANISM: Homo sapiens

<400> SEQUENCE: 9
cagcgcacag agcagcggga ctcggccatg tatcgctgtg ccagcagcga ggagcccggg    60
atcgatgaaa aactgttttt tggcagt                                       87

<210> SEQ ID NO 10
<211> LENGTH: 87
<212> TYPE: DNA
<213> ORGANISM: Homo sapiens

<400> SEQUENCE: 10
gagtcgccca gccccaacca gacctctctg tacttctgtg ccagcagtct cggggatat    60 agcaatcagc cccagcattt tggtgat                                       87
```

<210> SEQ ID NO 11
<211> LENGTH: 87
<212> TYPE: DNA
<213> ORGANISM: Homo sapiens

<400> SEQUENCE: 11
actctgacag tgaccagtgc ccatcctgaa gacagcagct tctacatctg cagcgcttgg    60
acaggctacg agcagtactt cgggccg                                       87

<210> SEQ ID NO 12
<211> LENGTH: 87
<212> TYPE: DNA
<213> ORGANISM: Homo sapiens

<400> SEQUENCE: 12
atccagcgca cacagcagga ggactccgcc gtgtatctct gtgccagcac ccaactatta    60
atgatcaatg agcagttctt cgggcca                                       87

<210> SEQ ID NO 13
<211> LENGTH: 87
<212> TYPE: DNA
<213> ORGANISM: Homo sapiens

<400> SEQUENCE: 13
cgcacagagc aggggactc ggccatgtat ctctgtgcca gcagttatgg ccccgggaca    60
gttaatgaaa aactgttttt tggcagt                                       87

<210> SEQ ID NO 14
<211> LENGTH: 87
<212> TYPE: DNA
<213> ORGANISM: Homo sapiens

<400> SEQUENCE: 14
ctggagtcgg ctgctccctc ccagacatct gtgtacttct gtgccagcaa gggccccttt    60
gggcggaatg agcagttctt cgggcca                                       87

<210> SEQ ID NO 15
<211> LENGTH: 87
<212> TYPE: DNA
<213> ORGANISM: Homo sapiens

<400> SEQUENCE: 15
atccagcgca cagagcaggg ggactcggcc atgtatctct gtgccagcag ctcgattctc    60
ggggcgggga cgcagtattt tggccca                                       87

<210> SEQ ID NO 16
<211> LENGTH: 87
<212> TYPE: DNA
<213> ORGANISM: Homo sapiens

<400> SEQUENCE: 16
cgcacagagc aggggactc ggccatgtat ctctgtgcca gcagccgcac tcaggggtcg    60
ggtaaggagc cccagcattt tggtgat                                       87

<210> SEQ ID NO 17
<211> LENGTH: 87
<212> TYPE: DNA

<400> SEQUENCE: 17
tctaagaagc tccttctcag tgactctggc ttctatctct gtgcctggag tgtgggactc    60
cagaacactg aagctttctt tggacaa                                        87

<210> SEQ ID NO 18
<211> LENGTH: 87
<212> TYPE: DNA
<213> ORGANISM: Homo sapiens

<400> SEQUENCE: 18
ctgagctctc tggagctggg ggactcagct ttgtatttct gtgccagcag cgaagggtat    60
ccgtcagaaa aactgttttt tggcagt                                        87

<210> SEQ ID NO 19
<211> LENGTH: 87
<212> TYPE: DNA
<213> ORGANISM: Homo sapiens

<400> SEQUENCE: 19
aagatccggt ccacaaagct ggaggactca gccatgtact tctgtgccag aaacaggggt    60
aaggggaatg agcagttctt cgggcca                                        87

<210> SEQ ID NO 20
<211> LENGTH: 87
<212> TYPE: DNA
<213> ORGANISM: Homo sapiens

<400> SEQUENCE: 20
ccgctcaggc tggagttggc tgctccctcc cagacatctg tgtacttctg tgccagcagt    60
tggggtggcg agcagtactt cgggccg                                        87

<210> SEQ ID NO 21
<211> LENGTH: 87
<212> TYPE: DNA
<213> ORGANISM: Homo sapiens

<400> SEQUENCE: 21
actgtgacat cggcccaaaa gaacccgaca gctttctatc tctgtgccag caacccaggg    60
tggtacactg aagctttctt tggacaa                                        87

<210> SEQ ID NO 22
<211> LENGTH: 87
<212> TYPE: DNA
<213> ORGANISM: Homo sapiens

<400> SEQUENCE: 22
atccagccct cagaacccag ggactcagct gtgtacttct gtgccagcag cccgcggggg    60
tcttacaatg agcagttctt cgggcca                                        87

<210> SEQ ID NO 23
<211> LENGTH: 87
<212> TYPE: DNA
<213> ORGANISM: Homo sapiens

<400> SEQUENCE: 23
cagcgcacag agcaggggga ctcggccatg tatctctgtg ccagcagctc cccgggtagc    60
tcctacaatg agcagttctt cgggcca                                        87

<210> SEQ ID NO 24
<211> LENGTH: 87
<212> TYPE: DNA
<213> ORGANISM: Homo sapiens

<400> SEQUENCE: 24
atcaattccc tggagcttgg tgactctgct gtgtatttct gtgccagcag ctttggacag    60
ggggcctacg agcagtactt cgggccg                                       87

<210> SEQ ID NO 25
<211> LENGTH: 87
<212> TYPE: DNA
<213> ORGANISM: Homo sapiens

<400> SEQUENCE: 25
aagaagctcc ttctcagtga ctctggcttc tatctctgtg cccttatact agtcgggaca    60
atacgagaga cccagtactt cgggcca                                       87

<210> SEQ ID NO 26
<211> LENGTH: 87
<212> TYPE: DNA
<213> ORGANISM: Homo sapiens

<400> SEQUENCE: 26
gagtcgccca gccccaacca gacctctctg tacttctgtg ccagcagtct cggggatat    60 agcaatcagc cccagcattt tggtgat                                       87

<210> SEQ ID NO 27
<211> LENGTH: 87
<212> TYPE: DNA
<213> ORGANISM: Homo sapiens

<400> SEQUENCE: 27
actgtgacat cggcccaaaa gaacccgaca gctttctatc tctgtgccag tattagtggg    60
tggggcactg aagctttctt tggacaa                                       87

<210> SEQ ID NO 28
<211> LENGTH: 87
<212> TYPE: DNA
<213> ORGANISM: Homo sapiens

<400> SEQUENCE: 28
cgcacagagc aggggactc ggccatgtat ctctgtgcca gcagttatgg ccccgggaca    60
gttaatgaaa aactgttttt tggcagt                                       87

<210> SEQ ID NO 29
<211> LENGTH: 87
<212> TYPE: DNA
<213> ORGANISM: Homo sapiens

<400> SEQUENCE: 29
gcccaaaaga acccgacagc tttctatctc tgtgccagta gtcccccccg acagggtcg    60 cggcaagaga cccagtactt cgggcca                                       87

<210> SEQ ID NO 30
<211> LENGTH: 87
<212> TYPE: DNA
<213> ORGANISM: Homo sapiens

```
<400> SEQUENCE: 30
ctaaacctga gctctctgga gctgggggac tcagctttgt atttctgtgc cagcagcgga        60 caggggggcga agcagtactt cgggccg                                            87
```